US007354760B2

(12) United States Patent
Daniell

(10) Patent No.: US 7,354,760 B2
(45) Date of Patent: Apr. 8, 2008

(54) EXPRESSION OF PROTECTIVE ANTIGENS IN TRANSGENIC CHLOROPLASTS

(75) Inventor: Henry Daniell, Winter Park, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 10/500,351

(22) PCT Filed: Dec. 26, 2002

(86) PCT No.: PCT/US02/41503

§ 371 (c)(1),
(2), (4) Date: Jan. 3, 2005

(87) PCT Pub. No.: WO03/057834

PCT Pub. Date: Jul. 17, 2003

(65) Prior Publication Data

US 2005/0108792 A1 May 19, 2005

Related U.S. Application Data

(60) Provisional application No. 60/344,704, filed on Dec. 26, 2001, provisional application No. 60/393,428, filed on Jul. 3, 2002, provisional application No. 60/393,651, filed on Jul. 3, 2002, provisional application No. 60/400,816, filed on Aug. 2, 2002.

(51) Int. Cl.
*C12N 15/82* (2006.01)
(52) U.S. Cl. .................................. 435/320.1
(58) Field of Classification Search ..................... None
See application file for complete search history.

(56) References Cited

U.S. PATENT DOCUMENTS

| 5,484,719 | A | * | 1/1996 | Lam et al. | ................... | 800/292 |
| 5,576,198 | A | * | 11/1996 | McBride et al. | ........... | 435/91.3 |
| 5,877,402 | A | * | 3/1999 | Maliga et al. | ............... | 800/298 |
| 5,914,123 | A | | 6/1999 | Arntzen et al. | | |

FOREIGN PATENT DOCUMENTS

| WO | WO 99/10513 | * | 3/1999 |
| WO | WO 99/10513 A1 | | 3/1999 |
| WO | WO 00/03022 A3 | | 1/2000 |
| WO | WO 01/72959 A2 | | 10/2001 |

OTHER PUBLICATIONS

Daniell et al, Aug. 2001, J. Mol. Biol. 311:1001-1009.*
Alpeter, F. et al. "Accelerated Production of Transgenic Wheat (*Triticum aestivum* L.) Plants" *Plant Cell Rep.* 1996, pp. 12-17, Vol. 16.
Alpeter, F. et al. "Rapid Production of Transgenic Turfgrass (*Festuca rubra* L.) Plants", *J. Plant Physiol.* 2000, pp. 441-448, Vol. 157.
Joellenbech, L. M. et al. "Anthrax Vaccine Manufacture", *The Anthrax Vaccine Is it Safe?*, 2002, pp. 180-197.
Millan, A. F., et al. "A Chloroplast Transgenic Approach to Hyper-Express and Purify Human Serum Albumin, a Protein Highly Susceptible to Proteolytic Degradation", *Plant biotechnology Journal*, 2003, pp. 71-79, vol. 1.
Petrides, D. et al. "Computer-Aided process analysis and economic evaluation of for biosynthetic human insulin production" *Biotechnology and Bioengineering*, 1995, pp. 529-554, vol. 48, No. 1.
Sugita, M. et al. "Regulation of gene expression in chloroplasts of higher plants" *Plant Mol. Biol.*, Oct. 1996, pp. 315-326, vol. 32, No. 1-2.
Williamson, E.D. et al. "Local and Systemic immune response to a microencapsulated sub-unit vaccine for plague" Vaccine, Dec. 1996, pp. 1613-1619, vol. 14, No. 17-18.
Gordon-Kamm, W. J. et al. "Transgenic Cereals—*Zea mays* (Maize)", *Molecular Improvements of Ceral Crops*, 1999, pp. 189-253, Kluwer Academic Publishers, Great Britain, I.K. Vasil (ed.).
Aziz, M.A. et al. "Expression of protective antigen in transgenic plants: a step towards edible vaccine against anthrax" *Biochemical and Biophysical Research Communications*, Dec. 6, 2002, pp. 345-351, vol. 299, No. 3.
Grevich, J. et al. "Chloroplast genetic engineering: Recent advances and future perspectives" *Critical Reviews in Plant Sciences*, 2005, pp. 83-107, vol. 24, No. 2.
Watson, J. et al. "Expression of *Bacillus anthracis* protective antigen in transgenic chloroplasts towards the development of an improved vaccine or an edible vaccine" from the 10th IAPTCB Conference: Congress on In Vitro Biology, Jun. 2002, pp. 64-A, Orlando, Florida. Abstract only.
Watson, J. et al. "Expression of *Bacillus anthracis* protective antigen in transgenic chloroplasts of tobacco, a non-food/deed crop" *Vaccine*, pp. 4374-4384 , Oct. 22, 2004, vol. 22, No. 31-32.
Ahuja, N. et al. "Rapid Purification of Recombinant Anthrax-Protective Antigen under Nondenaturing Conditions" *Biochemical and Biophysical Research Communications*, 2001, pp. 6-11, vol. 286.
Altpeter, F. et al. "Generation Of Large Numbers Of Independently Transformed Fertile Perennial Ryegrass (*Lolium perenne* L.) Plants Of Forage- And Turf Cultivars" *Mol. Breeding*, 2000, pp. 519-528, vol. 6.
Altpeter, F. et al. "Integration And Expression Of The High-Molecular-Weight Gluteni Subunit 1Ax1 Gene Into Wheat" *Nat. Biotechnol.*, Sep. 1996, pp. 1155-1159, vol. 14, No. 9.
Anderson, G. W. Jr. et al. "Recombinant V Antigen Protects Mice against Pneumonic and Bubonic Plague Caused by F1-Capsule-Positive and -Negative Strains of *Yersinia pestis*" *Infection and Immunity*, Nov. 1996, pp. 4580-4585, vol. 64, No. 11.
Andrews, G. P. et al. "Protective Efficacy of Recombinant *Yersinia* Outer Proteins against Bubonic Plague Caused by Encapsulated and Nonencapsulated *Yersinia pestis*" *Infection and Immunity*, Mar. 1999, pp. 1533-1537, vol. 67, No. 3.

(Continued)

*Primary Examiner*—Anne Kubelik
(74) *Attorney, Agent, or Firm*—Saliwanchik, Lloyd & Saliwanchik

(57) ABSTRACT

Vectors and methods for plastid transformation of plants to produce protective antigens and vaccines for oral delivery are provided. The invention provides edible vaccines for conferring immunity to a mammal against *Bacillus anthracis*, as well as *Yersina pestis*.

2 Claims, 21 Drawing Sheets

OTHER PUBLICATIONS

Figure 1A:
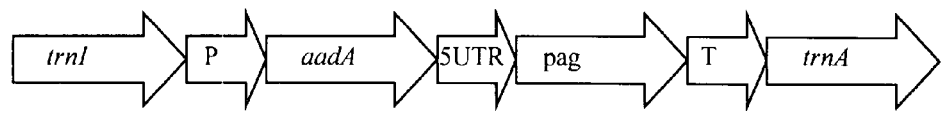
Figure 1B:
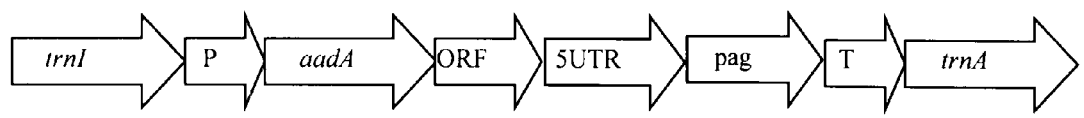
Figure 1C:
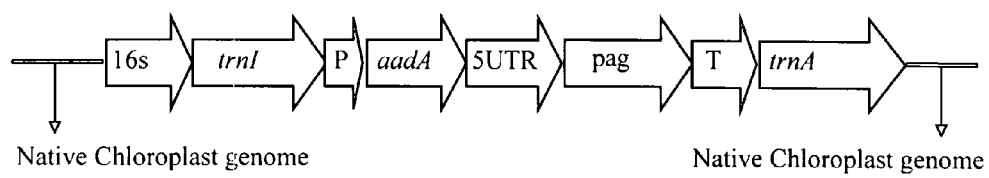
Figure 1D:
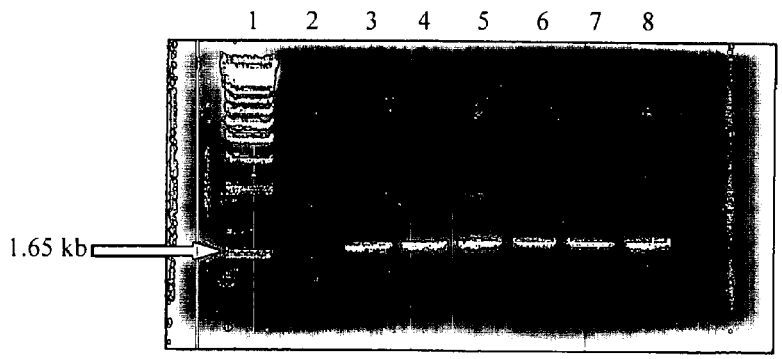
Figure 2A:
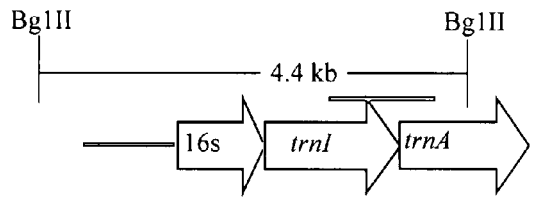
Figure 2B:
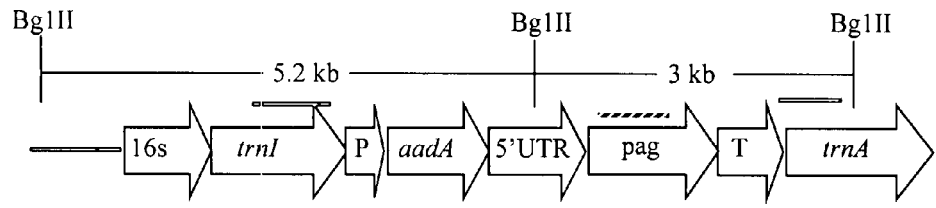
Figure 2C:
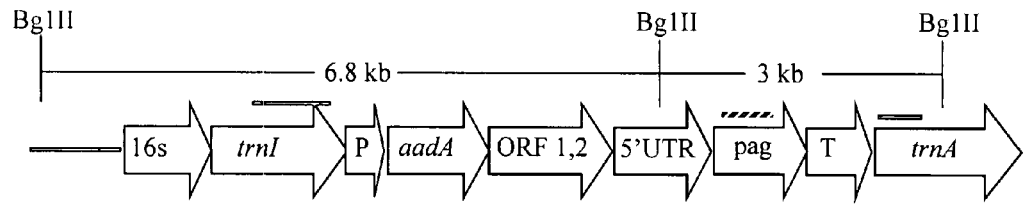
Figure 2D:
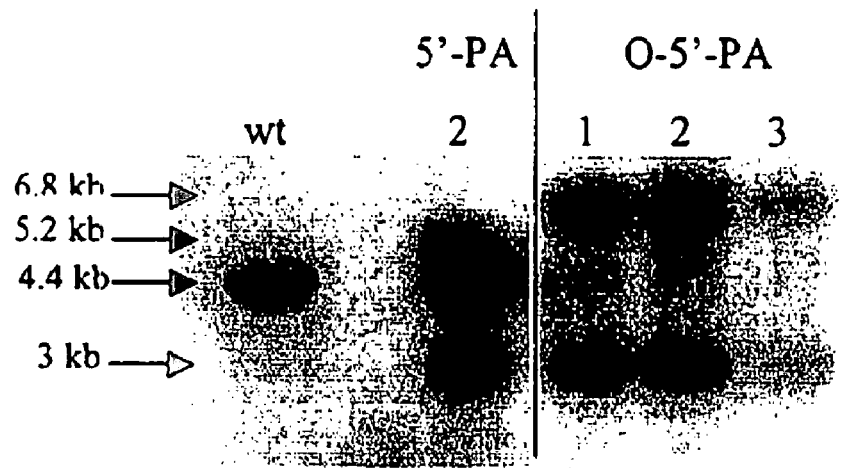
Figure 2E:
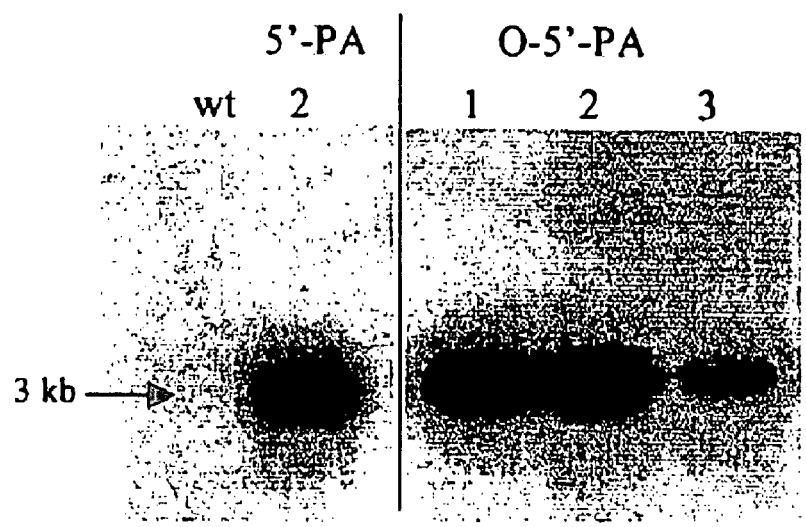

Arakawa, T. et al. "Expression of cholera toxin B subunit oligomers in transgenic potato plants" *Transgenic Research*, 1997, pp. 403-413, vol. 6.

Baillie, L. "The development of new vaccines against *Bacillus anthracis*" *Journal of Applied Microbiology*, 2001, pp. 609-613, vol. 91.

Beck L. R. et al. "A new long-acting injectable microcapsule system for the administration of progesterone" May 1979, pp. 545-551, vol. 31, No. 5.

Belyakov, I. M. et al. "Interplay of Cytokines and Adjuvants in the Regulation of Mucosal and Systemic HIV-Specific CTL" *The Journal of Immunology*, 2000, pp. 6454-6462, vol. 165.

Berneman, A. et al. "The Specificity Patterns of Human Immunoglobulin G Antibodies in Serum Differ from Those in Autologous Secretions" *Infection and Immunity*, Sept. 1998, pp. 4163-4168, vol. 66, No. 9.

Bhatnagar, R. et al. "Calcium Is Required for the Expression of Anthrax Lethal Toxin Activity in the Macrophagelike Cell Line J774A.1" *Infection and Immunity*, Jul. 1989, pp. 2107-2114, vol. 57, No. 7.

Bocci, V. "The Oropharyngeal Delivery of Interferons: Where Are We and Where Do We Need to Go?" *Journal of Interferon and Cytokine Research*, 1999, pp. 859-861, vol. 19.

Bockman De et al. "Pinocytosis by epithelium associated with lymphoid follicles in the bursa of Fabricius, appendix, and Peyer's patches. An electron microscopic study" *American Journal of Anatomy*, Apr. 1973, pp. 455-477, vol. 136, No. 4.

Bouvet, J. P. et al. "Stimulation of local antibody production: parenteral or mucosal vaccination?" *Trends in Immunology*, Apr. 2002, pp. 209-213, vol. 23, No. 4.

Bouvet, J. P. et al. "Diversity of Antibody-Mediated Immunity at the Mucosal Barrier" *Infection and Immunity*, Jun. 1999, pp. 2687-2691, vol. 67, No. 6.

Bradley, K. A. et al. "Identification of the cellular receptor for anthrax toxin" *Nature*, Nov. 8, 2001, pp. 225-229, vol. 414.

Brossier, F. et al. "Role of Toxin Functional Domains in Anthrax Pathogenesis" *Infection and Immunity*, Apr. 2000, pp. 1781-1786, vol. 68, No. 4.

Cárdenas-Freytag, L. et al. "Effectiveness of a Vaccine Composed of Heat-Killed *Candida albicans* and a Novel.Mucosal Adjuvant, LT(R192G), against Systemic Candidiasis" *Infection and Immunity*, Feb. 1999, pp. 826-833, vol. 67, No. 2.

Castañon, S. et al. "Immunization with Potato Plants Expressing VP60 Protein Protects against Rabbit Hemorrhagic Disease Virus" *Journal of Virology*, May 1999, pp. 4452-4455, vol. 73, No. 5.

Chauhan, V. et al. "Constitutive Expression of Protective Antigen Gene of *Bacillus anthracis* in *Escherichia coli*" *Biochemical and Biophysical Research Communications*, 2001, pp. 308-315, vol. 283.

Cho, M. -J. et al. "Production Of Transgenic Tall Fescue And Red Fescue Plants By Particle Bombardment Of Mature Seed-Derived Highly Regenerative Tissues" *Plant Cell Rep.* 2000, pp. 1084-1089.

Choi, A. H. C. et al. "Antibody-Independent Protection against Rotavirus Infection of Mice Stimulated by Intranasal Immunization with Chimeric VP4 or VP6 Protein" *Journal of Virology*, Sep. 1999, pp. 7574-7581, vol. 73, No. 9.

Choi, A. H. C. et al. "Functional Mapping of Protective Domains and Epitopes in the Rotavirus VP6 Protein" *Journal of Virology*, Dec. 2000, pp. 11574-11580, vol. 74, No. 24.

Chong C. et al. "LT(R192G), a non-toxic mutant of the heat-labile enterotoxin of *Escherichia coli*, elicits enhanced humoral and cellular immune responses associated with protection against lethal oral challenge with *Samonella* spp." *Vaccine*, 1998, pp. 732-740, vol. 16, No. 7.

Coulson, N. M. et al. "*Bacillus anthracis* protective antigen, expressed in *Salmonella typhimurium* SL 3261, affords protection against anthrax spore challenge" *Vaccine*, Nov. 1994, pp. 1395-1401, vol. 12, No. 15.

Cramer, C. L. et al. "Transgenic plants for therapeutic proteins: linking upstream and downstream strategies" *Current Topics Microbiol. Immunol.*, 1999, pp. 95-118, vol. 240.

Cummins, J. M. et al. "Oral Use of Interferon" *Journal of Interferon and Cytokine Research*, 1999, pp. 853-857, vol. 19.

Daniell, H. "Foreign gene expression in chloroplasts of higher plants mediated by tungsten particle bombardment" *Methods Enzymol.*, 1993, pp. 536-556, vol. 217.

Daniell, H. "Transformation and foreign gene expression in plants by microprojectile bombardment" *Methods Mol. Biol.*, 1997, pp. 463-489, vol. 62.

Daniell, H. et al. "Containment of herbicide resistance through genetic engineering of the chloroplast genome" *Nature Biotechnology*, Apr. 1998, pp. 345-348, vol. 16, No. 4.

Daniell, H. et al. "Milestones in chloroplast genetic engineering: an environmentally friendly era in biotechnology" *Trends in Plant Science*, Feb. 2002, pp. 84-91, vol. 7, No. 2.

Daniell, H. et al. "Expression of the Native Cholera Toxin B Subunit Gene and Assembly as Functional Oligomers in Transgenic Tobacco Chloroplasts" *Journal of Mol. Biol.*, 2001, pp. 1001-1009, vol. 311.

Daniell, H. et al. "Marker free transgenic plants: engineering the chloroplast genome without the use of antibiotic selection" *Curr. Genet.*, 2001, pp. 109-116, vol. 39.

Daniell, H. et al. "Medical molecular farming: production of antibodies, biopharmaceuticals and edible vaccines in plants" *Trends in Plant Science*, May 2001, pp. 219-226, vol. 6, No. 5.

Daniell, H. et al. "An efficient and prolonged in vitro translational system from isolated cucumber etioplasts" *Biochem. Biophys. Res. Commun.*, Feb. 26, 1986, pp. 248-255, vol. 135, No. 1.

Daniell, H. et al. "Uptake and expression of bacterial and cyanobacterial genes by isolated cucumber etioplasts" *Proc. Natl. Acad. Sci. USA*, Sep. 1987, pp. 6349-6353, vol. 84.

Daniell, H. et al. "In vitro synthesis of photosynthetic membranes: I. Development photosystem I activity and cyclic photophosphorylation" *Biochem. Biophys. Res. Commun.*, Mar. 16, 1983, pp. 740-749, vol. 111, No. 2.

Daniell, H. et al. "Transient foreign gene expression in chloroplasts of cultured tobacco cells after biolistic delivery of chloroplast vectors" *Proc. Natl. Sci. USA*, Jan. 1990, vol. 87, No. 1.

Daniell, H. "Molecular strategies for gene containment in transgenic crops" *Nature Biotechnology*, Jun. 2002, pp. 581-586, vol. 20.

Daniell, H. et al. "Chloroplast culture. IX. Chlorophyll(ide) a biosynthesis in vitro rates higher than in vivo" *Biochem. Biophys. Res. Commun.*, May 31, 1982, pp. 466-470, vol. 106, No. 2.

De Cosa, B. et al. "Overexpression of the *Bt cry2* Aa2 operon in chloroplasts leads to formation of insecticidal crystals" *Nature Biotechnology*, Jan. 2001, pp. 71-74, vol. 19.

De Gray, G. et al. "Expression of an Antimicrobial Peptide via the Chloroplast Genome to Control Phytopathogenic Bacteria and Fungi" *Plant Physiology*, Nov. 2001, pp. 852-862, vol. 127.

Dixon, T. C. et al. "Anthrax" *The New England Journal of Medicine*, Sep. 9, 1999, pp. 815-826, vol. 341, No. 11.

Drum, C. L. et al. "Structural basis for the activation of anthrax adenylyl cyclase extoxin by calmodulin" *Nature*, Jan. 24, 2002, pp. 396-402, vol. 415.

Edwards, K. et al. "A simple and rapid method for the preparation of plant genomic DNA for PCR analysis" *Nucleic Acids Research*, Jan. 2, 1991, pp. 1349, vol. 19, No. 6.

Eyles, J. E. et al. "Analysis of local and systemic immunological responses after intra-tracheal, intra-nasal and intra-muscular administration of microsphere co-encapsulated *Yersinia pestis* sub-unit vaccines" Vaccine, 1998, pp. 2000-2009, vol. 16, No. 20.

Eyles, J. E. et al. "Generation of protective immune responses to plague by mucosal administration of microsphere coencapsulated recombinant subunits" *Journal of Controlled Release*, 2000, pp. 191-200, vol. 63.

Fang, Y.D. et al. "Agrobacterium-mediated barley (*Hordeum vulgare* L.) transformation using green fluorescent protein as a visual marker and sequence analysis of the T-DNA: barley genomic DNA Junctions", *J. Plant Physiol*, 2002, pp. 1131-1138, vol. 159.

Freytag, L. C. et al. "Bacterial toxins as mucosal adjuvants" *Curr. Top. Microbiol. Immunol.*, 1999, pp. 215-236, vol. 236.

Ge, B. et al. "Differential effects of helper proteins encoded by the *cry2A* and *cry11A* operons on the formation of Cry2A inclusions in *Bacillus thuringiensis*" *FEMS Microbiology Letters*, 1998, pp. 35-41, vol. 165.

Gerber, S. et al. "Human Papillomavirus Virus-Like Particles Are Efficient Oral Immunogens when Coadministered with *Escherichia coli* Heat-Labile Enterotoxin Mutant R192G or CpG DNA" *Journal of Virlogy*, May 2001, pp. 4752-4760, vol. 75, No. 10.

Gu, M. L. et al. "Protection against anthrax toxin by vaccination with a DNA plasmid encoding anthrax protective antigen" *Vaccine*, 1999, pp. 340-344, vol. 17.

Guillobel, H. C. et al. "Adjuvant Activity of a Nontoxic Mutant of *Escherichia coli* Heat-Labile Enterotoxin on Systemic and Mucosal Immune Responses Elicited against a Heterologus Antigen Carried by a Live *Salmonella enterica* Serovar Typhimurium Vaccine Strain" *Infection and Immunity*, Jul. 2000, pp. 4349-4353, vol. 68, No. 7.

Hanna, P. C. et al. "On the role of macrophages in anthrax" *Proc. Natl. Acad. Sci. USA*, Nov. 1993, pp. 10198-10201, vol. 90.

Haq, T. A. et al. "Oral Immunization with a recombinant bacterial antigen produced in transgenic plants" *Science*, May 5, 1995, pp. 714-716, vol. 268, No. 5211.

Heath, D. G. et al. "Protection against experimental bubonic and pneumonic plague by recombinant capsular F1-V antigen fusion protein vaccine" *Vaccine*, Jul. 1998, pp. 1131-1137, vol. 16, No. 11-12.

Hill, J. et al. "Region of *Yersinia pestis* V Antigen that Contribute to Protection against Plague identified by Passive and Active Immunization" *Infection and Immunity*, Nov. 1997, pp. 4476-4482, vol. 65, No. 11.

Holmgren, J. et al. "Cholera toxin in cholera B subunit as oral-muscosal adjuvant and antigen vector systems" *Vaccine*, Sep. 1993, pp. 1179-1184, vol. 11, No. 12.

Inglesby, T. V. MD et al. "Anthrax as a Biological Weapon" *JAMA*, May 12, 1999, pp. 1735-1745, vol. 281, No. 18.

Ivins, B. et al. "Experimental anthrax vaccines: efficacy of adjuvants combined with protective antigen against an aerosol *Bacillus anthracis* spore challenge in guinea pigs" *Vaccine*, 1995, pp. 1779-1784, vol. 13, No. 18.

Ivins, B. et al. "Comparative Effecacy of Experimental Anthrax Vaccine Candidate Against Inhalation Anthrax in Rhesus Macaques" *Vaccine*, 1998, pp. 1141-1148, vol. 16, No. 11-12.

Jones, S. M. et al. "Protection conferred by a fully recombinant sub-unit vaccine against *Yersinia pestis* in male and female mice of four inbred strains" *Vaccine*, 2001, pp. 358-366, vol. 19.

Kapusta, J. et al. "A plant-derived edible vaccine against hepatitis B virus" *FASEB J.*, 1999, pp. 1796-1799, vol. 13.

Kaufmann, A. F. et al. "The economic impact of a bioterrorist attack: are prevention and postattack intervention programs justifiable?" *Emerging Infectious Disease*, 1997, pp. 83-94, vol. 3, No. 2.

Klimpel, K. R. et al. "Anthrax toxin protective antigen is activated by a cell surface protease with the sequence specificity and catalytic properties of furin" *Proc. Natl. Acad. Sci. USA*, Nov. 1992, pp. 10277-10281, vol. 89.

Koo, M. et al. "Protective immunity against murine hepatitis virus (MHV) induced by intranasal or subcutaneous administration of hybrids of tobacco mosaic virus that carries an MHV epitope" *Proc. Natl. Acad. USA*, Jul. 1999, pp. 7774-7779, vol. 96.

Kota, M. et al. "Overexpression of the *Bacillus thuringiensis* (Bt) Cry2Aa2 protein in chloroplasts confers resistance to plants against susceptible and Bt-resistant insects" *Proc. Natl. Acad. Sci. USA*, Mar. 1999, pp. 1840-1845, vol. 96.

Kotloff, K. L. et al. "Safety and Immunogenicity of Oral Inactivated Whole-Cell *Helicobacter pylori* Vaccine with Adjuvant among Volunteers with or without Subclinical Infection" *Infection and Immunity*, Jun. 2001, pp. 3581-3590, vol. 69, No. 6.

Kusnadi, A. et al. "Production of Recombinant Proteins in Transgenic plants: Practical Considerations" *Biotechnology and Bioengineering*, 1997, pp. 473-484, vol. 56, No. 5.

Leary, S. E. C. et al. "Expression of an F1/V fusion protein in attenuated *Salmonella typhumurium* and protection of mice against plague" *Microbial Pathogenesis*, 1997, pp. 167-179, vol. 23.

Lencer, W. I. et al. "Transcytosis of cholera toxin subunits across model human intestinal epithelia" *Proc. Natl. Acad. Sci. USA*, Oct. 1995, pp. 10094-10098, vol. 92.

Leppla S. H. et al. "Development of an improved vaccine for anthrax" *J. Clin. Invest.*, 2002, pp. 141-144, vol. 109.

Mason, H. S. et al. "Expression of Norwalk virus capsid protein in transgenic tobacco and potato and its oral immunogenicity in mice" *Proc. Natl. Acad. Sci. USA*, May 1996, pp. 5335-5340, vol. 93.

Mason H. S. et al. "Edible vaccine protects mice against *Escherichia coli* heat-labile enterotoxin (LT): potatoes expressing a synthetic LT-B gene" *Vaccine*, 1998. pp. 1336-1343, vol. 16, No. 13.

Mathiowitz, E. et al. "Biologically erodable microspheres as potential oral drug delivery systems" Nature, Mar. 27, 1997, pp. 410-414, vol. 386, No. 6623.

McBride, K. E. et al. "Amplification of a chimeris *Bacillus* gene in choloroplasts leads to extraordinary level of an insecticidal protein in tobacco" *Biotechnology*, Apr. 1995, pp. 362-365, vol. 13, No. 4.

McCluskie, M. J. et al. "Mucosal immunization of mice using CpG DNA and/or mutants of the heat-labile enterotoxin of *Escherichia coli* as adjuvants" *Vaccine*, 2001, pp. 3759-3768, vol. 19.

McNeal, M. M. et al. "Antibody-Dependent and -Independent Protection following Intranasal Immunization of Mice with Rotavirus Particles" *Journal of Virology*, Sep. 1999, pp. 7565-7573, vol. 73, No. 9.

MMWR, et al. "Use of anthrax vaccine in the United States" *Recommendations of the Advisory Committee on Immunization Practices*, Dec. 15, 2000, pp. 1-20, vol. 49, No. RR15.

Molloy, S. S. et al. "Human Furin Is a Calcium-dependent Serine Endoprotease That Recognizes the Sequence Arg-X-X-Arg and Efficiently Cleaves Anthrax Toxin Protective Antigen" *The Journal of Biological Chemistry*, Aug. 15, 1992, pp. 16396-16402, vol. 267, No. 23.

Mor, T. S. et al. "Perspective: edible vaccines—a concept coming of age" *Trends in Microbiology*, Nov. 1998, pp. 449-453, vol. 6, No. 11.

Moriya, O. et al. "Induction of hepatitis C virus-specific cytotoxic T lymphocytes in mice by immunization with dendritic cells treated with an anthrax toxin fusion protein" *Vaccine*, 2002, pp. 789-796, vol. 20.

Morris, C. B. et al. "Effectiveness of intranasal immunization with HIV-gp160 and an HIV-1 Env CTL epitope peptide (E7) in combination with the mucosal adjuvant LT(R192G)" *Vaccine*, 2000, pp. 1944-1951, vol. 18.

Nicolson, G. et al. "Anthrax Vaccine: Controversy Over Safety and Efficacy", *Antimicrobics and Infectious Diseases Newsletter*, 2000, pp. 1-6, vol. 1.

O'Neal, C. M. et al. "Rotavirus 2/6 Viruslike Particles Administered Intranasally with Cholera Toxin, *Escherichia coli* Heat-Labile Toxin (LT), and LT-R192G Induce Protection from Rotavirus Challenge" *Journal of Virology*, Apr. 1998, pp. 3390-3393, vol. 72, No. 4.

Owen, R. L. et al. "M cell transport of *Vibrio cholerae* from the intestinal lumen into Peyer's patches: a mechanism for antigen sampling and for microbial transepithlial migration" *J. Intect. Dis.*, Jun. 1986, pp. 1108-1118, vol. 153, No. 6.

Oyston, P. C. et al. "An aroA mutant of *Yersinia pestis* is attenuated in guinea-pigs, but virulent in mice" *Microbiology*, Jul. 1996, pp. 1847-1853, vol. 142, Pt. 7.

Pannifer, A. D. et al. "Crystal structure of the anthrax lethal factor" *Nature*, Nov. 8, 2001, pp. 229-223, vol. 414.

Petosa C. et al. "Crystal structure of the anthrax toxin protective antigen" *Nature*, Feb. 27, 1997, pp. 833-838, vol. 385, No. 6619.

Pezard, C. et al. "Protective Immunity Induced by *Bacillus anthracis* Toxin-Deficient Strains" *Infection and Immunity*, Apr. 1995, pp. 1365-1372, vol. 63, No. 4.

Price, B. M. et al. "Protection against Anthrax Lethal Toxin Challenge by Genetic Immunization with a Plasmid Encoding the Lethal Factor Protein" *Infection and Immunity*, Jul. 2001, pp. 4509-4515, vol. 69, No. 7.

Purvis; I. J. et al. "The efficiency of folding of some proteins increased by controlled rates of translation in vivo" *J. Mol. Biol.*, Jan. 20, 1987, pp. 413-417, vol. 193, No. 2.

Ramirez, D. M. et al. "Production, recovery and immunogenicity of the protective antigen from a recombinant strain of *Bacillus anthracis" Journal of Industrial Microbiology & Biotechnology*, 2002, pp. 232-238, vol. 28.

Ruf, S. et al. "Stable genetic transformation of tomato plastids and expression of a foreign protein in fruit" *Nature Biotechnology*, Sep. 2001, pp. 870-875, vol. 19.

Russell, P. et al. "A comparison of Plague vaccine, USP and EV76 vaccine induced protection against *Yersinia pestis* in a murine model" *Vaccine*, 1995, pp. 1551-1556, vol. 13, No. 16.

Ryan, E. T. et al. "In Vivo Expression and Immunoadjuvancy of a Mutant of Heat-Labile Enerotoxin of *Escherichia coli* in Vaccine and Vector Strains of *Vibrio cholerae*" *Infection and Immunity*, Apr. 1999, pp. 1694-1701, vol. 67, No. 4.

Sabhnani, L. et al. "Identification of immunodominant epitope of F1 antigen of *Yersinia pestis*" *FEMS Immunology and Medical Microbiology*, 2000, pp. 155-162, vol. 27.

Sanford, J. C. et al. "Optimizing the biolistic process for different biological applications" *Methods Enzymol.*, 1993, pp. 483-509, vol. 217.

Scharton-Kersten, T. et al. "Transcutaneous Immunization with Bacterial ADP-Ribosylating Exotoxins, Subunits, and Unrelated Adjuvants" *Infection and Immunity*, Sep. 2000, pp. 5306-5313, vol. 68, No. 9.

Sestak, K. et al. "Active immunity and T-cell populations in pigs intraperitoneally inoculated with baculovirus-expressed transmissible gastroenteritis virus structural proteins" *Vet. Immunol. Immunopathol.*, Sep. 20, 1999, pp. 203-221, vol. 70.

Sidorov, V. A. et al. "Stable chloroplast transformation in potato: use of green flourescent protein as a plastid marker" *The Plant Journal*, 1999, pp. 209-216, vol. 19, No. 2.

Singh, Y. et al. "Study of Immunization against Anthrax with the Purified Recombinant Protective Antigen of *Bacillus anthracis*" *Infection and Immunity*, Jul. 1998, pp. 3447-3448, vol. 66, No. 7.

Staub, J. M. et al. "High-yield production of a human therapeutic protein in tobacco chloroplasts" *Nature Biotechnology*, Mar. 2000, pp. 333-338, vol. 18.

Straley, S. C. et al. "Virulence genes regulated at the tanscriptional level by Ca+2 in *Yersinia pestis* include structural genes for outer membrane proteins" *Infect. Immun.*, 1996, pp. 445-454, vol. 51.

Streatfield, S. J. et al. "Plant-based vaccines: unique advantages" *Vaccine*, 2001, pp. 2742-2748, vol. 19.

Svab, Z. et al. "High-frequency plastid transformation in tobacco by selection for a chimeric *aadA* gene" *Proc. Natl. Acad. Sci. USA*, Feb. 1993, pp. 913-917, vol. 90.

Tacket, C. O. et al. "Safety of Live Oral *Salmonella typhi* Vaccine Strains with Deletions in *htrA* and *aroC aroD* and Immune Response in Humans" *Infection and Immunity*, Feb. 1997, pp. 452-456, vol. 65, No. 2.

Tacket, C. O. et al. "Immunogenicity in humans of a recombinant bacterial antigen delivered in a transgenic potato" *Nat. Med.* May 1998, pp. 607-609, vol. 4, No. 5.

Titball, R. W. et al. "Vaccination against bubonic and pneumonic plague" *Vaccine*, 2001, pp. 4175-4184, vol. 19.

Tuboly, T. et al. "Immunogenicity of porcupine transmissible gastroenteritis virus spike protein expressed in plants" *Vaccine*, 2000, pp. 2023-2028, vol. 18.

Tumpey, T. M. et al. "Mucosal Delivery of Inactivated Influenza Vaccine Induces B-Cell-Dependent Heterosubtypic Cross-Protection against Lethal Influenza A H5N1 Virus Infection" *Journal of Virology*, Jun. 2001, pp. 5141-5150, vol. 75, No. 11.

Varshney, A. et al. "Stable transformation and tissue culture response in current European winter wheat germplasm" *Mol. Breeding*, 2001, pp. 295-309, vol. 8.

Vasil, I. K. et al. "Evaluation of baking properties and gluten protein composition of field grown transgenic wheat lines expressing high molecular weight glutenin gene 1Ax1" *J. Plant Physiol* 2001, pp. 521-528, vol. 158.

Walmsley, A. M. et al. "Plants for delivery of edible vaccines" *Curr. Opin. Biotechnol.* Apr. 2000, pp. 126-129, vol. 11, No. 2.

Wesche, J. et al. "Characterization of Membrane Translocation by Anthrax Protective Antigen", *Biochemistry*, 1998, pp. 15737-15746, vol. 37.

Williamson, E. et al. "Modulating Dendritic Cells to Optimize Mucosal Immunization Protocols" *Journal of Immunology*, 1999, pp. 3668-3675, vol. 163.

Williamson, E. D. et al. "A sun-unit vaccine elicits IgG in serum, spleen cell cultures and bronchial washings and protects immunized animals against pneumonic plague" *Vaccine*, 1997, pp. 1079-1084, vol. 15, No. 10.

Williamson, E. D. et al. "A single dose sub-unit vaccine protects against pneumonic plague" *Vaccine*, 2001, pp. 566-571, vol. 19.

Williamson, E. D. et al. "An IgG1 titre to the F1 and V antigens with protection against plague in the mouse model" *Clin. Exp. Immunol.*, 1999, pp. 107-114, vol. 116.

Williamson, E. D. "Plague vaccine research and development" *Journal of Applied Microbiology*, 2001, pp. 606-608, vol. 91.

Xu, J. et al. "Dissection of RNA-mediated ryegrass mosaic virus resistance in fertile transgenic perennial ryegrass (*Lolium perenne* L.)" *The Plant Journal*, 2001, pp. 265-274, vol. 26, No. 3.

Ye, G. N. et al. "Optimization of delivery of foreign DNA into higher-plant chloroplasts" *Plant Mol. Biol.*, Dec. 1990, pp. 809-819, vol. 15, No. 6.

Yu, J. et al. "A plant-based multicomponent vaccine protects mice from enteric diseases" *Nature Biotechnology*, Jun 2001, pp. 548-552, vol. 19.

Yuan, L. et al. "Intranasal Administration of 2/6-Rotavirus-Like Particles with Mutant *Escherichia coli* Heat-Labile Toxin (LT-R192G) Induces Antibody-Secreting Cell Responses but Not Protective Immunity in Gnotobiotic Pigs" *Journal of Virology*, Oct. 2000, pp. 8843-8853, vol. 74, No. 19.

* cited by examiner

———— 0.81 kb Flanking Sequence Probe
▪▪▪▪▪▪▪▪ 0.52 kb *pag* Probe

———— 0.81 kb Flanking Sequence Probe
▪▪▪▪▪▪▪▪ 0.52 kb *pag* Probe pTOM-BADH2-G10-*pag* ~8.8 kb

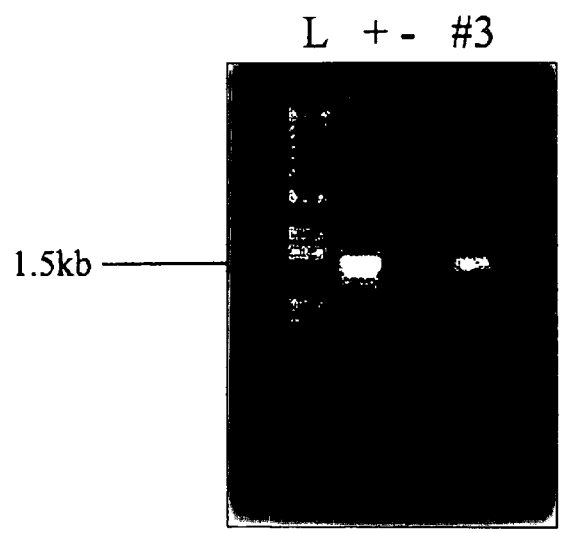
FIG. 8
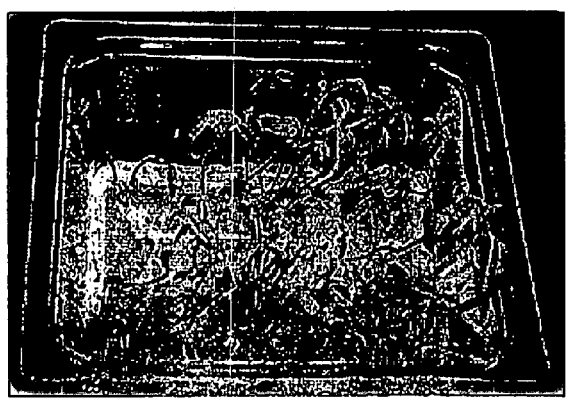 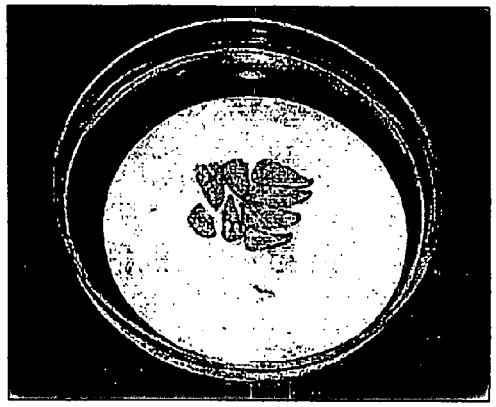
FIG. 9A  FIG. 9B

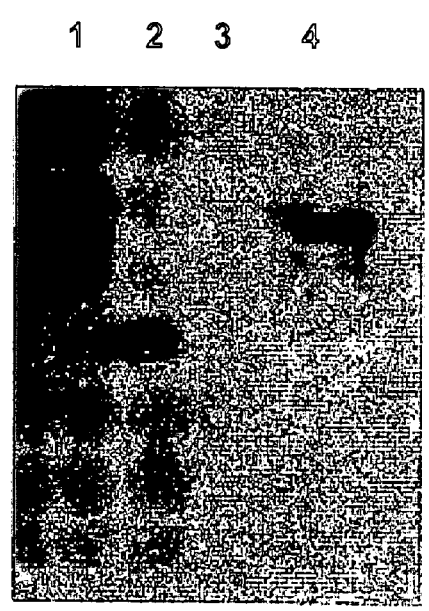
FIG. 15A                    FIG. 15B
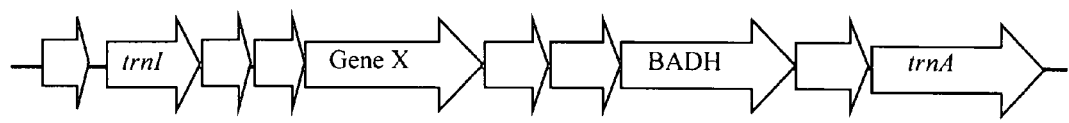
FIG. 16

Figure 17:
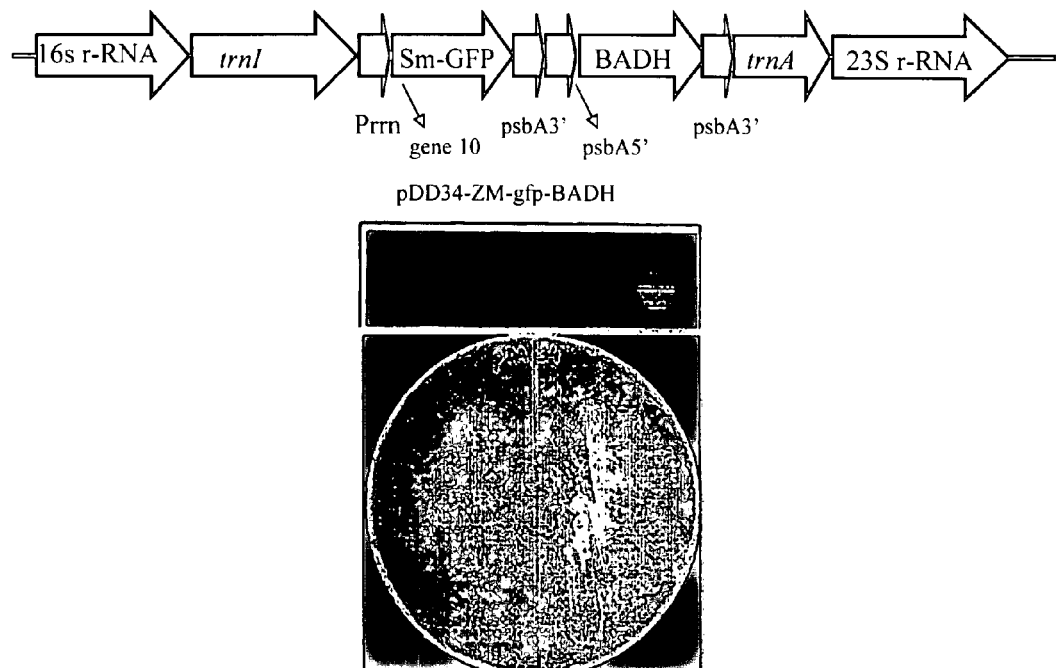
Figure 18:
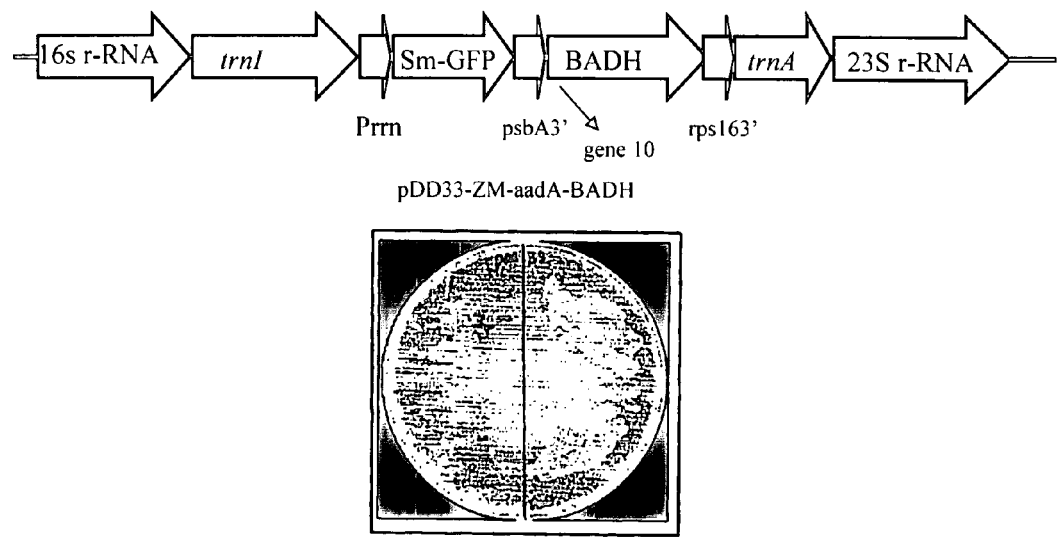

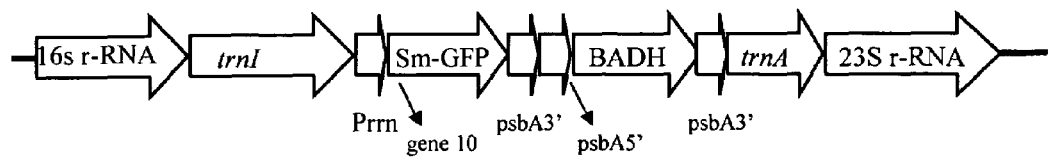
FIG. 17A  pDD34-ZM-gfp-BADH
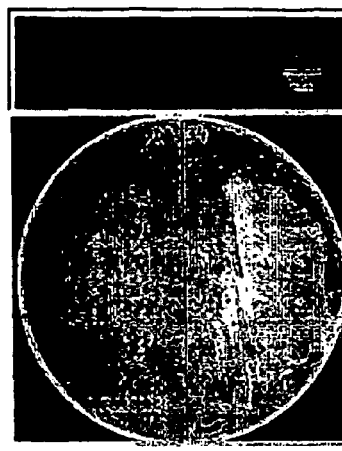
FIG. 17B
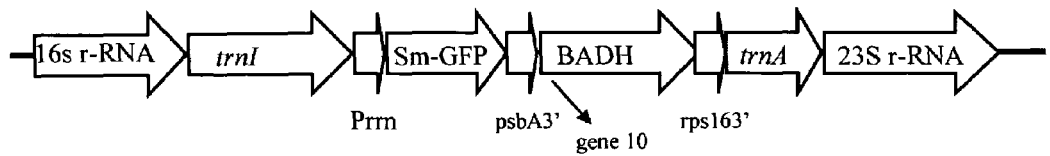
FIG. 18A  pDD33-ZM-aadA-BADH
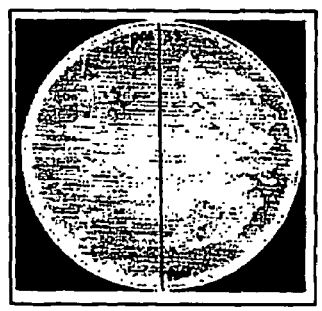
FIG. 18B

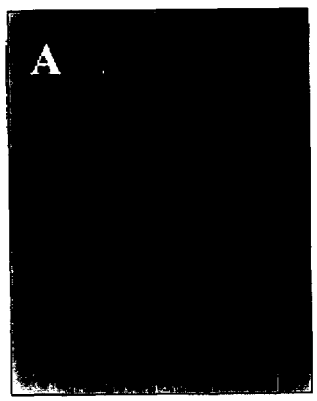 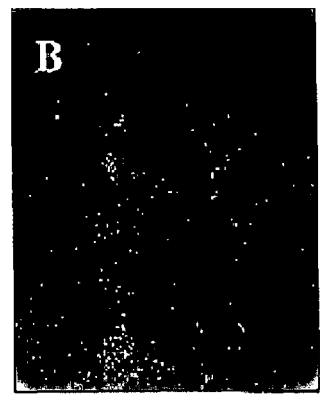 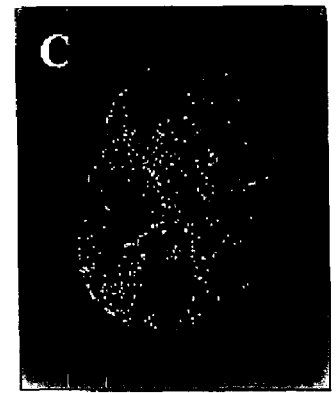
FIG. 19A  FIG. 19B  FIG. 19C
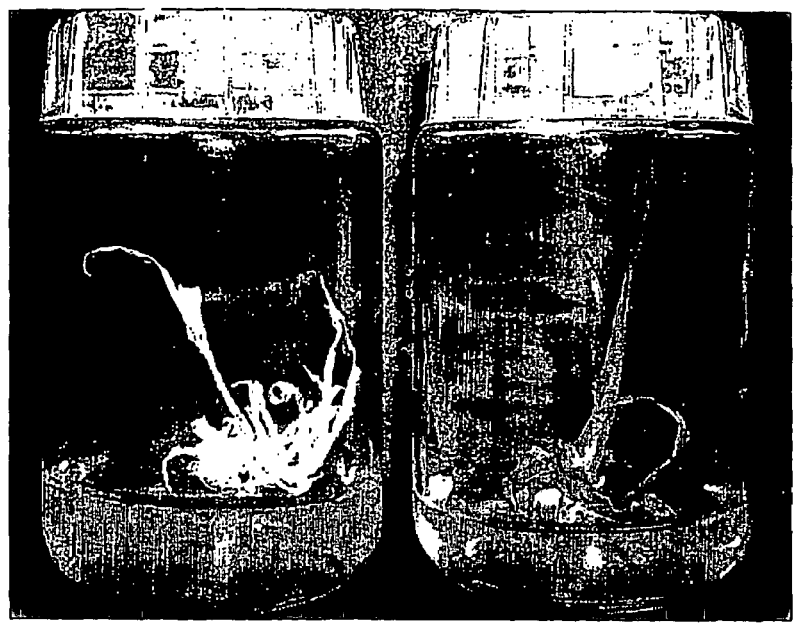
FIG. 20A

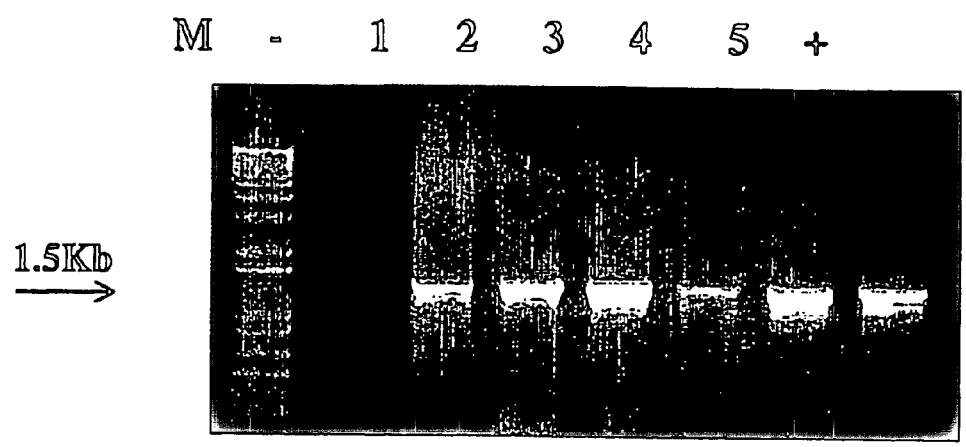
FIG. 20B
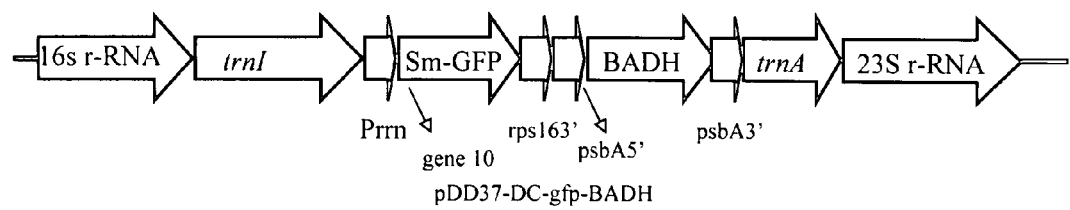
pDD37-DC-gfp-BADH
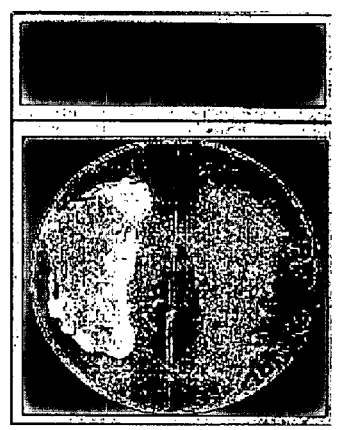
FIG. 21 pDD37-DC-gfp-BADH pDD36-DC-aadA-BADH

EXPRESSION OF PROTECTIVE ANTIGENS IN TRANSGENIC CHLOROPLASTS

BACKGROUND

Yersinia pestis is the causative agent of bubonic and pneumonic plague. Bacillus anthracis is the causative agent for the anthrax disease. The Centers for Disease Control and Prevention (hereinafter "CDC") lists *Y. pestis* and *B. anthracis* as two of the six Category A biological agents that pose a risk to national security.

*Yersinia pestis*

The etiologic agent of plague is the Gram-negative bacterium *Yersinia pestis*. The natural route of transmission of *Y. pestis* from one animal host to another is either directly or via a flea vector. Plague is endemic in some regions of the world and outbreaks occasionally occur as a consequence of natural disasters. *Y. pestis* is also a concern as one of the microorganisms with potential for use against civilian or military populations as a biological warfare/biological terrorism agent. In such a situation, the pneumonic form of plague would be the most likely outcome. This form of plague is particularly devastating because of the rapidity of onset, the high mortality, and the rapid spread of the disease. Immunization against aerosolized plague presents a particular challenge for vaccine developers. There is currently no vaccine for plague.

Both live attenuated and killed plague vaccines have been used in man, although questions remain about their safety and relative efficacy, especially against the pneumonic form of infection. Since plague remains endemic in some regions of the world, and because of the possibility of the illegitimate use of *Y. pestis* as a biological warfare agent, development of improved vaccines against plague is a high priority. The ideal vaccine should be deliverable in a minimum of doses and quickly produce high titer and long-lasting antibodies. Moreover, such a vaccine should protect against aerosolized transmission of *Y. pestis*.

The two most recently described approaches to development of improved plague vaccines are 1) attenuated mutants of *Y. pestis* and 2) subunit vaccines. The potential efficacy of attenuated mutants of *Y. pestis* as vaccines is supported by experience with the live attenuated vaccine strain EV76. This vaccine has been in use since 1908 and is given as a single dose Immunization of mice with EV76 induces an immune response and protects mice against subcutaneous and inhalation (aerosolized) infection. However, this vaccine strain is not avirulent and has an unacceptable safety profile. Moreover, multiple variants of the classical EV76 strain exist that differ significantly in passage history and genetic characteristics. Recent studies have focused on creating defined genetically attenuated mutants of *Y. pestis*, similar to those created in other Gram-negative bacteria (i.e., *Salmonella* spp.). For unknown reasons, genetic mutations, which markedly attenuate *Salmonella* spp. do not attenuate *Y. pestis*. For instance, an aroA mutant of *Y. pestis* was fully virulent in the murine model of disease but avirulent in guinea pigs.

A number of potential subunit vaccines have been evaluated for immunogenicity and protective efficacy against *Y. pestis*. The two most promising are F1 and V. F1 is a capsular protein located on the surface of the bacterium and the V antigen is a component of the *Y. pestis* Type III secretion system. These proteins have been produced recombinantly and induce protective immune responses when administered individually. A combination or fusion of F1 and V may have an additive protective effect when used to immunize humans against plague. It is thought that F1-V fusion protein should provide protection against both subcutaneous and aerosol challenge, and will have the potential to provide protective immunity against pneumonic as well as bubonic plague due to either wild type F1+ *Y. pestis* or to naturally occurring F1-variants. To date no one has been able to express the F1-V fusion protein in transgenic chloroplast. Such an accomplishment would provide a large supply of high-quality antigen for vaccines.

*Bacillus anthracis*

*Bacillus anthracis* is the organism that causes the anthrax disease. It is a Gram-positive, nonmotile, aerobic or facultatively anaerobic, spore-forming bacterium. The spores are about 1 μm in size, extremely hardy, resistant to gamma rays, UV light, drying, heat, and many disinfectants. Spores germinate upon entering an environment rich in glucose, amino acids, and nucleosides, such as in animal and human tissues and blood. The vegetative cells enter the spore state when the nutrients are exhausted or when the organisms are exposed to molecular oxygen in the air.

Anthrax is typically a disease of animals, especially herbivores such as cows, sheep, and goats. It affects humans through contact with the spores in one of three ways. Cutaneous anthrax occurs when the spores enter the body through a cut or an abrasion on the skin. Gastrointestinal anthrax occurs when the spores enters the body through consumption of contaminated meat products. Inhalation anthrax occurs when the spores enter the body through inhalation of the spores.

When spores enter the body, macrophages engulf them, migrate to regional lymph nodes and the spores germinate into vegetative bacteria. Macrophages release the vegetative bacteria and they spread through the blood and lymph until there are up to $10^8$ bacilli per milliliter of blood. The exotoxins are produced from bacteria and they lead to symptoms and possible death. Spores can survive in the lungs or lymph nodes up to 60 days before germination occurs. In animal experiments, it has been seen that once toxin secretion has reached a critical threshold, death will occur, even if the blood is rendered sterile through the use of antibiotics. From primate studies, the estimated lethal dose of inhaled anthrax spores sufficient to kill 50% of humans exposed to it (the LD50) is 2,500-55,000 spores.

The CDC lists anthrax as a category A disease agent and estimates the cost of an anthrax attack would be $26.2 billion per 100,000 persons exposed. The only vaccine licensed for human use in the U.S., Biothrax (formerly Anthrax vaccine adsorbed, or AVA), is an aluminum hydroxide-adsorbed, formalin-treated culture supernatant of a toxigenic, nonencapsulated, non-proteolytic strain of *Bacillus anthracis*. In addition to the immunogenic protective antigen (PA), the vaccine contains trace amounts of edema factor (EF) and lethal factor (LF) that may contribute to the local reactions seen in 5-7% of vaccine recipients, or reported to be toxic causing side-effects. There is a clear need and urgency for an improved vaccine for anthrax and for improved production methods that allow it to be mass-produced at reasonable cost.

There are two main virulence factors associated with *B. anthracis*, the polyglutamyl capsule which is believed to prevent the vegetative bacterial cells from being phagocytized and the exotoxins. Two different exotoxins are produced by three factors. PA binds to the host cell, LF is a zinc metalloprotease which inactivates mitogen-activated protein kinase. The edema toxin is formed when PA binds to EF.

This toxin increases cyclic AMP (cAMP) levels in the cell which upsets the water homeostasis resulting in accumulation of fluid called edema. The lethal toxin is formed from binding of PA and LF. This toxin stimulates macrophages to release interleukin-1b, tumor necrosis factor a, and other cytokines which contribute to shock and sudden death.

Anthrax has become a serious threat due to its potential use in bioterrorism and recent outbreaks among wild-life in the United States. Concerns regarding vaccine purity, the current requirement for six injections followed by yearly boosters, and a limited supply of the key protective antigen (PA), underscore the urgent need for an improved vaccine.

SUMMARY OF THE INVENTION

The present invention pertains to vaccines for conferring immunity in mammals to infective pathogens, as well as vectors and methods for plastid transformation of plants to produce protective antigens and vaccines for oral delivery. The invention further provides transformed plastids having the ability to survive selection in both the light and the dark, at different developmental stages by using genes coding for two different enzymes capable of detoxifying the same selectable marker, driven by regulatory signals that are functional in proplastids as well as in mature chloroplasts. The invention utilizes antibiotic-free selectable markers to provide edible vaccines for conferring immunity to a mammal against *Bacillus anthracis*, as well as *Yersina pestis*. The vaccines are operative by parenteral administration as well. The invention also extends to the transformed plants, plant parts, and seeds and progeny thereof. The invention is applicable to monocot and dicot plants.

BRIEF DESCRIPTION OF THE FIGURES

FIG. 1 is a schematic view of anthrax chloroplast constructs according to the present invention, and a view of a southern blot. FIG. 1A shows the pLD-JW1 vector used for chloroplast transformation. FIG. 1B shows the pLD-JW2 construct. FIG. 1C shows PCR with the primers 3P and 3M. FIG. 1D shows a PCR analysis of randomly selected clones.

FIG. 2 is a schematic view of anthrax chloroplast constructs according to the present invention, and views of southern blots. FIG. 2A shows expected products from digestion of wild type untransformed plant. FIG. 2B shows expected products from digestion of a plant transformed with pLD-JW1. FIG. 2C shows expected products from digestion of a plant transformed with pLD-JW2. FIG. 2D shows a flanking sequence probe showing heteroplasmy in pLD-JW1 line and homoplasmy in pLD-JW2 lines. FIG. 2E shows a pag sequence probe showing presence of pag in transgenic lines.

FIG. 3 shows Western blots demonstrating PA expression of transgenic lines containing different constructs. FIG. 3A shows a western blot of pLD-JW1 $T_1$ transgenic lines for PA quantification. Lane 1: wild type; Lane 2: Ladder; Lane 3: 20 ng PA; Lane 4: 10 ng PA; Lane 5: 5 ng PA; Lane 6: 1:10 dilution pLD-JW1 line; Lane 7: 1:20 dilution pLD-JW1 line. FIG. 3B shows a western blot of pLD-JW2 $T_1$ transgenic lines for PA quantification. Lane 1: wild type; Lane 2: Ladder; Lane 3: 20 ng PA; Lane 4: 10 ng PA; Lane 5: 5 ng PA; Lane 6: blank; Lane 7: 1:10 dilution pLD-JW2 line #1; Lane 8: 1:20 dilution pLD-JW2 line #1; Lane 9: 1:10 dilution pLD-JW2 line #2; Lane 10: 1:20 dilution pLD-JW2 line #2. FIG. 3C shows a western blot comparing extraction buffers, containing CHAPS and SDS, and both, and measuring stability of extracts at 4° C., where "Sup" means supernatant fraction, "Hom" means homogenate (soluble and insoluble fractions). The construct used was pLD-JW2.

FIG. 4 shows western blots of $T_1$ pLD-JW1 plant in continuous light in FIGS. 4A and 4B, and in FIG. 4C shows histogram of μg PA/g fresh tissue in young, mature, and old leaves after 3 and 5 days of continuous illumination.

FIG. 5 shows graphs of the results of macrophage cytotoxic assays for extracts from transgenic plants. FIG. 5A shows supernatant and homogenate samples from $T_0$ pLD-JW1 tested. FIG. 5B shows Supernatant samples from $T_1$ pLD-JW1 tested.

FIG. 6A is a schematic view of tomato vector construct pLD Tom-BADH, while FIG. 6B shows PCR for transformants using 3P/3M primers of the pLD-TOM-BADH tomato vector.

FIG. 7 is a schematic of the pTOM-BADH2-G10-pag tomato vector construct

FIG. 8 shows PCR analysis of the products of tomato vectors using BADH primers, wherein + is pTOM-G10-PA vector control, – is WT Tomato plant, and # 3 is transgenic tomato plant.

FIG. 9A shows tomato seedlings 12 days after seed germination, while 9B shows tomato cotyledons ready for bombardment.

FIG. 10 shows cut and bombarded cotyledons.

FIGS. 11A and B show the response of tomato cotyledons transformed with the pLD-TOM-BADH on RMOP supplemented with 2.5 nm betaine aldehyde, where wild type is illustrated in 11*a* and putative transformant in 11*b*.

FIG. 12 shows the serum anti-PA as determined by ELISA and the in vitro toxin neutralization by serum antibodies following intranasal immunization.

FIG. 13A is a schematic view of a pLDS-F1V vector construct, while FIG. 13B shows restriction enzyme analysis of the pLDS-F1V vector.

FIG. 14A shows PCR reactions to determine pLDS-F1V vector integration into the chloroplast genome of Petit Havana, while 14B shows a second PCR reaction, which is also used to determine pLDS-F1V transgene integration.

FIG. 15A shows a Western Blot of pLDS-F1V from XL1-Blue strain of *Ecoli*, while 15B shows Western Blots of F1V expression in transgenic chloroplasts.

FIG. 16 is a schematic of constructs to be inserted in edible plants, where "gene X" represents each of LF27-PA63, CTB-LF27, LF27-PA63+CTB-LF27, LF27+PA.

FIG. 17A is a schematic view of a pDD34-ZM-gfp-BADH vector construct, while 17B shows the subsequent expression of the construct containing GFP in *E.coli,*

FIG. 18A is a schmetactic of pDD33-ZM-aadA-BADH vector construction, and 18B shows the subsequent expression of the construct in *E.coli* grown on spectinomycin.

FIG. 19(A-C) show GFP expression in embryogenic maize cultures where a is non-transgenic control and b and c are transformed maize embryonic calli.

FIG. 20A shows maize control and transgenic plants on regeneration medium containing spectomycin, while FIG. 20B shows PCR confirmation of chloroplast transgenic plants using appropriate primers.

FIG. 21A is a schematic view of a pDD37-DC-gfp-BADH carrot chloroplast transformation vector, while 21B illustrates GFP expression in *E.coli.*

FIG. 22A is a schematic of a vector construct pDD36-DC aadA-BADH carrot chloroplast transformation vector, while 22B illustrates the expression of the vector using *E.coli* cells grown on spectinomycin.

FIG. 23 (A-D) shows Expression of GFP in different stages of transgenic cultures of carrot.

Figure 24:
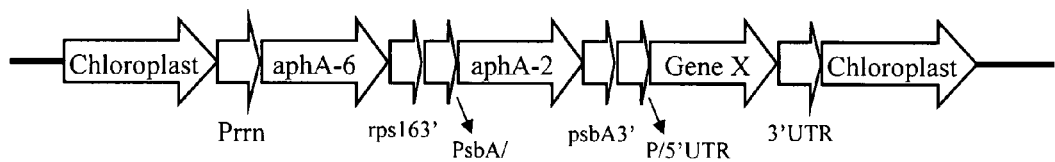

FIG. 24 is a schematic view of a Double Barreled Plastid Vector harboring aphA-6 and aphA-2 genes conferring resistance to aminoglycosides according to the present invention.

DETAILED DESCRIPTION OF THE INVENTION

Chloroplast Engineering

The concept of chloroplast genetic engineering, allows the introduction of isolated intact chloroplasts into protoplasts and regeneration of transgenic plants. Early investigations involving chloroplast transformation focused on the development of in organello systems using intact chloroplasts capable of efficient and prolonged transcription, translation, and expression of foreign genes in isolated chloroplasts. However, the discovery of the gene gun as a transformation device made it possible to transform plant chloroplasts without the use of isolated plastids and protoplasts. Chloroplast genetic engineering has been accomplished in several phases. Studies have been made on the transient expression of foreign genes in plastids of monocots and dicots. Unique to the chloroplast genetic engineering is the development of a foreign gene expression system using autonomously replicating chloroplast expression vectors. Stable integration of a selectable marker gene into the tobacco chloroplast genome was also accomplished using the gene gun. Recently, useful genes conferring valuable traits via chloroplast genetic engineering have been demonstrated. Plants resistant to *Bacillus thuringiensis* (Bt) sensitive and resistant insects were obtained by integrating the cryIAc and cry2A genes into the tobacco chloroplast genome.

Chloroplast genomes of plants have also been genetically engineered to confer herbicide resistance where the introduced foreign genes were maternally inherited. This was a significant step in the development of commercially viable genetically modified plants because it alleviates any concerns over the problem of out-crossing traits with weeds or other crops.

For large-scale foreign protein production, plants are an ideal choice due to the relative ease of genetic manipulation, rapid scale up (million seeds per plant), large biomass, and the potential to find alternative uses for various crops. A remarkable feature of chloroplast genetic engineering is the observation of exceptionally large accumulation of foreign proteins in transgenic plants (as much as 46% of CRY protein in total soluble protein) even in bleached old leaves. Using chloroplast transformation technology, large quantities of protective antigen can be produced in transgenic plants, due to the presence of thousands of copies of transgenes per cell as opposed to only a few copies in nuclear transgenic plants. By “protective antigen” is meant that the antigen elicits an immunogenic response in mammals when administered by an appropriate route in an appropriate amount. Transgenic chloroplast technology has been used to hyper-express bacterial proteins—up to 46% of total soluble protein from *Bacillus* genes, the highest ever reported in transgenic plants. However, large heterologous proteins are not always processed correctly. Furthermore, such proteins are subject to attack by proteolytic enzymes after formation. The cholera toxin B subunit is about 11 kilodaltons in size. The anthrax protective antigen is about 83 kd in size, presenting a significant challenge to production in a chloroplast. A similar challenge is presented by the F1-V antigen, which is a fusion protein. Such fusion proteins have not heretofore been successfully expressed in chloroplasts. Chloroplasts are prokaryotic in nature and express native bacterial genes (like B subunit of cholera toxin) at very high levels (410-fold higher than nuclear expression). Production in chloroplasts is in sharp contrast to nuclear expression, that often requires extensive codon modifications because of high AT content, unfavorable codons, presence of mRNA destabilizing sequences, and cryptic polyadenylation or splice sites. Chloroplast transformation typically utilizes two flanking sequences that, through homologous recombination, insert transgenes into spacer regions between functional genes of the chloroplast genome, thus targeting transgenes to a known location. This eliminates the “position effect” and gene silencing frequently observed in nuclear transgenic plants. Chloroplast genetic engineering is an environmentally friendly approach, minimizing concerns of out-cross of introduced traits via pollen to weeds or other related crops. The chloroplast genome may be engineered without the use of antibiotic resistant genes as well for the development of edible vaccines. The term “edible vaccine” as used herein refers to a substance which may be given orally which will elicit a protective immunogenic response in a mammal.

The difficulty of engineering the chloroplast genome without antibiotic resistant genes has recently been overcome by modifying chloroplasts without these genes. Engineering genetically modified crops without these genes eliminates their potential transfer to the environment and to microbes in the gut. Antibiotic-free selection can be accomplished by using the betaine aldehyde dehydrogenase (BADH) gene from spinach as a selectable marker. Specifically, the Applicant’s published application, WO01/64023, which is hereby incorporated by reference, demonstrates using an antibiotic free selectable marker. The selection process involves conversion of toxic betaine aldehyde (BA) to non-toxic glycine betaine, which also serves as an osmoprotectant and helps confer drought tolerance.

The Applicant has transformed the chloroplast of edible monocot and dicot species, as is illustrated in the accompanying Figures. Specifically, the figures illustrate the stable transformation of carrot and corn chloroplast genomes, which has not previously been accomplished. The transformation of carrot, tomato, and corn allow the production of edible vaccines. These transformed plants also allow the purification and use of the antigens produced by these plants as high purity parenteral vaccines. However, the production of edible vaccines is preferred for their ease of use and low cost.

FIGS. 17A and 18A illustrate the construction of maize chloroplast transformation vector, where flanking regions were amplified using PCR. The PCR products were cloned and the expression cassette was inserted in the transcriptionally active spacer region between trnI/trnA genes. The expression cassette of FIG. 17A has the Prrn promoter driving the expression of GFP and BADH, which are regulated by (5') gene10/rps16 3' and psbA 5'/3' UTRs respectively. The expression cassette of 18A has the Prrn promoter driving the expression of aadA and BADH. The latter gene is regulated by (5') gene10/rps16 3' UTRs.

Functions of the genes in the carrot chloroplast transformation vectors were tested in *E. coli*. For observing GFP expression, cells were plated on LB agar (Amp) plates and incubated at 37° C. overnight. Cells harboring pDD34-ZM-GFP-BADH were seen to fluoresce when exposed to UV light, as is seen in FIG. 17B. To test the aadA gene expression, cells harboring pDD33-ZM-aadA-BADH plasmid were plated on LB agar plates containing spectinomycin (100 mg/ml) and incubated at 37° C. overnight. Transformed cells grow on spectinomycin, as can be seen in FIG. 18B.

FIG. 19 shows GFP expression in embryogenic maize cultures studied under the confocal microscope. FIG. 19A is a non-transgenic control, while FIG. 19B-C are transformed maize embryogenic calli.

The selection in FIG. 19 was initiated two days after bombardment by transferring the bombarded calli to callus induction medium containing BA or streptomycin. After eight weeks, a number of the healthy growing calli from different bombardment experiments were examined for GFP expression under the fluorescent stereomicroscope and the confocal microscope. Somatic embryos were regenerated on maize regeneration medium containing BA or streptomycin.

FIG. 20A shows maize plants on regeneration medium containing streptomycin or betaine aldehyde. FIG. 20A illustrates maize chloroplast transgenic plants which were capable of growth on the selection agent indicating that construction of transgenic maize, while untransfomed maize plants did not grow on the selection medium.

FIG. 20B shows PCR confirmation of chloroplast transgenic plants using appropriate primers. Lanes 1-3, plants transformed with pDD34-ZM-gfp-BADH and Lanes 4-5, plants transformed with pDD33-ZM-aadA-BADH. Lanes – and + represent the negative and positive controls respectively. Genomic DNA was isolated from the leaf tissues and PCR was performed on transformed and non-transformed tissues using appropriate primers.

Figure 21A:
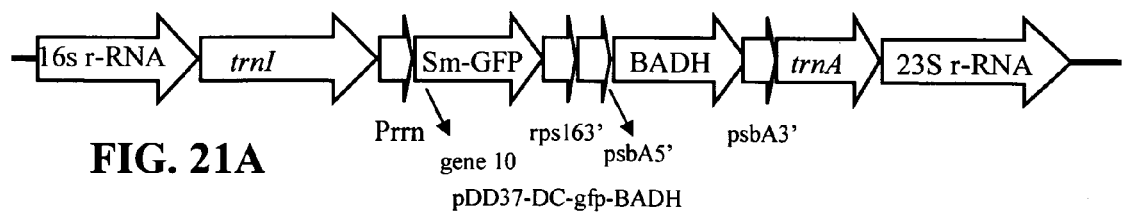
Figure 22:
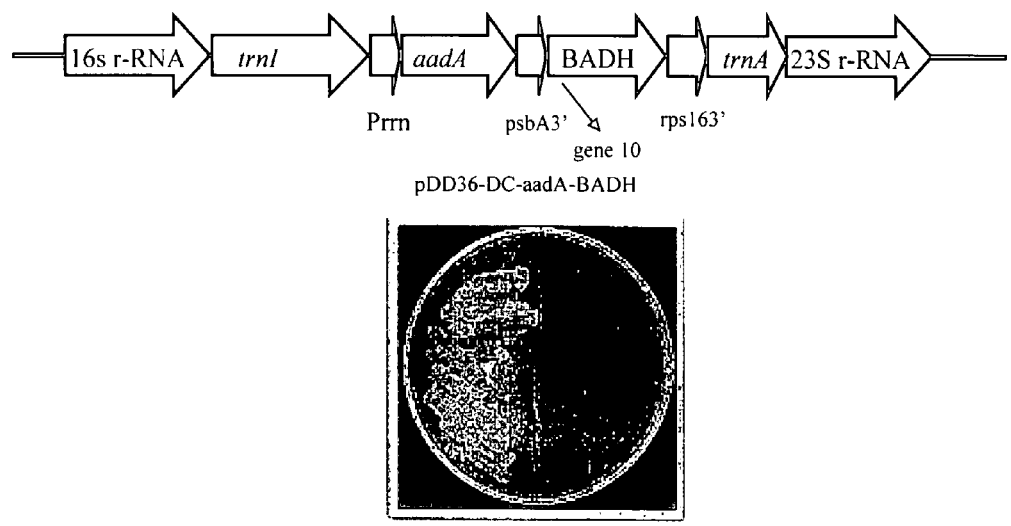
Figure 22A:
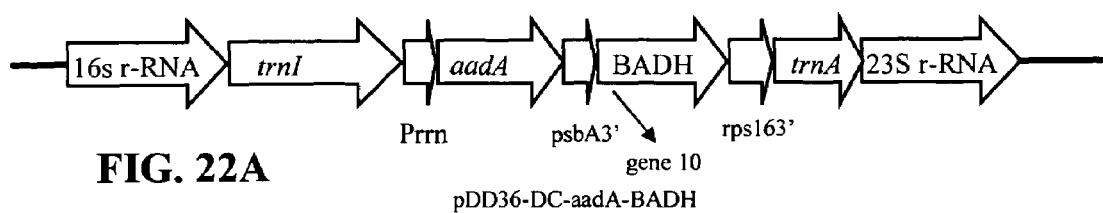

FIGS. 21A and 22A show the schematic construction of carrot chloroplast transformation vectors. The construction of the carrot chloroplast transformation vector illustrated in FIGS. 21A and 22A have flanking regions that were amplified using PCR. The PCR products were then cloned and the expression cassette was inserted in the transcriptionally active spacer region between trnI/trnA genes. The expression cassette of FIG. 21A has the Prrn promoter driving the expression of GFP and BADH, which are regulated by (5') gene10/rps16 3' and psbA 5'/3' UTRs respectively. The expression cassette of FIG. 22A has the Prrn promoter driving the expression of aadA and BADH. The latter gene is regulated by (5') gene10/rps16 3' UTRs.

Functions of the genes in the carrot chloroplast transformation vectors were tested in *E. coli*. For observing GFP expression, cells were plated on LB agar (Amp) plates and incubated at 37° C. overnight. Cells harboring pDD37-DC-GFP-BADH were seen to fluoresce when exposed to UV light (A). To test the aadA gene expression, cells harboring pDD36-DC-aadA-BADH plasmid were plated on LB agar plates containing spectinomycin (100 mg/ml) and incubated at 37° C. overnight. Transformed cells grow on spectinomycin (B).

Figure 21B:
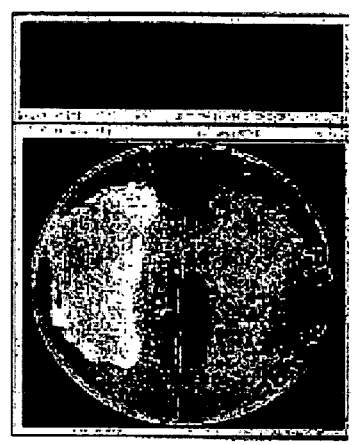
Figure 23A:
Figure 23B:
Figure 23C:
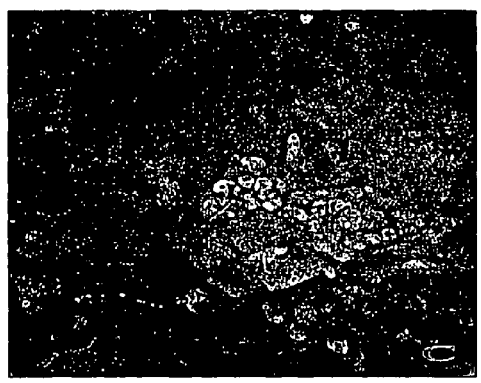
Figure 23D:
Figure 22B:
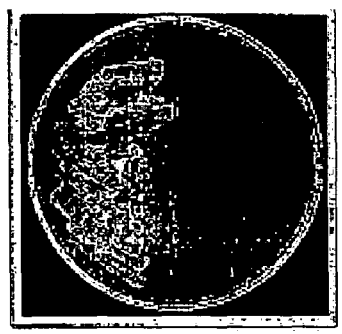

Functions of the genes in the carrot chloroplast transformation vectors were tested in *E. coli*. For observing GFP expression, cells were plated on LB agar (Amp) plates and incubated at 37° C. overnight. Cells harboring pDD34-ZM-GFP-BADH were seen to fluoresce when exposed to UV light as is seen in FIG. 21B. To test the aadA gene expression, cells harboring pDD33-ZM-aadA-BADH plasmid were plated on LB agar plates containing spectinomycin (100 µg/ml) and incubated at 37° C. overnight. Transformed cells grow on spectinomycin, as is seen in FIG. 22B.

FIG. 23 (A-D) shows expression of GFP in different stages of transgenic carrot cultures studied under confocal microscope (A) Untransformed control, (B) Embryogenic callus, (C) Embryogenic callus differentiated into globular somatic embryos and (D) Somatic embryo with differentiated cotyledons.

The aforementioned transformation of maize and carrot chloroplast provides a novel approach for improved vaccines with the creation of an edible vaccine, which provides a heat stable environment, allows easy administration at lower cost, and stimulates the mucosal and systemic immune responses. There still remain a number of hurdles which need to be overcome, such as the fact that protective antigens tend to be very large and unstable proteins (83 kDa); such large proteins have never been expressed before in transgenic chloroplasts, and to date the Applicant is unaware of the expression and assembly of heptamers in transgenic chloroplasts.

Based upon the vector construct described above and set-forth in further detail in this application, it is possible to have a general construct in edible plants where it can be determined through experimentation which construct can elicit the strongest immune response to bacterial toxin challenges such as, but not limiting, plague or anthrax. As an example, FIG. 16 offers a schematic of a construct as an example of construct which could elicit an immune response to anthrax where, in this non-limiting example, gene X is chosen from; 1) LF27-PA63; 2) CTB-LF27; 3) LF27-PA63+CTB-LF27; 4) LF27+PA. These antigens derived from these genes have been shown to elicit the immune response to anthrax. It is noted however that a number of known genes, which code for a bacterial antigen could be utilized in the construct.

Edible vaccines are heat stable unlike conventional vaccines which tend to be heat sensitive. An edible vaccine has a longer shelf life and does not require expensive refrigeration equipment. The heat sensitivity of the conventional vaccine makes it expensive, capricious and destination limited with a series of refrigeration steps during the transportation process from manufacture to final destination. Another major cause for the high cost of biopharmaceutical production is purification; for example, during insulin production, chromatography accounts for 30% of the production cost and 70% of the set up cost. Therefore, oral delivery of properly folded and fully functional biopharmaceuticals could potentially reduce production costs by 90%. In one study it was estimated that the banana could deliver a vaccine (Hepatitis B) at two cents per dose compared to approximately $125 per dose for conventional Hepatitis B vaccine injection. Bioencapsulation of pharmaceutical proteins within plant cells offers protection against digestion in the stomach while allowing successful delivery. In three human clinical trials performed with plant derived vaccines, plant cells proved sufficient for vaccinogen protection against digestion, and the resulting vaccinogen induced systemic and mucosal immune responses without the aid of adjuvants. Oral administration of PA has also been reported to offer protection against *B. anthracis* using an attenuated *Salmonella* strain expressing PA. However, in all these studies the limitation is the low levels of antigen expression which is overcome by the present invention.

EXAMPLES

Chloroplast Transformation

It should be understood that the examples set forth herein are non-limiting examples, and the vectors can be used on a number of plants. The following description is capable of being utilized as illustration and guide work for transformation of plants to express any bacterial antigen gene. It can also be used to express viral antigen genes.

Example 1

The pLD-JW1 Vector

FIG. 1 shows tobacco constructs and PCR confirmation of chloroplast transgene integration. FIG. 1A shows the pLD-JW1 vector used for chloroplast transformation. The trnI and trnA genes were used as flanking sequences for homologous recombination. The constitutive 16s rRNA promoter ("16s" in FIG. 1C) was used to regulate transcription. The aadA gene conferring spectinomycin resistance was used for selection of transgenic shoots. The pag gene coding for anthrax protective antigen was regulated by the psbA promoter and 5' (5UTR) and 3'UTR (T) elements. As shown in FIG. 1B, The pLD-JW2 construct was made by adding orf1,2 from *B. thuringiensis* to the pLD-JW1 vector. FIG. 1C shows a scheme for PCR using the primers 3P and 3M to investigate chloroplast transgene integration. The 3P primer anneals to the native chloroplast genome and the 3M primer anneals to the aadA gene, generating a 1.65 kb PCR product in chloroplast transgenic lines. FIG. 1D shows the results of an analysis of randomly selected clones. Lane 1: Ladder; Lane 2: Negative control wild type tobacco plant DNA; Lane 3: Positive transgenic plant DNA (pLD-5'UTR/HIS/THR/IFNα2b); Lane 4-8: 5 different transgenic lines tested.

The pLD-JW1 vector (8.3 kb, see FIG. 1A) was constructed to transform tobacco chloroplasts. This construct is based on the vector pLD the Applicant has used successfully in previous publications. Specifically, the construct is connected to the Applicants universal vectors, which are described in detail in PCT patent publication WO 99/10513, which is hereby incorporated by reference. The trnI and trnA genes were used as flanking sequences for homologous recombination to insert a pag-containing cassette into the spacer region between these two tRNA genes in the inverted repeat region of the chloroplast genome, as reported previously. It should be noted that it is possible to insert the pag containing cassette into any of a number of spacer regions between genes. The constitutive 16s rRNA promoter, which can be recognized by both the chloroplast encoded RNA polymerase and the nuclear encoded RNA polymerase, was used to drive transcription. Any of a number of promoters functional in plastids and well understood and known in the art can be used to help drive transcription.

The aadA gene conferring spectinomycin resistance was used for selection of transgenic shoots. It is noted however, that the use other antibiotic-resistant genes or an antibiotic free selectable marker such as BADH, could also be used in the construction of the vector. The pag gene coding for anthrax protective antigen was regulated by the psbA 5' and 3' elements. The 5'UTR from psbA, including its promoter, was used for transcription and translation enhancement and the 3'UTR region conferred transcript stability.

One skilled in the art would recognize that an alternative chloroplast vector can be constructed without the use of any promoter, because all polycistronic spacer regions contain a native promoter which can be used to drive transcription.

A second construct was made by adding orf1,2 from *B. thuringiensis* to the pLD-JW1 vector, forming the pLD-JW2 vector (see FIG. 1B). The orf1,2 gene codes for a putative chaperone. Including the orf1,2 gene was done to test whether the putative chaperone could fold a heterologous *Bacillus* protein (i.e., PA) into cuboidal crystals or form inclusion bodies, protect PA from proteolytic degradation, and thereby facilitate purification.

Transgene Integration into the Chloroplast Genome by PCR Analysis:

Chloroplast transgenic lines were generated by particle bombardment as described previously. After bombarding *Nicotiana tabacum* cv. Petit Havana tobacco leaves with the chloroplast vectors, the leaves were grown on selective medium containing 500 μg/ml spectinomycin. Three different genetic events can produce spectinomycin-resistant tobacco shoots: (1) transgene integration into chloroplasts, (2) into the nuclear genome or (3) spontaneous mutants. PCR with two specific primers, 3P and 3M, allowed identification of shoots having the desired chloroplast transgene integration. The 3P primer annealed to the native chloroplast genome and the 3M primer annealed to the aadA gene (see FIG. 1C). Nuclear transformants were eliminated because 3P will not anneal and mutants were ruled out because 3M will not anneal. At least 50 shoots were obtained in the initial transformation, a high frequency which suggests that there was no inhibitory effects of PA. Among clones tested, in both constructs, all were chloroplast transformants. No spontaneous mutants or nuclear transformants were observed (see FIG. 1D).

Chloroplast Integration of Transgenes and Homoplasmy:

Southern blots were done to further verify that the transgenes had been integrated into the chloroplast genome and to determine homoplasmy (containing only transformed chloroplast genomes) or heteroplasmy (containing both transformed and untransformed chloroplast genomes). Total plant DNA was digested with the enzyme BglII which generated a 4.4-kb fragment in wild type, 5.2-kb and 3-kb fragments in pLD-JW1 transgenic lines, and 6.8-kb and 3-kb fragments in pLD-JW2 transgenic lines when hybridized with a 0.81-kb probe made from chloroplast flanking sequences (see FIG. 2A-D). The blots were also hybridized with a 0.52-kb probe made from pag coding sequence (see FIG. 2E). All of the pLD-JW2 plants appeared to be homoplasmic. In the pLD-JW1 plants, transgenic line 2 appeared to be heteroplasmic, which is not uncommon to find in $T_0$ plants. $T_0$ refers to first generation transgenic lines and $T_1$ refers to second generation lines obtained by germination of seeds from $T_0$.

FIG. 2 shows southern blots to investigate the site of transgene integration and determine homoplasmy or heteroplasmy. The figure shows a schematic diagram of the expected products from digestion of wild type untransformed plant as follows: FIG. 2A shows plants transformed with pLD-JW1; FIG. 2B shows plants transformed with pLD-JW2. FIG. 2D shows a flanking sequence probe revealing heteroplasmy in pLD-JW1 line and homoplasmy in pLD-JW2 lines. FIG. 2E shows pag sequence probe showing presence of pag in transgenic lines.

PA Expression in Transgenic Chloroplasts:

Western blots were performed on transgenic lines containing the two different constructs. Full length 83-kDa polypeptide was detected on blots, confirming PA expression in transgenic lines and absence of unique proteases that cleave PA in plant cells (see FIGS. 3A-C). Presence of active furin or trypsin-like proteases would have resulted in a 63-kDa protein due to cleavage at the sequence RKKR (SEQ ID NO:1) (amino acids 164-167). The sequence FFD (SEQ ID NO:2) at residues 312-314 is another site that is highly sensitive to chymottypsin-like enzymes, and cleavage would have resulted in 47- and 37-kDa fragments. No other cleaved PA products were observed (see full length blots shown), demonstrating stability of chloroplast derived PA. Prior to the Applicant's discovery, it was widely believed that proteases would cleave long antigenic bacterial peptides, but this invention illustrates that the antigenic bacterial peptides are free from protolytic degradation.

Figure 3A:
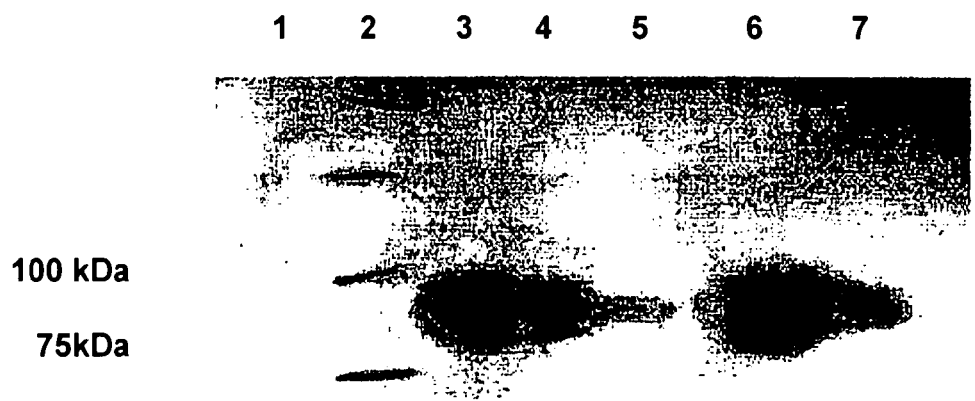
Figure 3B:
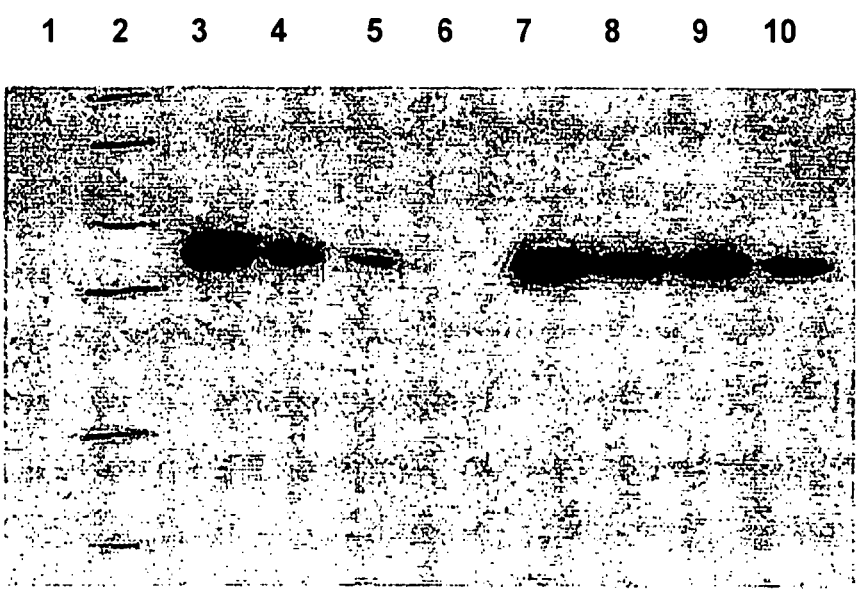
Figure 3C:
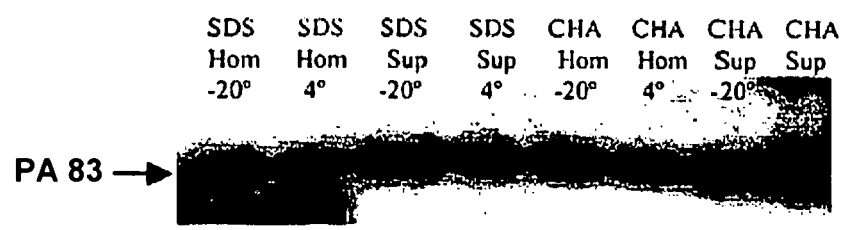

The $T_1$ transgenic lines showed a greater amount of PA in the pLD-JW1 lines as compared to the pLD-JW2 lines. Additional western blots were done comparing two different detergents in the extraction buffers, CHAPS and SDS, and both were found to extract PA equally well (see FIG. 3C). The supernatant and the homogenate were also found to be comparable suggesting that most of the PA is in the soluble fraction. After storage for two days at 4° C. and −20° C., the PA in plant crude extracts is quite stable (see FIG. 3C). Powdered leaf was stored at −80° C. for several months before performing western blots or functional assays; this did not result in any noticeable decrease in PA quantity or functionality. This facilitates long term storage of harvested leaves before extraction of PA for vaccine production. Native PA has been shown to be highly unstable due to proteolysis-sensitive sites, which have been modified to confer better stability.

Quantification of PA in Transgenic Chloroplasts:

In order to quantify the amount of PA in transgenic chloroplasts, western blots were used to observe varying dilutions of the crude extract. PA was quantified using gel documentation software (Bio-Rad). Based on western blot analysis, pLD-JW1 $T_1$ transgenic lines showed 44 µg PA/g of fresh tissue (22 µg/ml). An average tobacco leaf weighed 6.5 g; therefore 286 µg PA could be expressed per leaf. The pLD-JW2 transgenic lines showed lower levels of PA accumulation, probably due to interference of both UTRs, resulting in decrease in translation. We have observed recently that the combination of ORF-psbA5'UTR decreases expression of human serum albumin in transgenic chloroplasts.

The psbA regulatory sequences, including the promoters and UTRs, have been shown to enhance translation and accumulation of foreign proteins under continuous light. Therefore, pLD-JW1 $T_1$ transgenic plants were placed in continuous light and young, mature, and old leaves were collected after 3 or 5 days of continuous illumination. Western blots were performed using different dilutions of crude plant extracts (see FIG. 4A-B). The 3 day mature and young leaves contained 80 µg PA or 108 µg PA/g of fresh tissue. The 5 day old, mature and young leaves contained 32 µg PA, 108 µg PA or 156 µg PA/g of fresh tissue, respectively. Thus, young leaves showed the highest accumulation of PA and old leaves showed the lowest, probably due to proteolytic degradation induced during senescence. These assays quantified only full length PA. In spite of loading 500-1000 fold more protein of untransformed plant extracts, no cross-reacting protein was observed with the monoclonal antibody used.

Figure 4A:
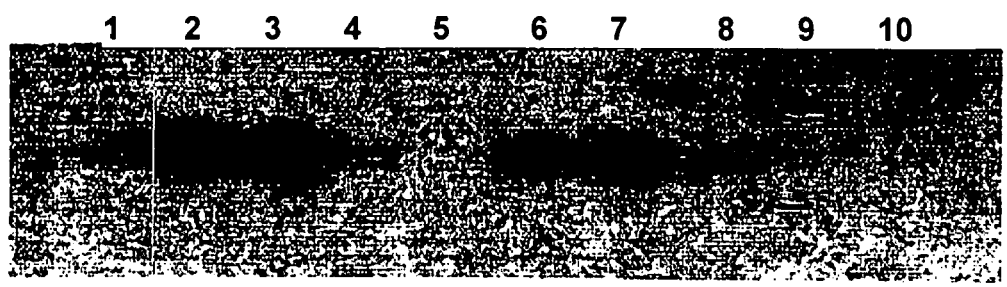
Figure 4B:
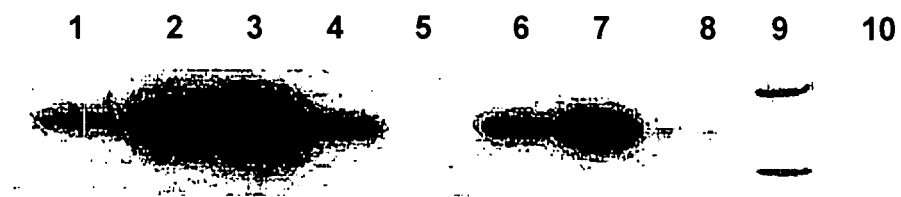
Figure 4C:
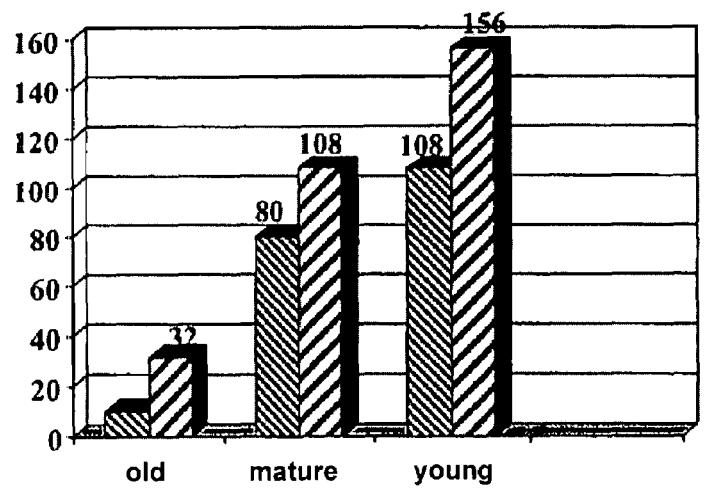

FIG. 4 shows total protein from plant extracts loaded in each lane is shown in parenthesis. FIG. 4A shows pLD-JW1 transgenic line in 3 days of continuous light, 1:20 dilutions. Lane 1: old leaf (187 ng); Lane 2: mature leaf (369 ng); Lane 3: young leaf (594 ng); Lanes 4-5: blank; Lane 6: 10 ng PA; Lane 7: 20 ng PA; Lane 9: ladder; Lane 10: wild type (15,000 ng). FIG. 4B shows pLD-JW1 transgenic line in 5 days of continuous light, 1:20 dilutions. Lane 1: old leaf (214 ng); Lane 2: mature leaf (588 ng); Lane 3: young leaf (745 ng); Lane 6: 10 ng PA; Lane 7: 20 ng PA; Lane 8: blank; Lane 9: ladder; Lane 10: wild type (15,000 ng). FIG. 4C is a histogram of µg PA/g fresh tissue in young, mature, and old leaves after 3 (blue) and 5 (red) days of continuous illumination.

PA accumulation was visualized in crude plant extracts by Coomassie staining. When a capture ELISA was used to quantify PA, it appeared that PA constituted a large percentage of total soluble protein in some extracts. While these values may reflect detection of partially cleaved PA, they do not result from non-specific interaction of the antibodies with any other proteins, because no signal was detected in untransformed plants. However, the data set forth herein is from quantitative scanning of polyacrylamide gels and not from the capture ELISA.

Figure 5A:
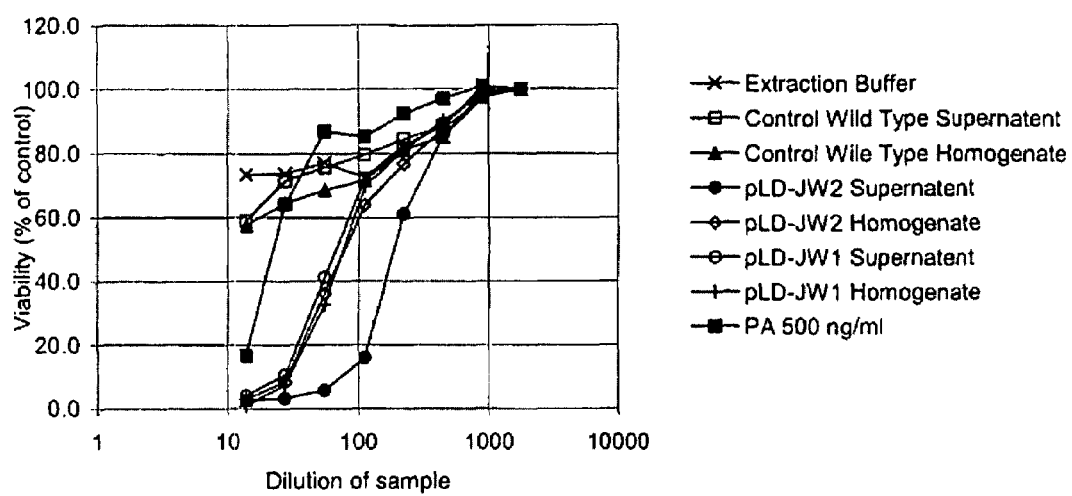
Figure 5B:
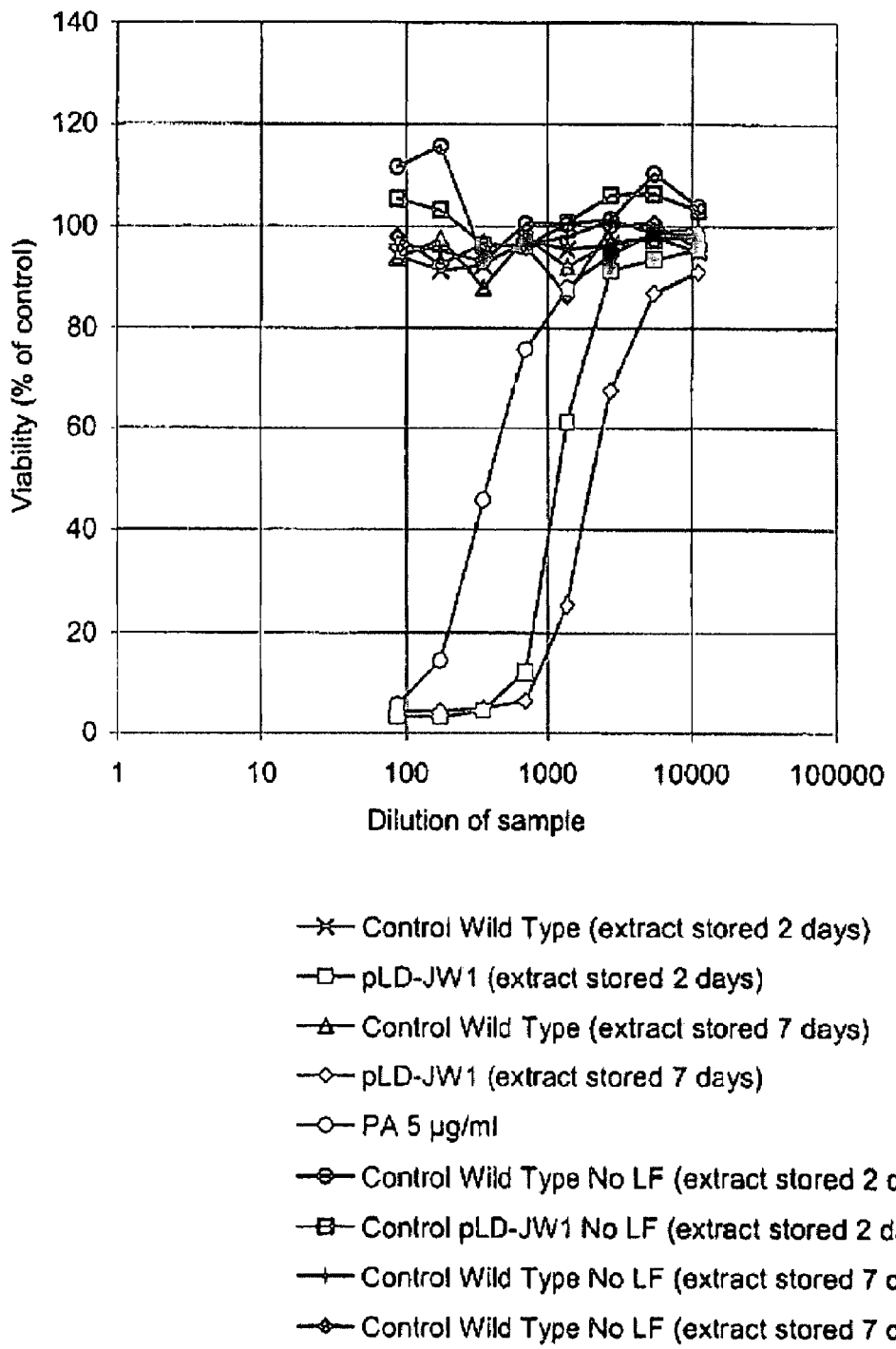
Figure 6A:
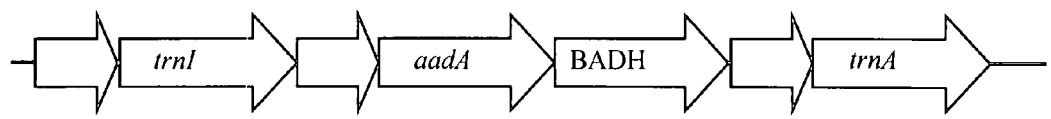
Figure 6B:
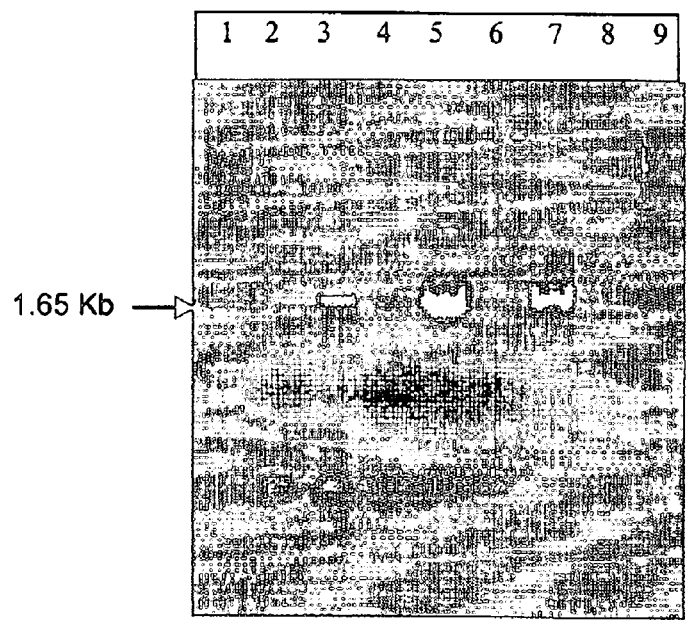

PA Functionality Determined by Macrophage Lysis:

Supernatant and homogenate samples from both $T_0$ constructs, pLD-JW1 and pLD-JW2, were tested. Two different buffers were used to extract proteins—one contained CHAPS detergent and one did not have any detergent. The PA produced in chloroplast transgenic lines was able to bind to the anthrax toxin receptor, be cleaved to the 63-kDa fragment, heptamerize, bind LF, be internalized and lyse the macrophage cells. Therefore the transgenic plants were shown to produce fully functional PA (see FIG. 5A). Active PA was found in both the supernatant and homogenate fractions; but was quantitated only in the former. The assay using CHAPS gave a result of the pLD-JW1 supernatant with the best yield. In the absence of any detergent, the supernatants lysed the macrophage cells better than the homogenates. Crude plant extracts contained up to 5 µg per ml functional PA confirming expression of high levels of functional PA. Supernatant samples from T1 pLD-JW1 transgenic lines were tested and they resulted in approximately 12-25 µg functional PA per ml (see FIG. 5B) and the toxicity was entirely dependent on the presence of LF.

The threat of biological warfare and terrorism is real. The most effective way to prevent or deter effective use of anthrax as a weapon would be to produce an efficacious and inexpensive vaccine. Plants are an inexpensive and easy way to produce recombinant proteins, without human or animal pathogen contamination. Because one acre of tobacco yields up to 40 tons of fresh leaves (40,000 kg in three cuttings), the production could be up to 6.24 kg PA per acre based on expression levels reported in this manuscript. There is less than 50% loss during purification from plant extracts (loss of foreign protein is generally between 30 and 90%), and at 5 µg PA per dose (which is roughly equivalent to prior art vaccine which is in a range of 1.75 to 7 µg PA), one can produce 600 million doses of vaccine per acre of tobacco. Thus a few acres of transgenic tobacco can meet the world's need for the anthrax vaccine.

Experiment Protocol for Example 1

Bombardment and Selection of Transgenic Plants:

Sterile *Nicotiana tabacum* cv. Petit Havana tobacco leaves were bombarded using the Bio-Rad PDS-1000/He biolistic device as previously described. The bombarded leaves were placed on RMOP medium containing 500 µg/ml spectinomycin for two rounds of selection on plates and subsequently moved to jars of MSO medium containing 500 µg/ml spectinomycin.

PCR Analysis to Test Stable Integration:

DNA was extracted from tobacco leaves using Qiagen DNeasy Plant Mini Kit available from Qiagen, Valencia, Calif. PCR was performed using the Perkin Elmer Gene Amp PCR System 2400 (available from Perkin Elmer, Chicago, Ill.). PCR reactions contained template DNA, 1×Taq buffer, 0.5 mM dNTPs, 0.2 mM 3P primer, 0.2 mM 3M primer, 0.05 units/µl Taq Polymerase, and 0.5 mM MgCl$_2$. Samples were run for 30 cycles as follows: 95° C. for 1 min, 65° C. for 1 min, and 72° C. for 2 min with a 5 min ramp up at 95° C. and a 72° C. hold for 10 min after cycles complete. PCR products were separated on 1% agarose gels.

Southern Blot Analysis:

Total plant DNA was digested with BglII and run on a 0.8% agarose gel at 50 V for 2 hours. The gel was soaked in 0.25 N HCl for 15 minutes and then rinsed 2× with water. The gel was soaked in transfer buffer (0.4 N NaOH, 1 M NaCl) for 20 minutes and then transferred overnight to a nitrocellulose membrane. The membrane was rinsed twice in 2×SSC (0.3 M NaCl, 0.03 M Sodium citrate), dried on filter paper, and then crosslinked in the GS GeneLinker (Stratagene, La Jolla, Calif.). The flanking sequence probe was made by digesting pUC-CT vector DNA with BamHI and BglII to generate a 0.81 kb probe. Lee, S. B., Byun, M. O., Daniell, H. Accumulation of trehalose within transgenic chloroplasts confers drought tolerance. *Molecular Breeding* (in press) (2002). The pag probe was made by digesting pag with NcoI to generate a 0.52 kb probe. The probes were labeled with $^{32}$P using the ProbeQuant G-50 Micro Columns (Amersham, Arlington Heights, Ill.). The probes were hybridized with the membranes using Stratagene QUICK-HYB hybridization solution and protocol (Stratagene, La Jolla, Calif.).

Western Blot Analysis:

Approximately 100 mg of leaf tissue was ground in liquid nitrogen with a mortar and pestle and stored at −80° C. for several months. When it was time to extract the proteins, the powder was removed from −80° C. and 200 µl of plant extraction buffer was added and mixed with mechanical pestle (0.1% SDS, 100 mM NaCl, 200 mM Tris-HCl pH 8.0, 0.05% Tween 20, 400 mM sucrose, 2 mM PMSF). The plant extract was then centrifuged for 5 minutes at 10,000×g to pellet the plant material. The supernatant containing the extracted protein was transferred to a fresh tube and an aliquot was taken out, combined with sample loading buffer, boiled, and then run on 8% SDS-PAGE gels for one hour at 80 V, then 2 hours at 150 V. Gels were transferred overnight at 10 V to nitrocellulose membrane. The membrane was blocked with PTM (1×PBS, 0.05% Tween 20, and 3% dry milk). PA was detected with anti-PA monoclonal antibody 14B7. Secondary antibody used was goat anti-mouse IgG conjugated to horseradish peroxidase (American Qualex Antibodies, A106PN).

The stability assay utilized SDS buffer (0.1% SDS, 100 mM NaCl, 10 mM EDTA, 200 mM Tris-HCl pH 8.0, 0.05% Tween 20, 14 mM β-mercaptoethanol, 400 mM sucrose, 2 mM PMSF) and CHAPS buffer (4% CHAPS, 100 mM NaCl, 10 mM EDTA, 200 mM Tris-HCl pH 8.0, 14 mM β-mercaptoethanol, 400 mM sucrose, 2 mM PMSF). Two hundred µl of each buffer was added to 100 mg powdered leaf tissue. For supernatant fractions, the extraction was centrifuged at 10,000×g for 5 minutes and supernatant was removed. For homogenate, the entire extract was used. The samples were stored at 4° C. and −20° C. for two days. The rest of the western protocol was the same as described above. Dilutions of 1:10 and 1:20 of the protein extracts were made and run on the gel along with 20, 10, and 5 ng of PA protein standards to generate a standard curve for protein quantification. After the film was developed, the PA was quantified using the Gel-Doc.

Macrophage Lysis Assays:

Approximately 100 mg of powdered leaf tissue was extracted with 200 µl of extraction buffer. For the supernatant fraction, the buffer and tissue were centrifuged for 5 minutes at 10,000×g and the supernatant was placed in a new tube. For the homogenate, it was all of the tissue and the buffer. RAW 264.7 macrophage cells were plated in 96-well plates in 120 μl DMEM medium and grown to 50% confluence. The medium was aspirated and replaced with 100 μl medium containing 250 ng/ml LF. The control plate received medium with no LF to test toxicity of plant material and buffers. In separate 96-well plates, the plant samples were diluted serially 2-fold and 40 μl of the dilutions were transferred onto the RAW cells so the top row had plant extract at 1:14 dilution. MTT (3-[4,5-dimethylthiazol-2-yl]-2,5-diphenyltetrazolium bromide) was added after 5-10 hours to assess cell death. Gu, M. L., Leppla, S. H., Klinman, D. M. Protection against anthrax toxin by vaccination with a DNA plasmid encoding anthrax protective antigen (Vaccine. 17, 340-344 (1999)).

Example 2

Transformation of the Tomato Chloroplast Genome

Prior to the creation of the pTom-BADH2-G10-pag ~8.8 kb vector construct (FIG. 7), the Applicant constructed the pLD Tom-BADH vector (FIG. 6A) illustrating the ability to transform the chloroplast genome of edible dicots. The Tom-BADH vector was constructed to with two selectable marker genes (BA and spectinomycin) to test ability of transformed plants to grow on BA as compared to spectinomycin. The pLD-Tom-BADH vector contains the chimeric aadA gene and the BADH gene driven by the constitutive 16 S rRNA promoter and regulated by the 3'UTR region of psbA gene from petunia plastid genome. In this construct both, aadA and BADH possess the chloroplast preferred ribosomal binding site, GGAGG. Another suitable vector used for tomato chloroplast transformation is the pLD-Tom-UTR-BADH vector, which has the constitutive 16 S rRNA promoter driving the expression of the dicistron, in which the BADH is under the regulation of the promoter and the 5'UTR of the psbA gene and the 3'UTR of psbA gene, for enhanced expression. FIG. 6B shows the PCR of tomato chloroplast transformed with the pLD-Tom-BADH using 3P/3M primers. Specifically FIG. 6B shows, Lane 1 and 9—1 Kb plus Ladder; 2—mutant; 3—Clone#8; 4—Clone#9; 5—Clone#11; 6—Wild type; 7—Positive control; 8—pLD-Tom-BADH. From results observed in the gel in FIG. 6B, integration of transgene is quite evident.

FIGS. 11A and B show the response of tomato cotyledons transformed with the pLD-Tom-BADH vector grown on RMOP, which is supplemented with 2.5 nm betaine aldehyde, wherein 11A shows the wild type control and 11B shows the transformant.

After successful construction and integration into the tomato chloroplast genome using the pLD Tom-BADH vector of FIG. 6A, the Applicant then constructed the pTom-BADH2-G10-pag ~8.8 kb vector, which is illustrated in FIG. 7. FIG. 7 shows the schematic construct of the pTom-BADH2-G10-pag ~8.8 kb vector, which was constructed containing the selectable marker gene BADH. This construct is also be made using the aad gene to confer spectinomycin resistance in place of the BADH gene. After bombarding the tomato cotyledons (seed leaves or embryonic leaves) with the tomato construct of FIG. 7, the cotyledons were put on selection media containing Betaine Aldeyhyde (BA) and calli formed. The calli were transferred to new selection media to obtain shoots.

Figure 10:
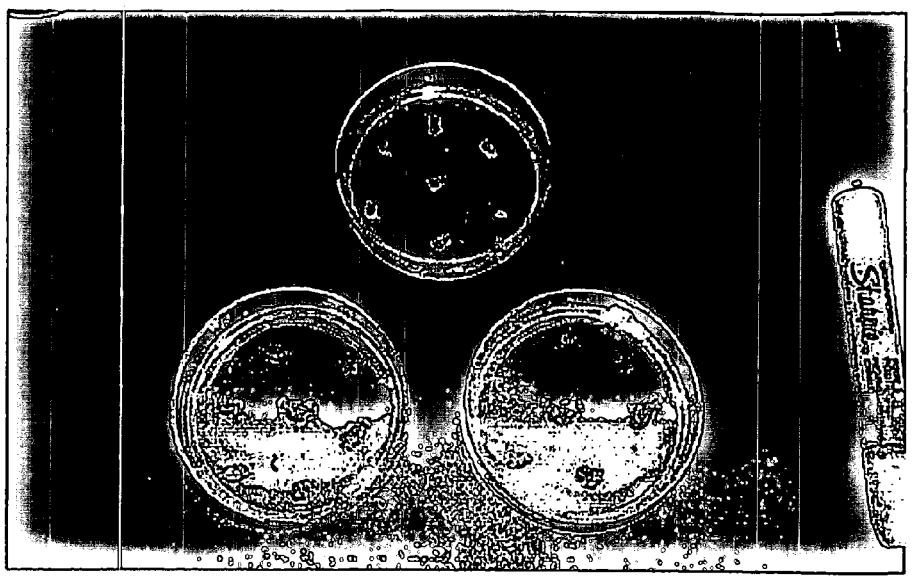
Figures 11A, 11B:
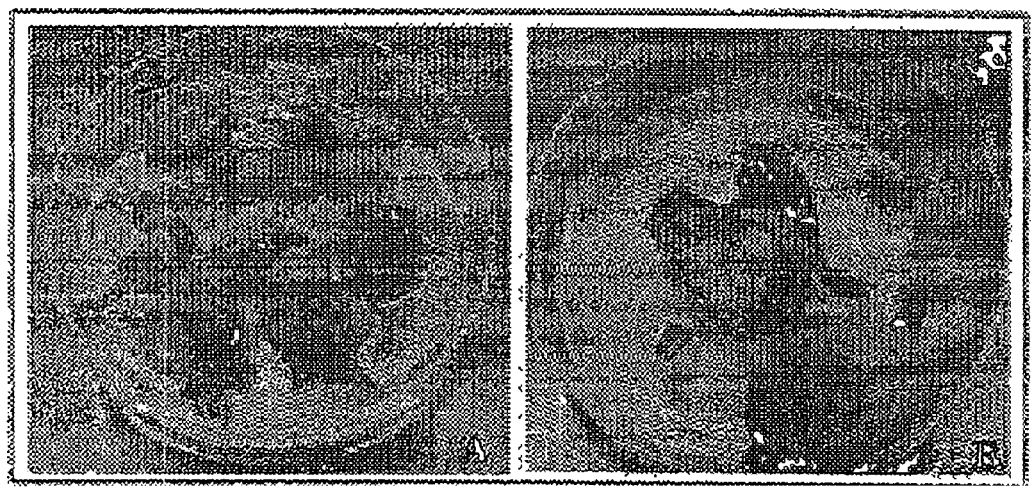

FIG. 10 shows the first selection after bombardment with the pTom-BADH2-G10-pag ~8.8 kb vector, wherein the cotyledons were incubated in the dark for 48 hours and then the bombarded cotyledons were cut. The RMOP medium shown in FIG. 10 is a shoot inducing media. The bombarded cotyledons were grown on 2.5 mM Betaine Aldehyde (BA) for selection.

FIG. 8 shows the PCR test that was performed to determine integration of the pTom-BADH2-G10-pag ~8.8 kb vector, where the tomato shoots were tested with PCR to confirm integration of the transgene. In FIG. 8, the + is pTOM-G10-PA vector control, − is WT Tomato plant, and #3 is the transgenic tomato plant. This confirmation utilized appropriate primers.

To apply the plastid transformation technology to edible plants to produce an edible vaccine, a first generation tomato vector is constructed containing pag. TrnI and trnA are homologous recombination regions in tomato; 5'UTR from psbA is used for translation enhancement and also contains it's own promoter; BADH gene confers Betaine Aldehyde (BA) resistance; G10 is a translation enhancer from the T7 bacteriophage; pag codes for the protective antigen, and T is the psbA terminator.

Figure 7:
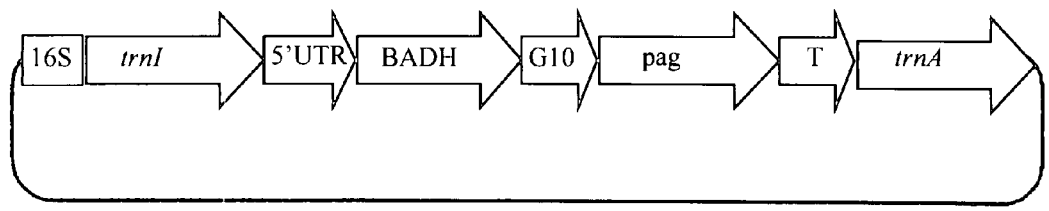

The pDD11 vector is cleaved with NdeI & NotI to remove the gene and leave opened pBlue-G10 region of the vector. The pBlue-T7-pag vector is then cleaved with NdeI & NotI to remove the pag gene ~2.2 kb. The pag gene is ligated into the opened pBlue-G10 vector, and the resulting pBlue-G10-pag is cleaved with SmaI & NotI to remove the G10-pag ~5.2 kb segment from the pBlue-G10-pag vector. Finally the pTom-BADH2 vector is cleaved with SmaI and NotI, and then the G10-pag fragment is ligated into the vector creating a pTOM-BADH2-G10-pag ~8.8 kb (FIG. 7).

PCR Confirmation of Transgene Integration:

After bombarding the tomato cotyledons (seed leaves or embryonic leaves) with the tomato construct vector, pTOM-BADH2-G10-pag ~8.8 kb, the cotyledons are put on selection media containing Betaine Aldeyhyde (BA) and calli formed (FIG. 10). The calli are transferred to new selection media to obtain shoots. Shoots are tested with PCR to confirm integration of the transgene, which utilizes appropriate primers (FIG. 8).

Figure 12:
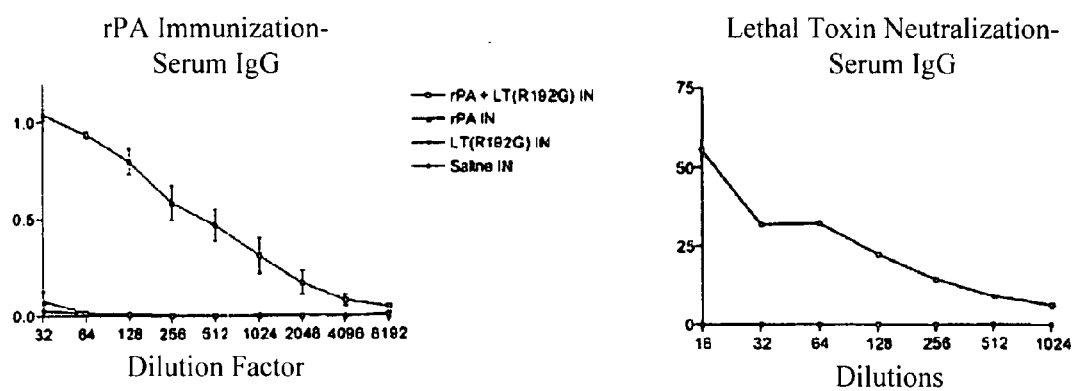

Mucosal and Transcutaneous Immunization Against Anthrax:

Anthrax vaccine studies focused on mucosal and transcutaneous immunization with rPA as a vaccine antigen when delivered in conjunction with a novel adjuvant, designated LT(R192G). This adjuvant was shown to be effective at augmenting protection against a variety of bacterial, viral, and fungal pathogens when delivered with appropriate antigens intranasally, orally, rectally, or transcutaneously. This adjuvant was developed by the Clements laboratory at Tulane University Health Sciences Center with funding from NIH and the Department of Defense and has been evaluated in a number of Phase I and Phase II clinical trials. In rPA studies, a number of immunologic outcomes were measured, but the studies focused primarily on those associated with protection against inhaled pathogens—serum and bronchial lavage (BAL) fluid antibodies. It was demonstrated that mucosal and transcutaneous immunization of mice with rPA induces high levels of antigen-specific antibodies in serum and in bronchoalveolar lavage fluids. Moreover, circulating anti-rPA antibodies are able to neutralize the cytotoxic effect of anthrax Lethal Toxin when tested in macrophage cytotoxicity assays. FIG. 12 shows the serum anti-PA as determined by ELISA and the in vitro toxin neutralization by serum antibodies following intranasal immunization. Equivalent results were seen following transcutaneous immunization.

Tomato Chloroplast Integration Vector:

Since the expression of the foreign protein is desired in chromoplasts of tomato fruit, the gene of interest needs to be under the control of a regulatory sequence that is free from cellular control. In this context, examples of suitable candidate regulatory sequences are the T7 gene 10 leader sequence and cry2Aa2 UTR. The T7 gene 10 leader sequence is used to express foreign proteins in transgenic chromoplasts. The cry2Aa2 UTR accumulates foreign protein in chromoplasts as efficiently as the psbA UTR. The selectable marker for the future generation vectors can optionally be the BADH gene under the regulation of psbA promoter and 5'UTR as psbA is one of the most efficiently translated chloroplast genes in green tissues. Since green tissue is used for introducing the transgene into the chloroplasts in tomato, it is ideal to use the light regulated psbA UTR for the selectable marker.

Tomato Seed Sterilization and Growth Conditions:

FIG. 9 shows tomato seeds (Moneymaker and Ady varieties) that are surface sterilized with ethanol for 30 s, followed by a 20 min treatment with 1.5% NaOCl and 0.1% Tween 20. Seeds are washed thoroughly with sterile water (at least 3-4 times) and transferred to germination media (FIG. 14). Germination media consists of MS salts with 30% sucrose and 0.8% agar. About 20 seeds are inoculated per bottle and placed under a photoperiod of 16 h light and 8 h dark for 8-10 days to obtain cotyledons for particle bombardment. The cotyledons are then excised either as an explant for bombardment or the resulting seedlings are used for transplantation to obtain leaves.

The cotyledons and leaf material are bombarded using the particle gun. After bombardment the explants are then incubated in the dark for 48 h. The cotyledons and leaves are then cut into small pieces and placed onto RMOP media supplemented with 2.5, 5.0 and 7.5 mM of betaine aldehyde for regeneration. In the case of cotyledons, the concentration of 2.5 nm BA is optimal, but not required, as regeneration of putative transformants could be observed after two weeks. Specifically, there is no response on media having higher concentrations of 5.0 and 7.5 mM BA. With leaves, the concentration of 1 and 1.5 mM is optimal for pLD-Tom-BADH and pLD-Tom-UTR-BADH respectively.

Preparation and Analysis of Stable Tomato Plant Transformants:

Selection is optimally performed in the presence of BA, but has also been performed in the presence of antibiotics. After selection, PCR analysis is performed as described above, as is well understood in the art. Finally Southern and northern blot analyses are performed as described above, and well understood in the art, to determine the amount and level of transformation in the chloroplast genome.

Example 3

Transformation of Carrot to Produce Anthrax Vaccine

Carrot (*Daucus carota L.*) is a biennial plant grown for its edible taproot. It is one of the most important vegetables used worldwide for human consumption. Carrot taproots are rich in vitamin A and fiber and are ideal to genetically manipulate in the chromoplast for the production of edible vaccines. For transformation of carrot, flanking sequences (trnI and trnA) are amplified with the help of PCR. Duration for regeneration of carrot plantlets is shortened to four months from eight months when replacing the antibiotic selection with BA. The same chloroplast constructs as described above for tomatoes are used for carrot except that homologous recombination regions i.e. trnI and trnA are derived from carrot chloroplast DNA. The advantage of using carrot is that from small clusters of cells or a small piece of carrot one can get thousands of transgenic plants in a limited space. Moreover, single cells are directly in contact with the culture media surface. Therefore, even a small quantity of selecting agent (betaine aldehyde) is more effective in comparison to other larger tissues. Carrot is easy to store for long periods of time.

Plant Material and Tissue Culture:

Seeds of carrot (*Daucus carota L.* cv *Nantaise*) are sown in pots and placed under a growth chamber with appropriate growth conditions for as little as four weeks to as long as a year. The hypocotyls are then cut into segments of 1 cm long and placed either on semi-solid callus induction medium or in 50 ml MS medium containing 3% sucrose, 0.1 mg/l 2,4-dichlorophenoxyacetic acid (2,4-D) having pH 5.7. After 3 weeks of continuous shaking at 24° C. and 120 rpm, liberated cells are collected on a 100 µM mesh, centrifuged (150×g for 1o min) and resuspended in fresh medium. Rapidly growing cell cultures can be subcultured weekly. Next, callus formation from hypocotyls segments is established on semi-solid MS medium (Carolina Biological supply company) containing 1 mg/l kinetin and 3 mg/l 2,4-D. Homogenously growing calli is subcultured every 4 weeks on fresh medium. The resulting friable calli is then resuspended in 50 ml MS medium containing 3% sucrose and 0.1 mg/kinetin. Finally, suspension-cultured cells are filtered through a 100 µM mesh and subjected to bombardment with chloroplast vectors.

Bombardment and Regeneration of Carrot Chromoplast Transgenic Plants:

Fine cell suspension culture of carrot, evenly spread over MS semi-solid medium is used for bomardment. After bombardment the explants are incubated in the dark for 48 h and later in appropriate light condition (16/8 h day/night cycle at 24° C.). Somatic embryogenesis is induced in a suspension of single cells and small clusters harvested on sieve and low-speed centrifugation. The harvested cells are washed once with hormone free liquid MS medium and resuspended in 40 ml hormone free MS medium containing different concentrations of betaine aldehyde (1.5, 2.5 and 3.5 mM). Transgenic somatic embryos, visible 2 weeks after induction, are selected manually and transferred onto plates with semi-solid MS medium containing 1.5% sucrose and variable concentrations of betaine aldehyde (1.5, 2.5 and 3.5 mM). The plates are sealed with parafilm. After two weeks, somatic embryos development into plantlets which are transferred to soil in pots. Initially, the pots are covered with plastic bags to maintain high humidity and irrigated with progressively reduced concentrations of MS salts for the first week, followed by tap water in the second week. Transgenic plants with stable expression of recombinant protein are then utilized for suitable assays.

Example 4

Construction for the F1V Fusion Protein (the Plague Antigen)

The production of *Yersinia pestis* vaccine in a low nicotine strain of tobacco (LAMD) is accomplished by expressing in chloroplasts the F1-V antigen fusion protein produced from F1 gene (513 bp/15.5 kDa) and the entire V antigen (980 bp/35 kDa). The entire immunogenic sequence will be (441 +980 +6 for a hinge=1437 bp). With the protein of 478 amino acids having a calculated mass of 53,193 and a pI of 5.1 has shown this fusion protein to be immunoprotective.

F1-V was modified to add an EcoR1 site. This fragment is cloned into the universal chloroplast vector, which has been described above, with the psbA 5'UTR upstream of the F1-V fusion. The use of the psbA 5'UTR, is not required, but it has been shown to increase expression of foreign proteins by chloroplast.

Large-scale expression of the fusion protein results in the formation of inclusion bodies as observed with several other foreign proteins expressed in transgenic chloroplasts. These inclusion bodies are easily separated by centrifugation. Another option is use of ammonium sulphate for the precipitation of the protein.

Optionally, a His-tag with an enterokinase cut site was added to the above construct. The His-tag allows for purification on a nickel column with subsequent cleavage of the fusion protein from the His-tag.

The plasmid pPW731 (a pET-24 vector) carrying the gene for the F1V fusion protein was delivered in BLR strain of *E. coli*. Because of the exonuclease activity in BLR, XL1-Blue strain of *E.coli* was transformed with pPW731. Using NdeI and NotI, F1V was cut out of pPW731 and ligated into PCR2.1 with 5' psbA. In order to ligate 5' psbA-F1V into the universal chloroplast vector, pLD-CtV, PCR2.1-5' psbA-F1V was cut with SacI, and blunt ended, then cut with NotI. This was ligated into pLD-CtV which had been cut with EcoRV (blunt end) and NotI. This produced the chloroplast vector pLDS-F1V containing the 5'UTR psbA upstream of F1V, which was then used for bombardment. The use of the psbA 5'UTR has proven to increase expression of foreign proteins by chloroplasts.

Figure 13A:
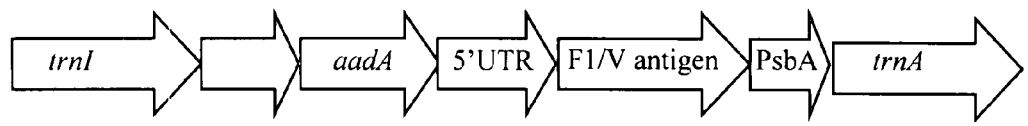

FIG. 13A shows the construct of the pLDS-F1V vector, wherein the vector contains the F1/V antigen gene contained in the spacer region between the trnI and trnA genes. It should be understood that the F1/V antigen gene could be inserted into any of a number of spacer regions between chloroplast genes, which are described and illustrated in Sugita, M. Sugiura, M. Regulation of gene expression in chloroplast of higher plants, *Plant Molecular Biology* 32:315-326, 1996).

Figure 13B:
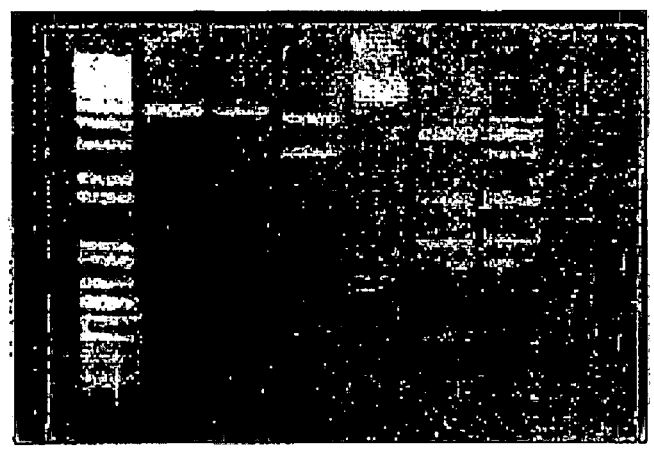

FIG. 13B shows PCR restriction enzyme analysis of pLDS-F1V with XhoI, EcoRI, and NdeI, which showed that the psbA-F1V sequence to be in proper orientation in pLD. (XhoI yielding: 340 bp, 2679 bp, and 4634 bp: EcoRI yielding 682 bp, and 6953 bp: and XhoI/NdeI yielding 340 bp, 925 bp, 1102 bp, 1620 bp, 3610 bp, and incomplete digestion at 2601 bp, and 4550 bp). Lane 1: 1 KB Ladder, Lane 2: pLDS 37C, Lane 3: pLDS 4C, Lane 4: EcoRI, Lane 5: XhoI, Lane 6: XhoI/NdeI (overnight), Lane 7: XhoI/NdeI. The sequencing of pLDS-(5' psbA)-F1V using the 5'UTR primer, which lands on the 5' psbA, showed no changes during vector construction.

Figure 14A:
Figure 14B:
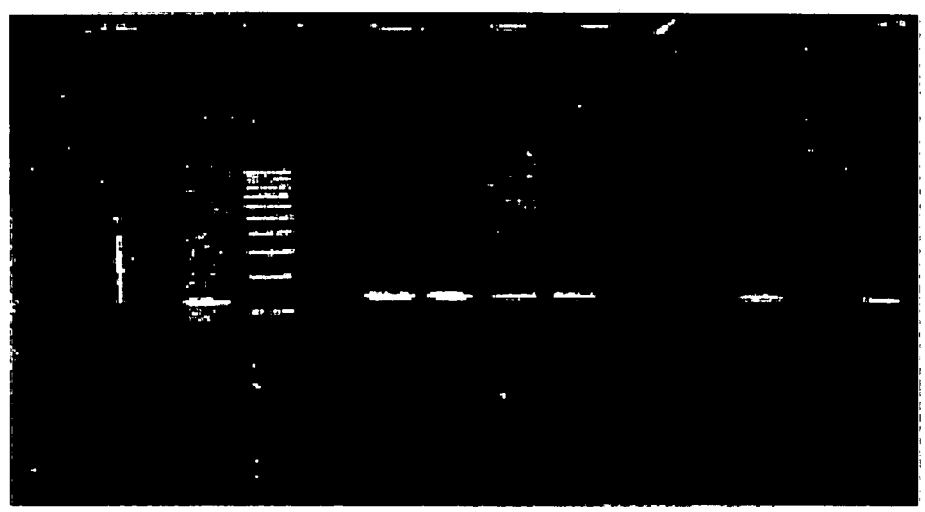

FIGS. 14A and 14B show PCR confirmation of transgene integration into the chloroplast genome.

After bombarding tobacco leaves with pLDS-F1V, there are three possibilities that might produce shoots: chloroplast transgenic, nuclear transgenic, and mutants resistant to spectinomycin. In order to select chloroplast transgenic plants we utilize two PCR reactions. The first (FIG. 14A), which checks for chloroplast intergration, uses 3P and 3M primers which land on the native chloroplast geneome and the aadA gene, respectively. Nuclear transformants are screened out because 3P will not anneal. Mutants are screened out because 3M will not anneal. Positive chloroplast transformants produce a 1.65 Kb PCR product.

The second PCR reaction (FIG. 14B) uses 5P which lands on the aadA gene and 2M which lands on trnA. This produces a PCR product of 1.65 kb+Insert (psbA=203 bp+F1V=1437 bp)=3.29 Kb. Plants 2-5, 8, and 10 clearly contain the transgene.

FIG. 15A shows the western blot of pLDS-F1V from XL1-Blue strain of E. coli, and 15B shows the western blot of plants 1 and 2.

Turning to FIG. 15A showing the Western blot of F1V expression in *E. coli*, the expression in *E.coli* was detected by rabbit anti-F1 as the primary antibody and alkaline phosphatase labeled goat anti-rabbit IgG as the Western blot of F1V expression in *E. coli* was detected by rabbit anti-F1 as the primary antibody and alkaline phosphatase labeled goat anti-rabbit IgG as the secondary antibody. Specifically the western blot in FIG. 15A shows: Lane 1: pLDS-F1V; Lane 2: F1antigen; Lane 3: V antigen; Lane 4: F1V fusion protein.

FIG. 15B illustrates the Western blot of F1V expression in plants as was detected by rabbit anti-F1 and anti-V as primary antibodies and alkaline phosphatase labeled goat anti-rabbit IgG as the secondary antibody. Controls and samples were boiled. Specifically the western blot in FIG. 15B shows: Lane 1: purified F1V fusion protein; Lane 2: Untransformed Petit Havana; Lane 3: Transformed plant line #1; Lane 4: Transformed plant line #2. From this western blot it is clear that transbgenic line 2 has surpassed line 1 in growth and is very healthy confirming that the foreign protein is not toxic to plants.

Cloning F1-V Antigen into Tomato:

The F1-V antigen, which is a bacterial antigen, was cloned into the tomato pLD vector between gene 10 and rps 16 terminator. This was discussed further above. In this case, the selectable marker, BADH, with psbA 5'UTR and psbA 3' follows the rps16 region. The second vector made contains F1-V attached to the carboxy terminus of CTB. CTB serves as a mucosal carrier for this plague protein.

Example 5

Oral Delivery of Recombinant Proteins via Cholera Toxin B Subunit (CTB)

The increased production of an efficient transmucosal carrier molecule and delivery system in chloroplasts of plants allows the production of plant based oral vaccines and fusion proteins with CTB. CTB has previously been expressed in nuclear transgenic plants at levels of 0.01 (leaves) to 0.3% (tubers) of the total soluble protein. To increase expression levels, the chloroplast genome was engineered to express the CTB gene. We observed expression of oligomeric CTB at levels of 4-5% of total soluble plant protein. PCR and Southern Blot analyses confirmed stable integration of the CTB gene into the chloroplast genome. Western blot analysis showed that transgenic chloroplast expressed CTB was antigenically identical to commercially available purified CTB antigen. Also, GM1-ganglioside binding assays confirm that chloroplast synthesized CTB binds to the intestinal membrane receptor of cholera toxin Transgenic tobacco plants were morphologically indistinguishable from untransformed plants and the introduced gene was found to be stably inherited in the subsequent generation as confirmed by PCR and Southern blot analyses. Thus chloroplasts form disulfide bridges to assemble foreign proteins. Spontaneously forming CTB pentamers exhibit intact transcytosis to the external basolateral membrane of intestinal epithelium, and have been widely used as oral vaccine vehicles.

Example 6

Double Barrel Plastid Vectors

Chloroplast transformation has been accomplished only in a few Solanaceous crops so far. There are several challenges in extending this technology to other crops. So far, only green chloroplasts have been transformed in which the leaf has been used as the explant. However, for many crops, including monocots, cultured non-green cells or other non-green plant parts are used as explants. These non-green tissues contain proplastids instead of chloroplasts, in which gene expression and gene regulation systems are quite different. During transformation, transformed proplastids should develop into mature chloroplasts and transformed cells should survive the selection process during all stages of development. Therefore, the major challenge is to provide chloroplasts the ability to survive selection in the light and the dark, at different developmental stages. This is absolutely critical because only one or two chloroplasts are transformed in a plant cell and these plastids should have the ability to survive the selection pressure, multiply and establish themselves while all other untransformed plastids are eliminated in the selection process. The Double Barrel Plastid Vectors accomplish this by using genes coding for two different enzymes capable of detoxifying the same selectable marker (or spectrum of selectable markers), driven by regulatory signals that are functional in proplastids as well as in mature chloroplasts.

The plastid vector described here is one among several such examples (non-limiting example). The chloroplast flanking sequence contains appropriate coding sequences and a spacer region into which the transgene cassette is inserted. Any spacer sequence within the plastid genome could be targeted for transgene integration, including transcribed and transcriptionally silent spacer regions. Both aphA-6 and aphA-2 (nptII) genes code for enzymes that belong to the aminoglycoside phosphotransferase family but they originate from different prokaryotic organisms. Because of prokaryotic nature of the chloroplast genome, these genes are ideal for use in transgenic chloroplasts without any codon optimization. Genes of prokaryotic origin have been expressed at very high levels in transgenic chloroplasts (up to 47% of total soluble protein, DeCosa et al., 2001). Both enzymes have similar catalytic activity but the aphA-6 gene product has an extended ability to detoxify kanamycin and provides a wider spectrum of aminoglycoside detoxification, including amikacin. The advantage of choosing kanamycin as a selectable marker is that it has no natural resistance, unlike spectinomycin resistance observed in most monocots or spontaneous point mutation of the 16 S rRNA gene observed during the selection process. In addition, kanamycin is not in human clinical use as an antibiotic and several crops containing kanamycin resistant nuclear transgenes have been already approved by FDA for human consumption (e.g. flavor savor tomatoes) and currently in the market place.

As shown in FIG. 24, in this non-limiting example, all transgenes are regulated by the plastid Prrn promoter; this 16S rRNA promoter drives the entire rRNA operon in the native chloroplast genome and contains binding sites for both the nuclear encoded and plastid encoded RNA polymerases. Therefore, this promoter is capable of functioning in both proplastids and chloroplasts (green and non-green, in the light and dark). The aphA-6 gene is further regulated by the gene 10 5'UTR capable of efficient translation in the dark, in proplastids present in non-green tissues (see GFP expression in proplastids of non-green cells of corn and carrot in FIGS. 19 and 23 regulated by the 16S rRNA promoter and gene 10 UTR). The rps16 3'UTR has been used to stabilize aphA-6 gene transcripts. The aphA-2 (nptII) gene, on the other hand is regulated by the psbA promoter, 5' and 3' UTRs, which are light regulated and highly efficient in the light, in chloroplasts (see A. Fernandez-San Millan, A. Mingeo-Castel, M. Miller and H. Daniell, 2003, A chloroplast transgenic approach to hyper-express and purify Human Serum Albumin, a protein highly susceptible to proteolytic degradation. Plant Biotechnology Journal, in press; also see WO 01/72959). Therefore, a combination of both aphA-6 and aphA-2 genes, driven by regulatory signals in the light and in the dark in both proplastids and chloroplasts, provides continuous protection for transformed plastids/chloroplasts around the clock from the selectable agent. The gene(s) of interest with appropriate regulatory signals (gene X) are inserted downstream or upstream of the double barrel selectable system. Because multiple genes are inserted within spacer regions (DeCosa et al 2001, Daniell & Dhingra, 2002), the number of transgenes inserted does not pose problems in transcription, transcript processing or translation of operons (WO 01/64024). In a variation of this example, aphA-6 and aphA-2 genes, coupled with different transgenes are inserted at different spacer regions within the same chloroplast genome using appropriate flanking sequences and introduced via co-transformation of both vectors.

Example 7

Genetic Engineering of the Corn and Ryegrass Chloroplast Genomes

A. Transformation of Corn Chloroplast Genome

For genetic engineering of the corn chloroplast genome, corn specific sequences, flanking the targeted integration site in the corn chloroplast genome (trnI and trnA) were amplified with specific PCR primers and subcloned to flank the betaine aldehyde dehydrogenase (BADH) selectable marker, and green fluorescent protein (GFP) reporter gene expression cassette.

Callus cultures were initiated from aseptically excised immature zygotic embryos (1-2 mm in length), produced on self-pollinated ears of HiII (F1) maize plants. Ears were surface sterilized in a solution containing 2.6% Sodium hypochlorite (prepared with commercial bleach) containing 0.1% Tween 20 (polyoxyethylene sorbitan monolaurate) for 20 miniutes under continuous shaking, then rinsed 4 times in sterile distilled water. The Embryos were then placed on the callus induction medium CI-1, which contained N6 salts and vitamins (463.0 mg/l $(NH_4)_2SO_4$, 2830.0 mg/lKNO$_3$, 400 mg/l $KH_2PO_4$, 166.0 mg/l $CaCl_2$, 185 mg/l $MgSO_4.7H_2O$, 37.3 mg/l $Na_2$-EDTA, 27.85 mg/l $FeSO_4.7H_2O$, 1.6 mg/l $H_3BO_3$, 4.4 mg/l $MnSO_4.H_2O$, 0.8, KI, 1.5 mg/l $ZnSO_4.7H_2O$), 2% sucrose and 1.0 mg/l 2,4- (2,4 dichlorophenoxy acetic acid), with the rounded scutellar side exposed and the flat plumule-radicle axis side in contact with the medium. Callus cultures were maintained in darkness at 25-28° C. and subcultured every two weeks.

Particle Bombardment of Embryogenic Calli

Micro projectiles were coated with DNA (pDA34-ZM-gfp-BADH and pDA33-ZM-aadA-BADH) and bombardment was carried out with the biolistic device PDS1000/He (Bio-Rad).

Prior to bombardment, embryogenic calli were selected, transferred over sterile filter paper (Watman No. 1), and placed on the surface of a fresh medium in standard Petrti plates (100×15 mm). Gold particles (0.6 μm) were then coated with plasmid DNA as follows: 50 μl of washed gold particles were mixed with 10 μl DNA (1 μg/μl), 50 μl of 2.5M $CaCl_2$, 20 μl of 0.1M spermidine and vortexed. Particles were cneterfuged for a few seconds at 3000 rpm and then the ethanol was poured off. Ethanol washing was repeated five times, then the pellet was resuspended in 30 μl of 100% ethanol and placed on ice until it was used for bombardment (the coated particles were used within 2 hours). Bombardment was carried out with the biolistic device PDS1000/He (Bio Rad) by loading the target sample at level 2 in the sample chamber under a partial vacuum (28 inches Hg).

The callus cultures were bombarded with the maize chloroplast transformation vectors using 1100 psi rupture discs. Following bombardment, the explants were transferred to a fresh medium; plates were sealed with micropore tape and incubated in darkness at 25-28° C.

Selection

Selection was intiated two days after bombardment. The bombarded calli were transferred to callus induction medium containing 5-20 mM BA (betaine aldehyde) or 25-100 mg/l streptomycin. Selection was also carried out using 50-150 mM NaCl in combination with the BA to maintain osmotic pressure.

Regeneration

Regeneration was initiated 6 to 8 weeks after bombardment by transferring the calli to a medium R1 containing Ms salts and vitamins supplemented with 1.0 mg/l NAA (α-naphthalene acetic acid), 2% sucrose, 2 g/l myoinositol and 0.3% phytagel at pH 5.8. Regenerated plants were transferred to R2 containing ½ MS salts and vitamins, 3% sucrose and 0.3% phytagel at pH 5.8. Regenerated plants were maintained in light (16/8 hr photoperiod).

Shoot Multiplication

The Surface Steriliztion and Germination of Corn Seeds

Corn seeds were surface sterilized in a solution containg 2.6% Sodium hypochlorite (prepared from commercial bleach) containing 0.1% Tween 20 for 20 minutes under continuos shaking, then rinsed four times in sterile distilled water. Seeds were grown on MS medium at pH 5.8 in darkness. Nodal sections were excised aseptically from three day old seedlings. The nodal sections appear as clear demarcations on the germinated seedlings and represent the seventh node. When excised, the nodal cross sections are 1.3 to 1.5 mm in length.

Particle Bombardment of Nodal Sections

Prior to bombardment, 20-30 nodal sections were placed in the center of each petri plate with acropitila end up. Bombardment was carried out with the maize chloroplast vectors, using 1100, 1300 and 1550 psi rupture discs.

Multiple Shoot Induction and Selection

Nodal section explants are placed acropital end up on shoot multiplication medium SM1 composed of Ms salts and vitamins, 1.0 mg/l 6BA (6-Benzyl amino purine), 3% sucrose and 5 g/l phytagel at pH 5.8 under continuous light at 25° C. Initiation of the shoot-tip clumps from the original shoot tips occurred 2 to 4 weeks after culture. Two days after bombardment, transformed nodal sections were transferred to shoot multiplicaton medium containing 5-20 mM BA or 50-100 mg/l streptomycin selective agents. Subsequent subcultures at two week intervals were carried out by selecting, dividing and subculturing green clumps on selective shoot multiplication medium containing 5-20 mM BA or 25-100 mg/l streptomycin.

Regeneration

The Multiple shoot clumps were regenerated by transferring them to regeneration medium M1 containing MS salts and Vitamins, 5 mg/l IBA and 3% sucrose at pH 5.8. The developed shoots were regenerated by transferring the shoot tip clumps to M2 medium containing ½ MS salts and vitamins, 3% sucrose and 3 g/l phytagel at pH 5.8. It should be further rnoted that all the regeneration media are supplemented with 5-20 mM BA or 25-100 mg/l streptomycin as the selective agents.

To engineer the corn chloroplast genome free of antibiotic resistance genes, maize calli were bombarded with a chloroplast expression vector containing the green fluorescent protein (GFP) and the betaine adehyde dehydrogenase (BADH) genes as selectable or screenable markers. To compare the betaine aldehyde (BA) selection with streptomycin, another chloroplast expression vector was constructed containing the aada and the BADH genes. The number of putative transgenic events was higher on BA selection than on streptomycin. Transgenic corn tissues screened on BA were examined using a laser-scanning confocal microscope. The GFP fluorescence was observed throughout the somatic embryos of corn. Chloroplast transformation of corn provides a suitable avenue for the production of edible vaccines and oral delivery of biopharmaceuticals.

Corn Chloroplast Transformation Vector

Corn chloroplast transformation vector facilitates the integration of transgene into the inverted repeat (IR) region of the corn chloroplast genome. The vector pLD-Corn-BADH contains the chimeric aadA gene and the BADH gene driven by the constitutive 16 S rRNA promoter and regulated by the 3'UTR region of psbA gene from petunia plastid genome. In this construct both, aadA and BADH possess the chloroplast preferred ribosomal binding site, GGAGG. Another vector used for corn chloroplast transformation pLD-corn-UTR-BADH has the constitutive 16 S rRNA promoter driving the expression of the dicistron, but BADH is under the regulation of the promoter and the 5'UTR of the psbA gene and the 3'UTR of psbA gene, for enhanced expression. Since the expression of the foreign protein is desired in chromoplasts of corn seeds, the gene of interest needs to be under the control of a regulatory sequence that is free from cellular control. In this context, examples of suitable candidate regulatory sequences are the T7 gene 10-leader sequence and cry2Aa2 UTR. The T7 gene 10-leader sequence is used to express foreign proteins in transgenic chromoplasts. The cry2Aa2 UTR has been shown by the inventor to accumulate as much foreign protein in chromoplasts as efficient as the psbA UTR in green tissues. Therefore the selectable marker for additional vectors use the BADH gene under the regulation of psbA promoter and 5'UTR, as psbA is one of the most efficiently translated chloroplast genes in green tissues. When green tissue or non-green embryogenic calli are used for introducing the transgene into the corn chloroplast genome, it is preferred to use the light regulated psbA promoter/UTR or 16 S rRNA promoter/gene 10 UTR, respectively.

B. Ryegrass Chloroplast Transformation

Annual ryegrass chloroplast transformation vector facilitates the integration of transgene into the inverted repeat (IR) region of the annual ryegrass chloroplast genome. The vector pLD-Ryegrass-BADH contains the chimeric aadA gene and the BADH gene driven by the constitutive 16 S rRNA promoter and regulated by the 3'UTR region of psbA gene from petunia plastid genome. In this construct both, aadA and BADH possess the chloroplast preferred ribosomal binding site, GGAGG. Another vector used for ryegrass chloroplast transformation pLD-ryegrass-UTR-BADH has the constitutive 16 S rRNA promoter driving the expression of the dicistron, but BADH is under the regulation of the promoter and the 5'UTR of the psbA gene and the 3'UTR of psbA gene, for enhanced expression. When green tissue or non-green embryogenic calli are used for introducing the transgene into the corn chloroplast genome, it is preferred to use the light regulated psbA promoter/UTR or 16 S rRNA promoter/gene 10 UTR, respectively.

Vectors for Production of Edible Anthrax Vaccine in Transgenic Chloroplast of Corn or Ryegrass:

Studies have confirmed the role of PA as the major protective antigen in the humoral response but also indicate a significant contribution of LF and EF to immunoprotection. The LF amino terminal domain, amino acid residues 1-254 (27 kDa) contains all the information necessary for binding PA and mediating translocation, and this domain alone is nontoxic because the catalytic domain of LF, residues 255-776, is responsible for lethality. Titers of antibody to both PA and LF from mice immunized with the combination were 4 to 5 times greater than titers from mice immunized with either alone. Therefore we express the constructs LF27-PA63 (PA63 is the cleaved active form of PA), CTB-LF27 fusion proteins, and LF27 and PA independently within the same edible plant as a standard. The LF27-PA63 and CTB-LF27 constructs are expressed alone and together as an operon in corn and ryegrass. It has been demonstrated that Rotavirus enterotoxin proteins fused with CTB is processed via the MHC II pathway generating a strong T-cell response. Thus CTB-fusion proteins produced in plants are ideal for oral delivery. By expressing the CTB-LF27 and PA-LF27 we maximize immunity to lethal toxin challenge. This is because both Gm1 ganglioside and anthrax toxin receptor (ATR) can be bound by ligands and work synergistically for maximum immune response. A flexible hinge was introduced between fusion proteins to reduce steric hindrance. Specifically a glycine-proline-glycine-proline hinge between CTB-LF27 and proline-glycine-proline-glycine hinge between LF27-PA63 was used. The application of less frequently used codons in plants within the hinge peptide promotes translational arrest during the protein elongation process, facilitating subunit folding prior to translation. The efficiency of folding of some proteins is increased by controlled rates of translation in vivo.

Chloroplast Transformation Protocol for Corn and Ryegrass:

Using either immature embryos (IEs) or embryogenic callus derived from IEs as a target for biolistic gene transfer is a well-established procedure for stable integration into the nuclear genome of corn or ryegrass. For biolistic transfer of integrative chloroplast expression vectors, the gene transfer protocol is adjusted and smaller particle sizes (0.6 μm diameter) are used. Microprojectiles are coated with plasmid DNA (chloroplast vectors) and bombardments are carried out with the biolistic device PDS1000/He (Bio-Rad) as is well-known in the art relating to the use of the "gene-gun." Expression levels from chloroplast regulatory sequences and the size of the proplastids are limiting factors for the successful chloroplast transformation using non-green, embryogenic callus tissues as a target for the gene transfer. Therefore, it is most desirable, when using the present invention with plant species not tested here, to compare green shoot meristematic cultures with non-green embryogenic callus as target tissue for chloroplast transformation. Protocols for the establishment of these tissue types are reported for corn and the grasses and are established in the Alpeters laboratory at University of Florida at Gainesville for ryegrass.

The timing of gene transfer after culture initiation and the duration and level of selection affect transgenic events while reducing the number of chimeric plants and achieving homoplasmy and are best evaluated empirically. BADH and aadA selectable markers are compared with the corresponding selective agents. Selection is to be maintained during the regeneration process of plants. Regenerated plants are then analyzed by PCR and Southern blot for integration in the corn or ryegrass plastome.

PCR is done using DNA isolated from control and transgenic plants in order to distinguish a) true chloroplast transformants from mutants and b) chloroplast transformants from nuclear transformants. In order to test chloroplast integration of the transgenes, the 3' primer will anneal to the selectable marker gene while the 5' primer will anneal to the native chloroplast genome. No PCR product is expected with nuclear transgenic plants or mutants using this set of primers. This screening is essential to eliminate mutants and nuclear transformants. Total DNA from wild-type and transgenic plants is isolated and used as a template for PCR reactions. Southern blots allow one skilled in the art to determine the copy number of the introduced foreign gene per cell as well as to test homoplasmy. There are several thousand copies of the chloroplast genome present in each plant cell. When foreign genes are inserted into the chloroplast genome, not all chloroplasts will integrate foreign DNA resulting in heteroplasmy. To ensure that only the transformed genome exists in transgenic plants (homoplasmy), the selection process is continued. In order to confirm homoplasmy at the end of the selection cycle, total DNA from transgenic plants is probed with the chloroplast border (flanking) sequences (the trnI-trnA fragment). Wild type fragment size is observed along with the larger fragments of transformed plastomes. Presence of a large fragment (due to insertion of foreign genes within the flanking sequences) and absence of the native small fragment confirms homoplasmy. The copy number of the integrated gene is determined by establishing homoplasmy for the transgenic chloroplast genome.

Generate Transgenic Ryegrass and Corn Plants Expressing an Edible Anthrax Vaccine and Characterize Transgene Integration and Expression Using the aforementioned transformation protocols, vectors for the production of an orally administrable form of PA are introduced in ryegrass and corn plants. Site specific vector integration into the ryegrass or corn plastome is then confirmed by PCR and Southern blot analysis as specified. Western blot verification of PA verifies that recombinant anthrax protective antigen proteins are antigenically similar to native PA using monoclonal antibodies against PA (Advanced ImmunoChemical G1-Ba1). PA is quantified by a ELISA using purified PA antigen as standard and commercially available antibody. Electron microscopy is next carried out in mature leaves of chloroplast or mature seeds amyloplasts of transgenic plants to detect inclusion bodies according a protocol and similar to several published electron micrographs of transgenic chloroplasts, with immunogold label of foreign proteins. The PA protein is then purified using a two step protocol, such as that described in Ahuja, N., Kumar, P., & Bhatnagar, R. (2001), Rapid Purification of Recombinant Anthrax-Protective Antigen under Nondenaturing Conditions, *Biochemical and Biophysical Research Communications,* 286, 6-11. The protein is purified on AKTA-FPLC using anion exchange Resource Q column (Pharmacia). The protein is then eluted from the column with a 20 ml decreasing gradient of ammonium sulphate. Fractions of 1 ml each are collected, analyzed on SDS-PAGE, and those containing PA are pooled. With an affinity tag, the PA protein can optionally be purified using metal-chelate affinity chromatography under denaturing conditions. Ten ml of each fraction is then analyzed on 12% SDS-PAGE. Fractions containing the protein are collected, pooled, and dialyzed against 10 mM Hepes buffer containing 50 mM NaCl and stored frozen at −70° C. in suitable aliquots.

Recombinant PA proteins are then assayed for their functional activity in the J774A1 (American Type Culture Collection) macrophage lysis assay. Varying concentrations of PA protein along with LF (1 mg/ml) are added to the cells. The native PA along with LF is kept as the positive control. After 3 h, cell viability is determined using the MTT (3-(4,5-dimethyl thiazol-2-yl),-5-diphenyltetrazolium bromide) dye and the resulting precipitate is dissolved in a buffer containing 0.5% (w/v) sodium dodecyl sulfate, 25 mM HCl in 90% isopropyl alcohol. Absorption at 540 nm is measured and percent viability determined.

PA can be tested for susceptibility to cleavage by trypsin. To do so, the PA protein (1.0 mg/ml) is incubated with trypsin (1 ng/mg of protein) for 30 min at room temperature in 25 mM Hepes, 1 mM CaCl2, 0.5 mM EDTA, pH 7.5. The digestion reaction is stopped by adding PMSF to a concentration of 1 mM. Trypsin nicked PA (1.0 mg/ml) is incubated with LF (1.0 mg/ml) and in 25 mM Tris, pH 9.0, containing 2 mg/ml CHAPS (3-{(3-cholamidopropyl) dimethyl ammonio}-propanesulfonic acid) for 15 min at room temperature. Samples are applied to nondenaturing 4.5% polyacrylamide gel.

The binding of PA protein to cell surface receptor is analyzed in 24 well plates using constant amount of radioiodinated native PA (0.1 mg/ml). J774A.1 (ATCC) cells are washed twice with cold HBSS for 5 minutes each time and then placed on ice. The medium is replaced with cold binding medium (DMEM, Dulbecco's Modified Eagle Medium, without sodium bicarbonate containing 1% bovine serum albumin and 25 mM, Hepes, pH 7.4). The cells are incubated with 0.1 mg/ml of iodinated PA and varying concentrations of the recombinant PA protein at 4° C. for 3 h and then washed with cold HBSS. The cells are then dissolved in 0.1 N NaOH and radioactivity measured in Gamma counter.

Leaves from transgenic lines producing epitope tagged products are frozen and powdered at 4° C. using a microdismembranator and proteins are extracted in PBS with 1% Triton X-100. Fusion proteins are purified by affinity chromatography on a nickel-agarose bed, using standard 6-His methods, as described above.

Assessment of Immunogenic Properties of Transgenic Plant-derived PA:

Corn and ryegrass expressing PA as potential edible vaccines against anthrax are characterized using the protocol described above. These are then evaluated for the ability of PA-expressing corn seeds or corn or ryegrass leaves or bay to function as edible vaccines for the induction of serum and mucosal (bronchial lavage, nasal, vaginal, and fecal) antibodies by ELISA. Antibodies induced by feeding the transgenic corn or ryegrass to mammals neutralize the biologic activity of anthrax lethal toxin. This activity can be confirmed in an in vitro macrophage cytotoxicity assay. Antibody responses in mice and humans following ingestion of transgenic potatoes and corn expressing recombinant bacterial proteins have been successfully demonstrated.

Oral immunization of mice and other mammals by feeding transgenic plants or plant parts is accomplished as follows. In the case of corn and ryegrass, female BALB/c mice are fed transgenic corn or ryegrass, control corn or ryegrass, or soluble rPA in conjunction with the mucosal adjuvant LT(R192G). The amount of rPA fed to control animals is based upon the amount of PA in the transgenic corn or ryegrass fed to the animals. That amount correlates with the amount of transgenic corn or ryegrass a mouse will consume in a one hour period. Mice tend to eat grass if a small amount of vanilla extract is placed on each leaf. Two additional groups can be included in which the mucosal adjuvant LT(R192G) is administered in conjunction with the transgenic or control corn or ryegrass. Edible vaccines administered to mice often require the presence of a mucosal adjuvant due to the small amount of material that can be consumed by a mouse. However, this is not necessary when using the plants of the present invention to vaccinate humans, or other large mammals due to the volume which can be consumed by the animal. Twenty-five micrograms of the adjuvant should be applied directly to the corn or ryegrass before consumption when testing mice.

Intranasal immunization is accomplished in mice as follows. Mice are first lightly anesthetized with Isoflurane for approximately 45 seconds. The immunizing inoculum (5-10 ml per animal/per dose) is delivered intranasally to the external nares of one nostril with a pipette tip.

Oral immunization: Oral inoculations consisted of 500 ml of the antigen preparation in saline delivered intragastrically with a blunt-tip feeding needle (Popper & Sons, Inc.).

Sample collection: Animals are sacrificed following euthanasia by $CO_2$ inhalation. Blood is collected by cardiac puncture and the serum is separated in Microtainer tubes. Bronchoalveolar lavages (BAL) are obtained by inserting a 20 G cannula in the exposed trachea and injecting 1 ml of PBS supplemented with protease inhibitors. The buffer is allowed to bathe the lung for approximately 20 seconds and then it is suctioned out; this procedure is repeated three times in each mouse. The resulting BAL fluid is immediately centrifuged (400 g, 2 min, 4° C.) and the supernatant is saved. To obtain nasal lavages a flexible 24 gauge canula is inserted into the posterior opening of the nasopharynx and a total of 150 ml ml PBS+ protease inhibitor is injected into the opening. The outflow is collected as the nasal wash. Vaginal washes are obtained by washing the vaginal mucosa three times with 50 μl of PBS containing 0.01% $NaN_3$. For determination of fecal IgA, feces are collected and frozen overnight at −70° C., lyophilized, resuspended in 800 μl PBS containing 0.05% sodium azide per 15 fecal pellets, centrifuged at 1,400×g for 5 minutes, and the supernatant stored at −20° C. until assayed.

Evaluation of humoral and mucosal antibodies: Each serum, BAL, nasal wash, vaginal wash, and fecal extract sample is individually analyzed by ELISA. For all ELISA assays, 96-well plates are coated with 500 ng per well of rPA and incubated overnight at 4° C. All subsequent steps are carried out at room temperature. After blocking with 1% BSA, twofold serial dilutions of serum, BAL, nasal wash, vaginal wash, or fecal extract from the experimental animals are added. Alkaline phosphatase conjugated rabbit anti-mouse IgG or anti-mouse IgA are used for determination of total IgG or IgA. Biotinylated anti-mouse IgG1, IgG2a, IgG2b or IgG3 followed by alkaline phosphatase conjugated streptavidin are used to quantify antibody isotypes. Optical density at 405 nm is determined using an ELISA reader.

REFERENCES

The following references, along with all other references mentioned herein, and patent applications to which this application may claim priority, are incorporated herein by reference in their entirety.

1. Ahuja, N., Kumar, P., & Bhatnagar, R. (2001). Rapid Purification of Recombinant Anthrax-Protective Antigen under Nondenaturing Conditions. *Biochemical and Biophysical Research Communications*. 286, 6-11.
2. Altpeter, F., & and Xu J. 2000. Rapid production of transgenic turfgrass (*Festuca rubra* L.) plants. *J. Plant Physiol*. 157, 441-448.
3. Altpeter, F., Vasil, V., Srivastava, V., & Vasil, I. K. (1996b): Integration and expression of the high molecular weight glutenin subunit 1Ax1 into wheat. *Nature Biotechnology* 14, 1155-1159.
4. Altpeter, F., Vasil, V., Srivastava, V., Stoeger, E., & Vasil I. K. (1996a) Accelerated production of transgenic wheat (*Triticum aestivum* L.) plants. *Plant Cell Rep*. 16, 12-17.
5. Altpeter, F., Xu, J., & Ahmed, S. 2000. Generation of large numbers of independently transformed fertile perennial ryegrass (*Lolium perenne* L.) plants of forage—and turf type cultivars. *Mol. Breeding* 6, 519-528.
6. Anderson G W, Leary S C, Williamson E D, Titball R W, Welkos S L, Worsham P L, and Friedlander A M. (1996) Recombinant V antigen protects mice against Pneumonic and Bubonic Plague caused by F1-capsule-positive and negative strains of *Yersinia pestis*. *Infection and Immunity*. 64 (11) 4580-5.
7. Andrews G P, Strachan S T, Benner G E, Sample A K, Anderson J R, Adamovicz J J, Welkos S L, Pullen J K, and Friedlander A M. (1999) Protective efficacy of recombinant *Yersinia* outer proteins against bubonic plague caused by encapsulated and non-encapsulated *Yersinia pestis*. *Infection and Immunity*. 67: 1533-1537.
8. Arakawa T, Cong D K X, Merritt J L, and Langridge W H R. (1997) Expression of cholera toxin B subunit oligomers in transgenic plants. *Transgen. Res*. 6: 403-413.
9. Arakawa, T., Chong D. X. X., Langridge, W. H. R. (1998). Efficacy of a food plant based oral cholera toxin B subunit vaccine. *Nature Biotechnology*, 16, 292-297.
10. Arntzen, C. www.bio.org/food%26ag/vaccine.htm-lArtzen estimates the banana could deliver the vaccine at 2 cents a dose verses $125.00 for an injection.
11. Baillie, L. (2001). The development of new vaccines against *Bacillus anthracis*. *Journal of Applied Microbiology*, 91, 609-613.
12. BBC News (2002) http://news.bbc.co.uk/hi/english/health/newsid_1830000/1830034.stm
13. Beck L R, Cowsar D R, Lewis D H, Cosgrove J R, Lowry S L, and Epperly T A. (1979) A new long-acting microencapsule system for administration of progesterone. *Fertility Sterility*. 31: 545-551.
14. Belyakov I M, Ahlers J D, Clements J D, Strober W, Berzofsky J A. 2000. Interplay of cytokines and adjuvants in the regulation of mucosal and systemic HIV-specific CTL. *Journal of Immunology* 165(11):6454-62.

15. Berneman, A., Belec, L., Fischetti, V. A., Bouvet, J. P. (1998) the specific patterns of human immunoglobulins G antibodies in serum differ from those in autologous secretions. *Infection and immunology,* 66, 4163-4168.

16. Bhatnagar, R., Singh, Y., Leppla, S. H., & Friedlander, A. M. (1989). Calcium is required for the expression of anthrax lethal toxin activity in the macrophage-like cell line J774A.1. *Infect. Immun.,* 57, 2107-2114.

17. Bocci V (1999). The oropharyngeal delivery of interferons: where are we and where do we need to go? *J Interferon Cytokine Res.* 19 (8): 859-61.

18. Bockman D E, Cooper M D. 1973. Pinocytosis by epithelium associated with lymphoid follicles in the bursa of Fabricius, appendix and Peyer's patches. An electron microscopic study. *American Journal of Anatomy* 136: 455-477.

19. Bouvet, J. P., Decroix, N., Pamonsinlapatham, P. (2002). Stimulation of local antibody production: parenteral or mucosal. *Trends in Immunology,* 23 (4), 209-212.

20. Bouvet, J. P., Fischetti, V. A. (1999). Diversity of antibody-mediated immunity at the mucosal immune barrier. *Infection and Immunology,* 67, 2687-2691.

21. Bradley, K. A., Mogridge, J., Mourez, M., Collier, R. J., Young, J. A. (2001) Identification of the cellular receptor for anthrax toxin. *Nature.* 414 (6860). 225-229.

22. Brossier, F., Weber-Levey, M., Mock, M., Sirard, J-C. (2000). Role of toxin functional domains in anthrax pathogenesis. *Infect. Immun.,* 68, 1781-1786.

23. Cárdenas-Freytag L, Cheng E, Mayeux P, Domer J E, Clements J D. 1999. Effectiveness of a vaccine composed of heat-killed *Candida albicans* and a novel mucosal adjuvant, LT(R192G), against systemic *candidiasis.* Infection and Immunity 67(2):826-33.

24. Carlson, P. S. (1973). The use of protoplasts for genetic research. *Proc. Natl. Acad. Sci. USA,* 70, 598-602.

25. Castanon S, Marin M S, Martin-Alonso J M, Boga J A, Casais R, Humara J M, Ordas R J, Parra F. Immunization with potato plants expressing VP60 proteins protects against rabbit hemorrhagic disease virus. *J Virology.* 73:4452-55.

26. Center for Disease Control, Feb. 8th, 2002 http://www.bt.cdc.gov/agent/agentlist.asp 27. Chauhan, V., Singh, A., Waheed, M., Singh, S., & Bhatnagar, R. (2001). Constitutive expression of Protective Antigen of *Bacillus anthracis* in *Escherichia coli. Biochemical and Biophysical Research Communications,* 283, 308-315.

28. Cheng E, Cardenas-Freytag L, Clements J D. 1999. The role of cAMP in mucosal adjuvanticity of *Escherichia coli* heat-labile enterotoxin (LT). Vaccine 18(1-2):38-49 chimeric.

29. Cho, M.-J., Ha, C. D., & Lemaux P. G. (2000) Production of transgenic tall fescue and red fescue plants by particle bombardment of mature seed-derived highly regenerative tissues. *Plant cell Rep.* 19, 1084-1089.

30. Choi A H, Basu M, McNeal M M, Clements J D, Ward R L. 1999. Antibody-independent protection against rotavirus infection of mice stimulated by intranasal immunization with chimeric VP4 or VP6 protein. Journal of Virology 73(9):7574-81.

31. Choi A H, Basu M, McNeal M M, Flint J, VanCott J L, Clements J D, Ward R L. 2000. Functional mapping of protective domains and epitopes in the rotavirus VP6 protein. Journal of Virology 74(24):11574-80.

32. Chong C, Friberg M, Clements J D. 1998. LT(R192G), a non-toxic mutant of the heat-labile enterotoxin of *Escherichia coli*, elicits enhanced humoral and cellular immune responses associated with protection against lethal oral challenge with *Salmonella* spp. Vaccine 16(7): 732-40.

33. Coulson, N. M., Fulop, M., Titball, R. W. (1994). *Bacillus anthracis* protective antigen, expressed in *Salmonella typhimurium* SL 3261, affords protection against anthrax spore challenge. *Vaccine,* 12 (15), 1395-1401.

34. Cramer, C., Boothe, J., Oishi, K. Transgenic Plants for Therapeutic Protein: Linking Upstream and Downstream Strategies. *Current Topics Microbiol. Immunol.,* 240, 95-118 (1998).

35. Cummins J M, Beilharz M W, Krakowka S (1999). Oral use of interferon. *J Interferon Cytokine Res.* 19 (8): 853-7.

36. Daniell H (1993). Foreign gene expression in chloroplasts of higher plants mediated by tungsten particle bombardment. *Methods Enzymol.* 217: 536-556.

37. Daniell H (1997). Transformation and foreign gene expression in plants mediated by microprojectile bombardment. *Meth. Mol. Biol.* 62:453-488.

38. Daniell H (1999). Universal chloroplast integration and expression vectors, transformed plants and products thereof, *World Intellectual Property Organization.* WO 99/10513.

39. Daniell H, and Dhingra A. (2002) Multiple gene engineering, *Current Opinion in Biotechnology,* 13: 136-141.

40. Daniell H, Datta R, Varma S Gray S Lee S B (1998). Containment of herbicide resistance through genetic engineering of the chloroplast genome. *Nature Biotechnology.* 16: 345-348.

41. Daniell H, Khan M S, and Allison L. (2002) Milestones in chloroplast genetic engineering: an environmentally friendly era in biotechnology. *Trends in Plant Science.* 7:84-91.

42. Daniell H, Lee S B, Panchal T, and Wiebe P O. (2001) Expression of native cholera toxin B subunit gene and assembly as functional oligomers in transgenic tobacco chloroplasts. *J Mol. Biol.* 311: 1001-1009.

43. Daniell H, Muthukumar B, and Lee S B. (2001) Marker free transgenic plants: engineering the chloroplast genome without the use of antibiotic selection. *Curr. Genet.* 39: 109-116.

44. Daniell H, Streatfield S J, and Wycoff K. (2001) Medical molecular farming: production of antibodies, biopharmaceuticals and edible vaccines in plants. *Trends in Plant Sci.* 6 (5) 219-226.

45. Daniell H. (2002). Molecular strategies for gene containment. *Nature Biotechnology.* 20: 581-586.

46. Daniell H., Krishnan, M., McFadden, B. A. (1991). Expression of B-glucuronidase gene in different cellular compartments following biolistic delivery of foreign DNA into wheat leaves and calli. *Plant Cell Reports,* 9, 615-619.

47. Daniell H., Krishnan, M., Umabai, U., Gnanam, A. (1986). An efficient and prolonged in vitro translational system from cucumber etioplasts. *Biochem. Biophys. Res. Comun.* 135, 48-255.

48. Daniell H., McFadden, B. A. (1987). Uptake and expression of bacterial and cyanobacterial genes by isolated cucumber etioplasts. *Proc. Natl. Acad. Sci. USA* 84, 6349-6353.

49. Daniell H., Ramanujan, P., Krishnan, M., Gnanam, A., Rebeiz, C. A. (1983). In vitro synthesis of photosynthetic 50. Daniell H., Vivekananda, J., Neilsen, B., Ye, G. N., Tewari, K. K., Sanford, J. C. (1990). Transient foreign gene expression in chloroplasts of cultured tobacco cells following biolistic delivery of chloroplast vectors. *Proc Natl Acad Sci USA.*, 87, 88-92.

51. Daniell, H. (1997). Transformation and foreign gene expression in plants mediated by microprojectile bombardment. *Meth Mol Biol.*, 62, 453-488.

52. Daniell, H. (1999). Universal chloroplast integration and expression vectors, transformed plants and products thereof, *World Intellectual Property Organization.* WO 99/10513.

53. Daniell, H. (2002). Molecular strategies for gene containment in transgenic crops. *Nature Biotechnology,* 20, 581-586.

54. Daniell, H., Datta, R., Varma, S., Gray, S., & Lee, S. B. (1998). *Containment of herbicide resistance through genetic engineering of the chloroplast genome. Nature Biotechnology,* 16, 345-348.

55. Daniell, H., Khan, M. S., & Allison, L. (2002). Milestones in chloroplast genetic engineering: an environmentally friendly era in biotechnology. *Trends in Plant Science,* 7, 84-91.

56. Daniell, H., Lee, S. B., Panchal, T., Wiebe, P. O. (2001b). Expression of the native cholera toxin B subunit gene and assembly of functional oligomers in transgenic tobacco chloroplasts. *Journal of Molecular Biology,* 311, 1001-1009.

57. Daniell, H., McFadden, B. A. (1988). Genetic Engineering of plant chloroplasts. U.S. Pat. Nos. 5,932,479; 5,693,507.

58. Daniell, H., Muthukumar, B., Lee, S. B. (2001c). Marker free transgenic plants: engineering the chloroplast genome without the use of antibiotic selection. *Curr Genet,* 39(2), 109-16.

59. Daniell, H., Rebeiz, C. A. (1982). Chloroplast culture IX: Chlorphyll(ide) A biosynthesis in vitro at rates higher than in vivo. *Biochem. Biophys. Res. Comun,* 106, 466-471.

60. Daniell, H., Streafield, S. J., & Wycoff, K. (2001a). Medical molecular farming: production of antibodies, biopharmaceuticals and edible vaccines in plants. *Trends Plant Sci.,* 6(5), 219-26.

61. Daniell, H.,& Dhingra, A. (2002). Multiple gene engineering. *Current Opinion in Biotechnology,* 13, 136-141.

62. De Cosa, B., Moar, W., Lee, S. B., Miller, M.,& Daniell, H. (2001). Hyper-expression of Bt Cry2Aa2 operon in chloroplasts leads to formation of insecticidal crystals. *Nature Biotechnology,* 19, 71-74.

63. DeGray, G., Rajasekaran, K., Smith, F., Sanford, J., Daniell, H. (2001). Expression of an antimicrobial peptide via the chloroplast genome to control phytopathogenic bacteria and fungi. *Plant Physiology,* 127, 1-11.

64. Dire J D, Long D A, Williams L D, and McGovern T W (2002) CBRNE—Biological warefare agents. *EMedicine Journal.* http://www.emedicine.com/emerg/topic853.htm. 3: 1-44.

65. Dixon, T., Meselson, M., Guillemin, J., & Hanna, P. (1999). Anthrax. *The New England Journal of Medicine,* 341 (11), 815-826.

66. Drum, C. L., Yan, S-Z, Bard, J., Shen, Y-Q, Lu, D., Soelaiman, A., Grabarek, Z., Bohm, A., Tang, W-J. (2002). Structural basis for the activation of anthrax adenylyl cyclase exotoxin by calmodulin. *Nature.* 415, 396-402.

67. Edwards, K., Johnstone, C., & Thompson, C. (1991). A simple and rapid method for preparation of plant genomic DNA for PCR analysis. *Nucleic Acid Res.,* 19, 1349.

68. Eyles J E, Spiers I D, Williamson E D, and Alpar H O. (1998) Analysis of local systemic immunological responses after intra-tracheal, intra-nasal and intra-muscular administration of microsphere co-encapsulated *Yersinia pestis* sub-unit vaccines. *Vaccine.* 16 (20) 2000-9.

69. Eyles J E, Williamson E D, Spiers I D, Stagg A J, Jones S M, and Alpar H O (2000) Generation of protective immune responses to plague by mucosal administration of microsphere co-encapsulated recombinant subunits. *J. Controlled Release*. 63, 191-200.
70. Fang, Y.-D., Akula, C., & Altpeter, F. (2002) Agrobacterium-mediated barley (*Hordeum vulgare L.*) transformation using green fluorescent protein as a visual marker and sequence analysis of the T-DNA::barley genomic DNA junctions. *J Plant Physiol* 159, 1131-1138.
71. Fernandez-San Millan, A., Mingo-Castel, A., Miller, M., Daniell, H. A chloroplast transgenic approach to express and purify pharmaceutical proteins that are highly susceptible to proteolytic degradation. *Plant Biotechnology Journal*. (in press) (2002).
72. Freytag L C, Clements J D. 1999. Bacterial toxins as mucosal adjuvants. Current Topics in Microbiology and Immunology 236:215-36.
73. Ge, B., et al. (1998). Differential effects of helper proteins encoded by the cry2A and cry11A operons on the formation of Cry2A inclusions in *Bacillus thuringiensis*. *FEMS Microbiol. Lett.* 165, 35-41.
74. Gerber S, Lane C, Brown D M, Lord E, DiLorenzo M, Clements J D, Rybicki E, Williamson A L, Rose R C. 2001. Human papillomavirus virus-like particles are efficient oral immunogens when coadministered with *Escherichia coli* heat-labile enterotoxin mutant R192G or CpG DNA. Journal of Virology 75(10):4752-60.
75. Gordon-Kamm, W. J., Baszczynski, W. B., Bruce, W. B., & Tomes, D. T. (1999) Transgenic cereals—*Zea mays* (maize). In: Vasil IK (ed) Molecular improvement of cereal crops. Kluwer, Dordrecht, pp 189-253.
76. Gu, M. L., Leppla, S. H., Klinman, D. M. Protection against anthrax toxin by vaccination with a DNA plasmid encoding anthrax protective antigen. *Vaccine*. 17, 340-344 (1999).
77. Guda C, Lee S B, Daniell H (2000). Stable expression of biodegradable protein based polymer in tobacco chloroplasts. *Plant Cell Rep.* 19: 257-262.
78. Guillobel H C, Carinhanha J I, Cardenas L, Clements J D, de Almeida D F, Ferreira L C. 2000. Adjuvant activity of a nontoxic mutant of *Escherichia coli* heat-labile enterotoxin on systemic and mucosal immune responses elicited against a heterologous antigen carried by a live *Salmonella enterica* serovar Typhimurium vaccine strain. Infection and Immunity 68(7):4349-53.
79. Hanna, P. C., Acosta, D., & Collier, R. J. (1993). On the role of macrophages in anthrax. *Proc. Natl. Acad. Sci. USA,* 90, 10198-201.
80. Haq T A, Mason H S, Clements J D, and Artzen C J. (1995) Oral immunization with a recombinant bacterial antigen produced in transgenic plants. *Science,* 268: 714-716.
81. Heath D G, Anderson J W Jr., Maurot J M, Welkos S L, Andrews J P, Adamovicz J, and Friedlander A M. (1998) Protection against experimental bubonic and pneumonic plague by a recombinant capsular F1-V antigen fusion protein vaccine. *Vaccine.* 16 (11/12) 1131-1137.

82. Hill J., Leary S. C., Griffin K. F., Williamson E. D., and Titbal R. W. (1997) Regions of *Yersinia pestis* V antigen that contribute to protection against plague identified by passive and active immunization. *Infection and Immunity.* 65 (11) 4476-4482.

83. Holmgren J. Lycke N, Czerkinsky C. (1993) Cholera toxin and cholera B subunit as oral-mucosal adjuvant and antigen vector systems. *Vaccine.* 11(12) 1179-84.

84. Inglesby, T. et al. Anthrax as a biological weapon. *JAMA* 281 (18), 1735-1745 (1999).

85. Inglesby, T., Henderson, D., Bartlett, J., Ascher, M., Eitzen, E., Friendlander, A., Hauer, J., MdDade, J., Osterholm, M., O'Toole, T., Parker, G., Perl, T., Russel, P., Tonat, K. (1999). Anthrax as a biological weapon. *JAMA* 281 (18), 1735-1745.

86. Ivins, B., Fellows, P., Pitt, L., Estep, J., Farchaus, J., Friedlander, A., & Gibbs, P. (1995). Experimental anthrax vaccines: efficacy of adjuvants combined with protective antigen against an aerosol *Bacillus anthracis* spore challenge in guinea pigs. *Vaccine,* 13 (18), 1779-1783.

87. Ivins, B., Pitt, M., Fellows, P., Farchaus, J., Benner, G., Waag, D., Little, S., Anderson Jr., G., Gibbs, P., & Friedlander, A. (1998). Comparative efficacy of experimental anthrax vaccine candidates against inhalation anthrax in rhesus macaques. *Vaccine,* 16 (11/12), 1141-1148.

88. Jefferson T, Dermichelli V, and Pratt M. (2000) Vaccines for preventing plague. *Cochrane Database Systems Review.* 2, CD000976.

89. Joellenbeck, L. M., Zwanziger, L. L., Durch, J. S., Strom, B. L. Editors National Academy Press, Washington D.C. Chapter 7 "Anthrax Vaccine Manufacture" in The Anthrax Vaccine. Is it safe? Does it work? pp 180-197 (2002).

90. Jones S M, Day F, Stagg A J, and Williamson. (2000) Protection conferred by a fully recombinant subunit vaccine against *Yersinia pestis* in male and female mice of four inbred strains. *Vaccine.* 19:358-66.

91. Kapusta J, Modelska A, Figlerowicz M, Pniewski T, Letellier M, Lisowa O, Yusibov V, Koprowski H, Plucienniczak A, Legocki A B. (1999) A plant-derived edible vaccine against hepatitis B virus. *FASEB J.* 13(13):1796-9.

92. Kaufmann, A. F., Meltzer, M. I., Schmid, G. P. (1997). The economic impact of a bioterrorist attack: are prevention and postattack intervention programs justifiable? *Emerging Infectious Disease,* 3, 83-94.

93. Klimpel, K. R., Molloy, S. S., Thomas, G., Leppla, S. H. (1992). Anthrax toxin protective antigen is activated by a cell surface protease with the sequence specificity and catalytic properties of furin. *Proc. Natl. Acad. Sci. USA,* 89, 10277-10281.

94. Koo, M., Bendahmane, M., Lettieri, G. A., Paoletti, A. D., Lane, T. E., Fitchen, J. H., Buchmeier, M. J., Beachy, R. N. (1999). Protective immunity against murine hepatitis virus (MHV) induced by intranasal or subcutaneous administration of hybrids of tobacco mosaic virus that carries an MHV epitope. *Proc Natl Acad Sci USA,* 96, 7774-7779.

95. Kota M, Daniell H., Varma S, Garczynski F et al (1999). Overexpression of the *Bacillus thuringiensis* Cry2A protein in chloroplasts confers resistance to plants against susceptible and Bt-resistant insects. *Proc. Natl. Acad. Sci. USA.* 96: 1840-1845.

96. Kotloff K L, Sztein M B, Wasserman S S, Losonsky G A, DiLorenzo S C, Walker R I. 2001. Safety and Immunogenicity of oral inactivated whole-cell *Helicobacter pylori* vaccine with adjuvant among volunteers with or without subclinical infection. Infection and Immunity 69(6):3581-90.

97. Kuby N. (2000). Immunology. (4th Ed.) New York. W. H. Freeman and Company.

98. Kusnadi A, Nikolov Z, Howard J (1997). Production of Recombinant proteins in Transgenic plants: Practical considerations. *Biotechnology and Bioengineering* 56 (5): 473-484.

99. Larrick, J. W., & Thomas, B. W. (2001) Plants proteins in transgenic plants and animals. *Curent Opinion in Biotechnology,* 12, 411-418.

100. Leary S E C, Griffin K F, Garmory H S, Williamson E D, and Titball R W. (1997) Expression of an F1-V fusion protein in attenuated *Salmonella typhimurium* and protection of mice against plague. *Microbial Pathogenesis.* 23: 167-179.

101. Lee, S. B., Byun, M. O., Daniell, H. Accumulation of trehalose within transgenic chloroplasts confers drought tolerance. *Molecular Breeding* (in press) (2002).

102. Lee, S. B., Kwon, H., Kwon, S., Park, S., Jeong, M., Han, S., Daniell, H., Byun, H. (2001). Drought tolerance conferred by the yeast trehalose-6 phosphate synthase gene engineered via the chloroplast genome. *Transgenic Research.* In press.

103. Lencer, W. I., Moe, S., Rufo, P. A. & Madara, J. L. (1995). Transcytosis of cholera toxin subunits across model human intestinal epithelia. *Proc. Natl. Acad Sci USA.,* 92, 10094-10098.

104. Leppla, S. H., Robbins, J. B., Schneerson, R., Shiloach, J. Development of an improved vaccine for anthrax. *J. Clin. Invest.* 110 (2), 141-144 (2002).

105. Mason H S, Ball J M, Shi J J, Jiang X, Estes M K, and Arntzen C J. (1996) Expression of Norwalk virus capsid protein in transgenic tobacco and potato and its oral immunogenicity in mice. *Proc Natl Acad Sci USA.* 93(11): 5335-40.

106. Mason, H. S., Haq, T. A., Clements, J. D., & Arntzen, C. J. (1998). Edible vaccine protects mice against *Escherichia coli* heat-labile enterotoxin (LT): potatoes expressing a synthetic LT-B gene. *Vaccine.* 16, 1336-1343.

107. Mathiowitz, E., Jacob, J. S., Jong, Y. S., Carino, G. P., Chickering, D. E., Chaturvedi, P., Santos, C. A., Vijayarahauau, K., Montgomery, S., Bassett, M., & Morrell, C. (1997). Biologically erodable microspheres as potential oral drug delivery systems. *Nature,* 386, 410-414.

108. May, G. D., Mason, H. S., & Lyons, P. C. (1996). Application of transgenic plants as production systems for pharmaceuticals in ACS symposium series 647. Fuller et al. eds., chapter 13, 196-204.

109. McBride, K. E., Svab, Z., Schaaf, D. J., Hogen, P. S., Stalker, D. M., & Maliga, P. (1995). Amplification of a chimeric *Bacillus* gene in chloroplasts leads to extraordinary level of an insecticidal protein in tobacco. *Biotechnology,* 13, 362-365.

110. McCluskie M J, Weeratna R D, Clements J D, Davis H L. 2001. Mucosal immunization of mice using CpG DNA and/or mutants of the heat-labile enterotoxin of *Escherichia coli* as adjuvants. Vaccine 19(27):3759-68.

111. McNeal M M, Rae M N, Bean J A, Ward R L. 1999. Antibody-dependent and -independent protection following intranasal immunization of mice with rotavirus particles. Journal of Virology 73(9):7565-73.

112. MMWR 2000: 49. Use of anthrax vaccine in the United States. Recommendations of the Advisory Committee on Immunization Practices (ACIP).

113. Molloy, S. S., Bresnahan, P. A., Leppla, S. H. Klimpel, K. R., Thomas, G. (1992). Human furin is a calcium-dependent serine endoprotease that recognizes the sequence Arg-X-X-Arg and efficiently cleaves anthrax toxin protective antigen. *J. Biol. Chem.,* 267 (23), 16396-16402.

114. Moriya, O., Matsui, M., Osorio, M., Miyazawa, H., et al (2002). Induction of hepatitis C virus-specific cytotoxic T lymphocytes in mice by immunization with dendritic cells treated with an anthrax toxin fusion protein. *Vaccine,* 20, 789-796.

115. Morris C B, Cheng E, Thanawastien A, Cardenas-Freytag L, Clements J D. 2000. Effectiveness of intranasal immunization with HIV-gp160 and an HIV-1 Env CTL epitope peptide (E7) in combination with the mucosal adjuvant LT(R192G). Vaccine 18(18):1944-1951.

116. New England Biolabs Catalog (2000-2001). 154.

117. Nicolson, G., Nass, M., & Nicolson, N. (2000). Anthrax vaccine: controversy over safety and efficacy. *Antimicrobics and Infectious Diseases Newsletter,* 18 (1), 1-6.

118. O'Neal C M, Clements J D, Estes M K, Conner M E. 1998. Rotavirus 2/6 viruslike particles administered intranasally with cholera toxin, *Escherichia coli* heat-labile toxin (LT), and LT-R192G induce protection from rotavirus challenge. Journal of Virology 72(4):3390-3.

119. Oplinger M L, Baqar S, Trofa A F, Clements J D, Gibbs P, Pazzaglia G, Bourgeois A L, Scott. D A. Safety and immunogenicity in volunteers of a new candidate oral mucosal adjuvant, LT(R192G). 1997.

120. Owen R L, Pierce N F, Apple R T, W. C. Cray J. 1986. M cell transport of *Vibrio cholerae* from the intestinal lumen into Peyer's patches: a mechanism for antigen sampling and for microbial transepithelial migration. Journal of Infectious Diseases 153:1108-1118.

121. Oyston P C, Russell P, Williamson E D, Titball R W. 1996. An aroA mutant of *Yersinia pestis* is attenuated in guinea-pigs, but virulent in mice. Microbiology 142 (Pt 7):1847-53.

122. Pannifer, A. D., Wong, T. Y., Schwazenbacher, R., Renatus, M., Petosa, C., Bienkowska, J., Lacy. D. B., Collier, R. J., Park, S., Leppla, S. H., Hanna, P., Liddington, R. C. (2001). Crystal structure of anthrax lethal toxin. *Nature,* 414, 229-233.

123. Petosa, C., Collier, R., Klimpel, K., Leppla, S., & Liddington, R. (1997). Crystal structure of the anthrax toxin protective antigen. *Nature,* 385, 833-838.

124. Petridis D, Sapidou E and Calandranis J (1995). Computer-Aided process analysis and economic evaluation of for biosynthetic human insulin production. A case study. *Biotechnology and Bioengineering* 48: 529-541.

125. Pezard, C., Weber, M., Sirard, J. C., Berche, P., Mock, M. (1995). Protective Immunity Induced by *Bacillus anthracis* Toxin-Deficient Strains. *Infection and Immunity.,* 63, 1369-1372.

126. Plague History. 10 Feb. 2002. http://www.ento.vt.edu/IHS/plagueHistory.html#justinian.

127. Price, B. M., Liner, A. L., Park, S., Leppla, S. H., Mateczun, A., Galloway, D. R. (2001). Protection against anthrax lethal toxin challenge by genetic immunization with a plasmid encoding the lethal factor protein. *Infect. Immun.,* 69, 4509-4515.

128. Purvis, I. J., Bettany, A. J., Santiago, T. C., Coggins, J. R., et al (1987). The efficiency of folding of some proteins is increased by controlled rates of translation in vivo. *J. Mol. Biol.,* 193, 413-417.

129. Ramirez, D. M., Leppla, S. H., Schneerson, R., Shiloach, J. Production, recovery and immunogenicity of the protective antigen from a recombinant strain of *Bacillus anthracis. J. Ind. Microbiol. Biotechnol.* 28 (4), 232-238 (2002).

130. Ruf, S., Hermann, M., Berger, I. J., Carer, H., & Bock, R. (2001). Stable genetic transformation of tomato plastids: high level foreign protein expression in fruits. *Nature Biotechnology,* 19, 870-875.

131. Russell P, Eley S M, Hibbs S E, Manchee R J, Stagg A J, and Titball R W. (1995) A comparison of plague vaccine, USP and EV76 vaccine induced protection against *Yersinia pestis* in a murine model. *Vaccine.* 13: 1551-6.

132. Ryan E T, Crean T I, John M, Butterton J R, Clements J D, Calderwood S B. 1999. In vivo expression and immunoadjuvancy of a mutant of heat-labile enterotoxin of *Escherichia coli* in vaccine and vector strains of *Vibrio cholerae.* Infection and Immunity 67(4):1694-701.

133. Sabnani L, and Rao D N. (1999) Identification of immunodominant epitope of F1 antigen of *Yersinia pestis.* FEMS Immunology and Medical Microbiology. 27: 155-162.

134. Sanford, J. C., Smith, F. D., Russell, J. A. (1993). Optimizing the Biolistic Process for Different Biological Applications. *Methods in Enzymolog,* 217, 483-509.

135. Sanford, J. C., Smith, F. D., Russell, J. A. (1993). Optimizing the Biolistic Process for Different Biological Applications. Methods in Enzymology, 217, 483-509.

136. Scharton-Kersten T, Yu J, Vassell R, O'Hagan D, Alving C R, Glenn G M. 2000. Transcutaneous immunization with bacterial ADP-ribosylating exotoxins, subunits, and unrelated adjuvants. Infection and Immunity 68(9):5306-13.

137. Sestak K, Meister R K, Hayes J R, Kim L, Lewis P A, Myers G, Saif L J. 1999. Active immunity and T-cell populations in pigs intraperitoneally inoculated with baculovirus-expressed transmissible gastroenteritis virus structural proteins. Veterinary Immunology and Immunopathology 70(3-4):203-21.

138. Sidorov, V. A., Kasten, D., Pang, S. Z., Hajdukiewicz, P. T. J., Staub, J. M., Nehra, N. S. (1999). Stable chloroplast transformation in potato: use of green fluorescent protein as a plastid marker. *Plant Journal,* 19, 209-216.

139. Singh, Y., Ivins, B. E., Leppla, S. H. (1998). Study of immunization against anthrax with the purified recombinant protective antigen of *Bacillus anthracis. Infect. Immun.,* 66, 3447-3448.

140. Staub, J. M., Garcia, B., Graves, J., Hajdukiewicz, et al (2000). High yield production of human therapeutic protein in tobacco chloroplasts. *Nat Biotechnol.,* 18, 333-338.

141. Straley S C, and Bowmer W S. (1996) Virulence genes regulated at the transcriptional level by Ca+2 in *Yersinia pestis* include structural genes for outer membrane proteins. *Infect. Immun.* 51: 445-454.

142. Streatfield S J, Jilka J M, Hood E E, Turner D D, Bailey M R, Mayor J M, Woodard S L, Beifuss K K, Horn M E, Delaney D E, Tizard I R, and Howard J A. (2001). Plant-based vaccines: unique advantages. *Vaccine.* 19: 2742-2748.

143. Sugita, M. Sugiura, M. Regulation of gene expression in chloroplast of higher plants, Plant Molecular Biology 32:315-326, (1996).

144. Svab, Z., Maliga, P. (1993). High frequency plastid transformation in tobacco by selection for a chimeric aadA gene. *Proc. Natl. Acad. Sci. USA.,* 90, 913-917.

145. Tacket C O, Sztein M B, Lsonosky G A, Wasserman S S, Nataro J P, Edelman R, Pickard D., Dougan G, Chatfield S N, and Lavine M M. (1997) Safety of live oral *Salmonella typhi* vaccine strain with deletions in htrA and aroCaroD and immune response in humans. *Infect Immun.* 65: 452-456.

146. Tacket, C. O., Mason, H. S., Losonsky, G., Clements, J. D., Levine, M. M. & Arntzen, C. J. (1998). Immunogenicity in humans of a recombinant bacterial antigen delivered in a transgenic potato. *Nat Med* 4, 607-9.

147. Titbal R. W., and Williamson E. D. (2001). Vaccination against bubonic and pneumonic plague. *Vaccine.* 19: 4175-4184.

148. Tribble D R, Baqar S, Oplinger M L, Bourgeois A L, Clements J D, Pazzaglia G, Pace J, Walker R I, Gibbs P, Scott. D A. Safety and enhanced immunogenicity in volunteers of an oral, inactivated whole cell *Campylobacter* vaccine co-administered with a modified *E. coli* heat-labile enterotoxin adjuvant—LT(R192G); 1997.

149. Tsafrir, S. M., Gomez-Lim, M. A., Palmer, K. E. (1998). Perspective: edible vaccines—a concept coming age. *Trends in Microbiology,* 6 (11) 449-453.

150. Tuboly T, Yu W, Bailey A, Degrandis S, Du S, Erickson L, Nagy E. (2000) Immunogenicity of porcupine transmissible gastroenteritis virus spike protein expressed in plants. Vaccine. 18: 2023-2028.

151. Tumpey T M, Renshaw M, Clements J D, Katz J M. 2001. Mucosal delivery of inactivated influenza vaccine induces B-Cell-dependent heterosubtypic cross-protection against lethal influenza A H5N1 virus infection. Journal of Virology 75(11):5141-50.

152. Varshney, A., & Altpeter, F. (2001) Stable transformation—and tissue culture response in current European winter wheat (*Triticum aestivum L.*) germplasm. *Mol. Breeding* 8, 295-309.

153. Vasil, I. K., Bean, S., Zhao, J, McClusskey, P., Lookhart, M., Zhao, H.-P., Altpeter, F., & Vasil, V. (2001) Evaluation of baking properties and gluten protein composition of field grown transgenic wheat lines expressing high molecular weight glutenin gene 1Ax1. *J. Plant Physiol.* 158, 521-528.

154. Vrekleij, A. J., & Leunissen, J. M., eds. (1989). *Immuno-gold labeling in cell biology.* CRC Press, Boca Raton, Fla.

155. Walmsley A M and Arntezen C J. (2000) Plants for delivery of edible vaccines. Review. *Curr. Opin. Biotechnology.* 11(12) 1179-84.

156. Walmsley, A., & Arntzen, C. (2000). Plants for Delivery of Edible Vaccines. *Current Opinion in Biotechnology,* 11, 126-129.

157. Wesche, J., Elliot, J., Falnes, P., Olsnes, S., & Collier, R. (1998). Characterization of membranetranslocation by anthrax protective antigen. *Biochemistry,* 37, 15737-15746.

158. Williamson E, Westrich G M, Viney J L. 1999a. Modulating dendritic cells to optimize mucosal immunization protocols. Journal of Immunology 163(7):3668-75.

159. Williamson E D, Eley S M, Griffin K F, Green M, Russell P, Leary S E, Oyston P C, Easterbrook T, Reddin K M, Robinson A and others. 1995. A new improved sub-unit vaccine for plague: the basis of protection. FEMS *Immunol Med Microbiol* 12(3-4):223-30.

160. Williamson E D, Eley S M, Stagg A J, Green M, Russell P, and Titball R W. (1997) A sub-unit vaccine elicits IgG in serum, spleen cell cultures and bronchial washings and protects immunized animals against plague. *Vaccine.* 15 (10) 1079-1084.

161. Williamson E D, Eley S M, Stagg A J, Green M, Russell P, Titball R W. 2000. A single dose sub-unit vaccine protects against pneumonic plague. Vaccine 19(4-5):566-71.

162. Williamson E D, Sharp G J E, Eley S M, Vesey P M, Peppert T C, Titball R W, and Alpar H O. (1996) Local and systemic immune response to microencapsulated sub-unit vaccine for plague. *Vaccine.* 14 (17-18) 1613-1619.

163. Williamson E D, Vesey P M, Gillhespy K J, Eley S M, Green M, and Titball R W. (1999) An IgG titre to the F1 and Vantigens correlates with protection against plague in the mouse model. *Clin Exp Immunol.* 116: 107-114.

164. Williamson E D. (2001) Plague vaccine research and development. J. Applied *Microbiology.* 91: 606-608.

165. Xu, J., Schubert, J., & Altpeter, F. (2001) Dissection of RNA mediated virus resistance in fertile transgenic perennial ryegrass (*Lolium perenne L.*). *Plant J* 26, 265-274.

166. Ye, G. N., Daniell, H., & Sanford, J. C. (1990). Optimization of delivery of foreign DNA into higher-plant chloroplasts. *Plant Mol. Biol.,* 15 (6), 809-819.

167. Yu, J., & Langridge, H. R. (2001). A plant-based multicomponent vaccine protects mice from enteric diseases. *Nat. Biotech.,* 19, 548-552.

168. Yuan L, Geyer A, Hodgins D C, Fan Z, Qian Y, Chang K O, Crawford S E, Parreno V, Ward L A, Estes M K and others. 2000. Intranasal administration of 2/6-rotavirus-like particles with mutant *Escherichia coli* heat-labile toxin (LT-R192G) induces antibody-secreting cell responses but not protective immunity in gnotobiotic pigs. Journal of Virology 74(19):8843-53.

169. Zhang, S., Williams-Carrier, R., & Lemaux, P. G. (2002). Transformation of recalcitrant maize elite inbreds using in vitro shoot meristematic cultures induced from germinated seedlings. *Plant Cell Rep.* (in press).

What is claimed is:

1. A plastid transformation vector for stably transforming a plastid, said plastid vector comprising, as operably linked components, a first flanking sequence, at least one regulatory sequence operable in a plastid, a DNA sequence coding for a protective antigen, a DNA sequence coding for a chaperonin, and a second flanking sequence.

2. A plastid transformation vector for stably transforming a plastid, said plastid vector comprising, as operably linked components, a first flanking sequence, at least one regulatory sequence operable in a plaslid, a DNA sequence coding for a protective antigen, a DNA sequence coding for a chaperonin, and a second flanking sequence, wherein said protective antigen is a bacterial antigen.

* * * * *

UNITED STATES PATENT AND TRADEMARK OFFICE
CERTIFICATE OF CORRECTION

| | | |
|---|---|---|
| PATENT NO. | : 7,354,760 B2 | Page 1 of 1 |
| APPLICATION NO. | : 10/500351 | |
| DATED | : April 8, 2008 | |
| INVENTOR(S) | : Henry Daniell | |

It is certified that error appears in the above-identified patent and that said Letters Patent is hereby corrected as shown below:

In the Specification

Column 1, line 4, under the Title of the Invention section, please insert the following:

--STATEMENT OF FEDERALLY FUNDED RESEARCH

The invention was made with government support under grant no. USDA/ARS 58-3611-2-106 awarded by the United States Department of Agriculture. The government has certain rights in the invention.--

Signed and Sealed this
Seventeenth Day of September, 2013

Teresa Stanek Rea
*Deputy Director of the United States Patent and Trademark Office*

SEQUENCE LISTING

<160> NUMBER OF SEQ ID NOS: 2

<210> SEQ ID NO 1
<211> LENGTH: 4
<212> TYPE: PRT
<213> ORGANISM: Bacillus anthracis

<400> SEQUENCE: 1

```
Arg Lys Lys Arg
1

<210> SEQ ID NO 2
<211> LENGTH: 3
<212> TYPE: PRT
<213> ORGANISM: Bacillus anthracis

<400> SEQUENCE: 2

Phe Phe Asp
1
```